(12) United States Patent
Messersmith et al.

(10) Patent No.: US 8,541,060 B2
(45) Date of Patent: Sep. 24, 2013

(54) SURFACE-INDEPENDENT, SURFACE-MODIFYING, MULTIFUNCTIONAL COATINGS AND APPLICATION THEREOF

(75) Inventors: Phillip B. Messersmith, Clarendon Hills, IL (US); Haeshin Lee, Chicago, IL (US)

(73) Assignee: Northwestern University, Evanston, IL (US)

( * ) Notice: Subject to any disclaimer, the term of this patent is extended or adjusted under 35 U.S.C. 154(b) by 1199 days.

(21) Appl. No.: 11/875,237

(22) Filed: Oct. 19, 2007

(65) Prior Publication Data

US 2008/0149566 A1    Jun. 26, 2008

Related U.S. Application Data

(60) Provisional application No. 60/853,013, filed on Oct. 19, 2006.

(51) Int. Cl.
*B05D 1/18* (2006.01)
*B05D 1/26* (2006.01)
*B05D 1/36* (2006.01)

(52) U.S. Cl.
USPC ............ 427/402; 427/2.1; 210/702; 435/128

(58) Field of Classification Search
None
See application file for complete search history.

(56) References Cited

U.S. PATENT DOCUMENTS

2001/0007762 A1* 7/2001 Echigo et al. ................. 435/128
2003/0087338 A1* 5/2003 Messersmith et al. ....... 435/68.1

FOREIGN PATENT DOCUMENTS
WO    2006091226 A2    8/2006

OTHER PUBLICATIONS

Jerry March et al. March's Advanced Organic Chemistry, 2007, Sixth Edition, pp. 1703-1704.*
Li et al., Electrochemical quartz crystal microbalance study on growth and property of the polymer deposit at gold electrodes during oxidation of dopamine in aqueous solutions, Thin Solid Films 497 (2005) 270-278.*
Zeng et al., Synthesis and Characterization of DOPA-PEG Cojugates, Polymer Preprints, 2000, 41(1), 989-990.*
Love et al., Chem. Rev. 105, 1103 (2005).
Erli et al., Biomed. Eng. Online 2, 15 (2003).
Waite et al., Science 212, 1038 (1981).
Yu et al., Macromolecules 31, 4739 (1998).
Statz et al., J. Am. Chem. Soc. 127, 7972 (2005).
Dalsin et al., J. Am. Chem. Soc. 125, 4253 (2003).
Bharathi et al., Chem. Commun., 2303 (1997).
Alivisatos, Nat. Biotech. 22, 47 (2004).
LaVoie et al., Nature Med. 11, 1214 (2005).
Burzio et al., Biochemistry 39, 11147 (2000).
Sugumaran et al., Arch. Insect Biochem. Phys. 11, 127 (1989).
Gidanian et al., J. Inorg. Biochem. 89, 54 (2002).
Taylor et al., J. Inorg. Chem. 33, 5819 (1994).
Jo et al., Biomaterials 21, 605 (2000).

(Continued)

*Primary Examiner* — Michael Cleveland
*Assistant Examiner* — Francisco Tschen
(74) *Attorney, Agent, or Firm* — Quarles & Brady LLP

(57) ABSTRACT

The present invention provides a surface-independent surface-modifying multifunctional biocoating and methods of application thereof. The method comprises contacting at least a portion of a substrate with an alkaline solution comprising a surface-modifying agent (SMA) such as dopamine so as to modify the substrate surface to include at least one reactive moiety. In another version of the invention, a secondary reactive moiety is applied to the SMA-treated substrate to yield a surface-modified substrate having a specific functionality.

14 Claims, 49 Drawing Sheets

(56) References Cited

OTHER PUBLICATIONS

Pasche et al., J. Phys. Chem. B 109, 17545 (2005).
Li et al., J. Phys. Chem. B 109, 2934 (2005).
Ostuni et al., Langmuir 17, 5605 (2001).
Korobkova et al., Nature 428, 574 (2004).
Ho et al., Adv. Mat. 16, 957 (2004).
Li et al., MRS Bulletin 18, 18 (1993).
Sawada et al., Langmuir 22, 332 (2006).
Carmichael et al., Langmuir 20, 5593 (2004).
Nakagawa et al., Biochem. Biophys. Res. Commun. 272, 505 (2000).
PCT International Search Report and Written Opinion, PCT/US2007/081941, Feb. 28, 2008.
PCT International Preliminary Report on Patentability, PCT/US2007/081941, Apr. 30, 2009.
Dalsin, et al., Bioinspired Antifouling Polymers, Materials Today, 2005, 8(9):38-46.
Li, et al., Electrochemical Quartz Crystal Microbalance Study on Growth and Property of the Polymer Deposit at Gold Electrodes During Oxidation of Dopamine in Aqueous Solutions, Thin Solid Films, 2006, 497:270-278.

* cited by examiner

D Mefp5

SSEEYKGGYYPGNAYHYHSGG
SYHGSGYHGGYKGKYYGKAKK
YYYKYKNSGKYKYLKKARKYHR
KGYKYYGGSS

Y: DOPA
K: Lysine

SURFACE-INDEPENDENT, SURFACE-MODIFYING, MULTIFUNCTIONAL COATINGS AND APPLICATION THEREOF

CROSS-REFERENCE TO RELATED APPLICATIONS

This application claims priority to U.S. Provisional Application No. 60/853,013, filed Oct. 19, 2006, the entirety of which is hereby incorporated by reference herein.

STATEMENT REGARDING FEDERALLY-SPONSORED RESEARCH OR DEVELOPMENT

This invention was made with government support under Grant No. DE 014193 awarded by the National Institute of Health. The U.S. Government has certain rights in this invention.

FIELD OF INVENTION

This invention generally relates to polymeric coatings. More particularly, this invention relates to surface-independent, surface-modifying, multifunctional coatings.

BACKGROUND OF THE INVENTION

Surface Modification

Chemical modification of bulk material substrates plays a central role in modern chemical, biological and material sciences, as well as in applied sciences, engineering and technology. Methods for chemical modification of bulk material substrates have developed by interfacial chemistry using organothiol-metals, enediol-oxides, silane-oxides, and other physicochemical methods, in which the predominant purpose is to impose desired properties on non-functional substrates. Molecules utilized for surface modification mostly have bifunctional end groups in which one end anchors to substrates and the other end provides chemical functionality to the substrate surface.

The existing toolbox for functional modification of material/substrate surfaces includes methods such as self-assembled monolayer (SAM) formation, functionalized silanes, Langmuir-Blodgett deposition, layer-by-layer assembly, and genetically-engineered surface-binding peptides. Although widely implemented in research, these conventional methods have limitations for widespread practical use. For instance, chemical specificity between interfacial modifiers and substrates (e.g., alkanethiols on noble metals and silanes on oxides) is typically required, complex instrumentation is typically required, and the substrate size/shape (Langmuir-Blodgett deposition) is often limited, or multistep procedures for implementation (layer-by-layer assembly and surface-binding genetically engineered peptides) are required. More importantly, the substrates available for conventional surface modification chemistry is the primary limitation.

Mussel Adhesive

Mussels represent a natural surface-independent adhesive. Mussels are promiscuous fouling organisms which attach to virtually all types of inorganic and organic substrates, including classically adhesion-resistant materials such as polytetrafluoroethylene (PTFE) (FIG. 1A). Mussels' adhesive versatility may lie in the amino acid composition of proteins found near the plaque-substrate interface (FIG. 1B-D), which is rich in 3,4-dihydroxy-L-phenylalanine (DOPA) and lysine amino acids. DOPA participates in reactions leading to bulk solidification of the adhesive and forms strong covalent and non-covalent interactions with substrates.

Dopamine is a small molecule compound that contains both catechol (DOPA) and amine (lysine) groups (FIG. 1E). Dopamine can be electro-polymerized onto conducting substrates (Y. Li, et al., *Thin Solid Films*, 497, 270, 2006).

Needed in the art of surface modification is a method of surface-independent modification of a substrate whereby specific functional moieties can be displayed on the surface.

SUMMARY OF THE INVENTION

In the present invention, it is shown that dopamine and related compounds can act as a powerful building block for thin polymer film deposition on virtually any bulk material surface wherein the deposited films are easily adaptable for a remarkable variety of functional uses. In one embodiment the deposition is spontaneous.

In one preferred embodiment, the present invention is a novel surface-independent, surface-modification method whereby substrates are modified to display at least one reactive moiety on the substrate surface by contacting at least a portion of the substrate with a surface-modifying agent (SMA). Because of the surface-independent nature of the present method, specific applications include diverse fields such as biocompatible coatings of medical devices, surface modifications of drug delivery carriers and tissue engineering scaffolds, biosensors, industrial and consumer coatings, semiconductors, surface catalysts and next generation electronic displays.

In a first embodiment, the present invention pertains to a method of modifying a substrate surface, the method comprising contacting at least a portion of the substrate with an alkaline solution under oxidative conditions, the solution comprising a surface-modifying agent (SMA) according to Formula I:

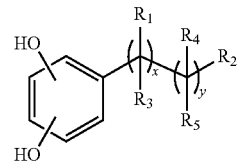

wherein each of $R_1$, $R_2$, $R_3$, $R_4$ and $R_5$ is independently selected from the group consisting of a thiol, a primary amine, a secondary amine, a nitrile, an aldehyde, an imidazole, an azide, a halide, a polyhexamethylene dithiocarbonate, a hydrogen, a hydroxyl, a carboxylic acid, an aldehyde, a carboxylic ester or a carboxamide, provided at least one of $R_1$, $R_2$, $R_3$, $R_4$ and $R_5$ is not a hydrogen atom; wherein x ranges from 0 to 10; wherein y ranges from 0 to 10, provided that x or y is at least 1; and wherein the substrate surface is modified. In a preferred embodiment, the SMA forms a polymeric coat on the substrate surface.

The SMA may also be selected from the group consisting of 3,4-dihydroxy-L-phenylalanine (DOPA), 3,4-dihydroxyphenylalanine methyl ester, dopamine, norepinephrine and epinephrine, and may be an aqueous solution.

In one embodiment of the SMA, x and y are both 1 and $R_1$ and $R_4$ form a double bond when eliminated. However, in alternative embodiments of the SMA, one of $R_1$ or $R_4$ is a halide, a hydroxyl or a thiol and one of $R_3$ or $R_5$ is a hydrogen atom, and $R_2$ is $NH_2$ or NHR, wherein R is an alkyl or aromatic group. In further alternate embodiments of the SMA, x is 1, y is 1, $R_1$ is a hydroxyl, $R_3$, $R_4$ and $R_5$ are hydrogen. In still further alternate embodiments of the SMA, x and y are each 1, each of $R_1$, $R_3$, $R_4$ and $R_5$ are hydrogen atoms, and $R_2$ is an $NH_2$ or NHR, where R is an alkyl or aromatic group; or, alternatively, one of $R_1$ or $R_4$ is a halide, a hydroxyl or a thiol and one of $R_3$ or $R_5$ is a hydrogen atom.

In alternate embodiments of the SMA, x+y is at least 2, x+y is at least 3, and x+y ranges from 1 to 6.

In alternate embodiments of the SMA, hydroxyls of the phenyl moiety are positioned at the 3 and 4 positions of the phenyl group relative to the side chain.

In a second embodiment, the invention relates to a method of modifying a substrate surface to provide a desired functionality, the method comprising contacting at least a portion of the substrate surface with an alkaline, aqueous solution under oxidative conditions, the solution comprising a SMA according to Formula I:

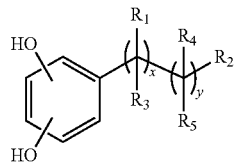

wherein each of $R_1$, $R_2$, $R_3$, $R_4$ and $R_5$ is independently selected from the group consisting of a thiol, a primary amine, a secondary amine, a nitrile, an aldehyde, an imidazole, an azide, a halide, a polyhexamethylene dithiocarbonate, a hydrogen, a hydroxyl, a carboxylic acid, an aldehyde, a carboxylic ester or a carboxamide, provided at least one of $R_1$, $R_2$, $R_3$, $R_4$ and $R_5$ is not a hydrogen atom; wherein x ranges from 0 to 10 and wherein y ranges from 0 to 10, provided that x or y is at least 1; wherein the substrate surface is modified; and contacting the surface-modified substrate with a reactive moiety, wherein the reactive moiety reacts with and is bound to the modified surface. The reactive moiety comprises nucleophiles or metals.

In a third embodiment, the invention provides a method of reducing amounts of metal in a fluid comprising the steps of contacting at least a portion of a substrate with an alkaline, aqueous solution under oxidative conditions, the solution comprising a SMA according to Formula I:

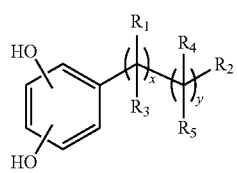

wherein each of $R_1$, $R_2$, $R_3$, $R_4$ and $R_5$ is independently selected from the group consisting of a thiol, a primary amine, a secondary amine, a nitrile, an aldehyde, an imidazole, an azide, a halide, a polyhexamethylene dithiocarbonate, a hydrogen, a hydroxyl, a carboxylic acid, an aldehyde, a carboxylic ester or a carboxamide, provided at least one of $R_1$, $R_2$, $R_3$, $R_4$ and $R_5$ is not a hydrogen atom; wherein x ranges from 0 to 10 and wherein y ranges from 0 to 10, provided that x or y is at least 1; contacting the surface-modified substrate with a reactive moiety, wherein the reactive moiety reacts with and is bound to the modified surface; and positioning the surface in a fluid with metal, whereby the modified surface binds at least a portion of the metal and wherein the reactive moiety is a metal.

In a fourth embodiment, the invention provides a method of modifying a substrate surface to form a biofouling-resistant, modified substrate surface, the method comprising the steps of contacting at least a portion of the surface of the substrate surface with an alkaline solution under oxidative conditions, the solution comprising a SMA according to Formula I:

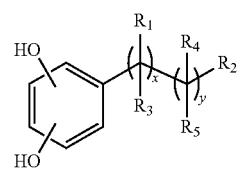

wherein each of $R_1$, $R_2$, $R_3$, $R_4$ and $R_5$ is independently selected from the group consisting of a thiol, a primary amine, a secondary amine, a nitrile, an aldehyde, an imidazole, an azide, a halide, a polyhexamethylene dithiocarbonate, a hydrogen, a hydroxyl, a carboxylic acid, an aldehyde, a carboxylic ester or a carboxamide, provided at least one of $R_1$, $R_2$, $R_3$, $R_4$ and $R_5$ is not a hydrogen atom; wherein x ranges from 0 to 10 and wherein y ranges from 0 to 10, provided that x or y is at least 1; and contacting at least a portion of the surface-modified substrate with a biofouling-resistant reactive moiety, wherein a biofouling-resistant, surface-modified substrate is formed. In one embodiment, the surface-modified substrate is part of a medical device, and the biofouling-resistant reactive moiety is selected from the group consisting of thiols, primary amines, secondary amines, nitrites, aldehydes, imidazoles, azides, halides, polyhexamethylene dithiocarbonate, hydrogen, hydroxyls, carboxylic acids, aldehydes, carboxylic esters or carboxamides.

In a fifth embodiment, the invention provides a kit for modifying a substrate surface, the kit comprising a SMA according to Formula I:

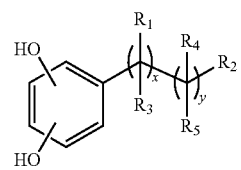

wherein each of $R_1$, $R_2$, $R_3$, $R_4$ and $R_5$ is independently selected from the group consisting of a thiol, a primary amine, a secondary amine, a nitrile, an aldehyde, an imidazole, an azide, a halide, a polyhexamethylene dithiocarbonate, a hydrogen, a hydroxyl, a carboxylic acid, an aldehyde, a carboxylic ester or a carboxamide, provided at least one of $R_1$, $R_2$, $R_3$, $R_4$ and $R_5$ is not a hydrogen atom; wherein x ranges from 0 to 10 and wherein y ranges from 0 to 10, provided that x or y is at least 1; and instructions for use. The surface-modifying agent may be in solution or in powdered form.

The kit may further comprise a reactive moiety selected from the group consisting of thiols, primary amines, secondary amines, nitriles, aldehydes, imidazoles, azides, halides, polyhexamethylene dithiocarbonate, hydrogen, hydroxyls, carboxylic acids, aldehydes, carboxylic esters or carboxamides and a substrate surface to be modified.

In the specification and in the claims, the terms "including" and "comprising" are open-ended terms and should be interpreted to mean "including, but not limited to . . . ." These terms encompass the more restrictive terms "consisting essentially of" and "consisting of"

BRIEF DESCRIPTION OF THE FIGURES

FIG. 1A. Photograph of a mussel attached to commercial polytetrafluoroethylene (PTFE). FIGS. 1B and C. Schematic illustrations of the interfacial location of Mefp-5 and a simplified molecular representation of characteristic amine and catechol groups. FIG. 1D. The amino acid sequence of Mefp-5. FIG. 1E. Amine and catechol functional groups of dopamine. FIG. 1F. Schematic illustration of thin film deposition of polydopamine by dip-coating an object in an alkaline dopamine solution. FIG. 1G. Thickness evolution of polydopamine coating on Si as measured by AFM of patterned substrates. FIG. 1H. XPS characterization of twenty-five different polydopamine-coated substrates. The bar graph represents the intensity of characteristic substrate signal before (hatched) and after (filled) coating by polydopamine. The intensity of the unmodified substrate signal is in each case normalized to 100%. Substrates with characteristic XPS signals indistinguishable from polydopamine are marked by N.A. The circles represent the nitrogen-to-carbon ratio (N/C) after polydopamine coating.

FIG. 5. Time of flight secondary ion mass spectrometry (ToF-SIMS) analysis of polydopainine coating, suggested reaction, and organic ad-layer formation mechanisms.

FIG. 6A. The thickness evolution of a polydopamine-coated substrate as a function of dopamine coating time. Topological images of atomic force microscopy (AFM) measured a height difference between substrate (silicon) and the polydopamine-coated layer generated by photolithography. The bottom inset is 3D representation of actual AFM imaging of a 34 nanometers (nm) coating (6 hours (hr)). The top inset is the cross-section of a 19 nm polydopamine-coating (3 hr). FIG. 6B. ToF-SIMS on the polydopamine-coated substrate. The mass 445 m/z is the product of a fragmented polydopamine chain showing a trimer of 5,6-dihydroxlindole and leukodopaminechrome resulting from dopamine oxidation (refer to FIG. 12). The dehydroxylation ($\alpha$) followed by phenyl ring opening ($\beta$) indicates that a catechol moiety is the major component in the SMA-treated substrate.

FIGS. 7A-C. Electroless copper deposition on polydopamine-coated nitrocellulose film (FIG. 7A); coin (FIG. 7B); and three-dimensional plastic object (FIG. 7C). FIG. 7D. Schematic representation of electroless metallization of photoresist-patterned polydopamine-coated substrates. Photoresist was removed before silver metallization (left) or after copper metallization (right). FIGS. 7E and F. Scanning Electron Microscopy (SEM) images showing micropatterns of silver on Si (FIG. 7E) and copper on a glass substrate (FIG. 7F).

FIG. 8. XPS and ToF SIMS characterization of silver ad-layer deposited on polydopamine-coated substrates by electroless metallization.

FIG. 12A. Total internal reflection fluorescence (TIRF) microscope images of a protein adsorption at a single molecule level. Significant amount of the surface adsorption of fluorophore-labeled proteins onto the unmodified glass surface was shown after 30 min (top). Protein adsorption resistance by PEG (mPEG-$NH_2$, 5 kDa) conjugated on polydopamine-coated glass substrates after continuous 30 min (middle left) and 48 hr (middle right) exposure to proteins. A proposed description of the surface chemistry for the protein inert substrates preparation (top schematic). Positive control experiments (bottom). Glass substrates were PEGylated by the standard silane chemistry and subsequent exposure to protein solutions for 30 min (bottom left) and 48 hr (bottom right) showing a defective surface. FIG. 12B. In vitro antifouling evaluation of various substrates (hatch). Short-term (4 hr) fibroblast adhesion test revealed significantly improved antifouling properties for all tested materials including oxides, metals, semiconductors, and polymers (solid). FIG. 12C. The XPS sulfur 2p (163 eV) signals on the polydopamine-coated glass substrate indicates successful interfacial PEG immobilization. Inset shows the high-resolution spectrum of the sulfur 2p region marked by the arrow in a survey scan.

FIG. 13A. Schematic illustration of alkanethiol monolayer (top right) and PEG polymer (bottom right) grafted on polydopamine-coated substrates. FIG. 13B. Pictures of water droplets on several unmodified (left), polydopamine-coated (middle), and alkanethiol-grafted substrates (right). Substrates investigated include organic polymers (PTFE, PC, and nitrocellulose (NC)), metal oxides ($SiO_2$ and $TiO_2$), and noble metals (Cu and Au). Contact angle values are shown in Table 3. FIG. 13C. NIH 3T3 fibroblast cell adhesion to unmodified glass and OEG6-terminated alkanethiol monolayer formed on polydopamine-coated glass. FIG. 13D-F. TIRF microscopy of Cy3 conjugated Enigma homolog protein adsorption to mPEG-$NH_2$-grafted polydopamine-coated glass (48 hr exposure to protein solution) (FIG. 13D), bare glass (30 min exposure) (FIG. 13E), and mPEG-silane immobilized on bare glass (48 hr exposure) (FIG. 13F). FIG. 13G. NIH 3T3 fibroblast cell adhesion to polydopamine-coated substrates after grafting with mPEG-SH (Pre-nornalized data are available in Table 4).

FIG. 16A. Experimental scheme. The polydopamine-coated latex micro-bead was chemically conjugated to an *E. coli* flagella protein which enabled real-time monitoring of rotation of flagellum. FIG. 16B. Real-time images of counterclockwise rotation of single flagellum with a time resolution of 50 msec (starting from upper left). Spatially confined moving traces of the attached bead showed counterclockwise rotation of the flagellum. Notation of flagella rotational direction is opposite to the normal usage: flagellum rotates 'clockwise' from experimenter's point of view in this figure, which should be expressed as 'counterclockwise' rotation in bacterial chemotaxis. The rotational direction is determined from the bacterial point of view.

FIG. 17A. Representative scheme for hyaluronic acid (HA) conjugation to polydopamine-coated substrates. FIG. 17B. Adhesion of M07e cells on polydopamine-coated polystyrene (PS) increases with the HA solution concentration used during grafting. FIG. 17C. Bioactive HA ad-layers were formed on polydopamine-coated glass, tissue-culture PS, and indium tin oxide (ITO), as demonstrated by attachment of M07e cells. Competition with soluble HA (bar at the right end, PS+sol HA) confirmed that cell adhesion was due to grafted HA. FIG. 17D-F. Polydopamine-modified PS grafted with HA (0.5 mg/mL) retains bioactivity during long-term culture with M07e cells. Images taken after normal-force centrifugation show almost 100% attachment of expanding M07e cells at days 2 (FIG. 17D; 2760±390 cells/$cm^2$) and 4 (FIG. 17E; 5940±660 cells/$cm^2$). In the absence of HA, the polydopamine-coated substrates supported similar levels of M07e cell expansion at day 4, but did not support cell adhesion (610±630 cells/$cm^2$) (FIG. 17F).

DETAILED DESCRIPTION OF THE INVENTION

I. In General

Figure 1:
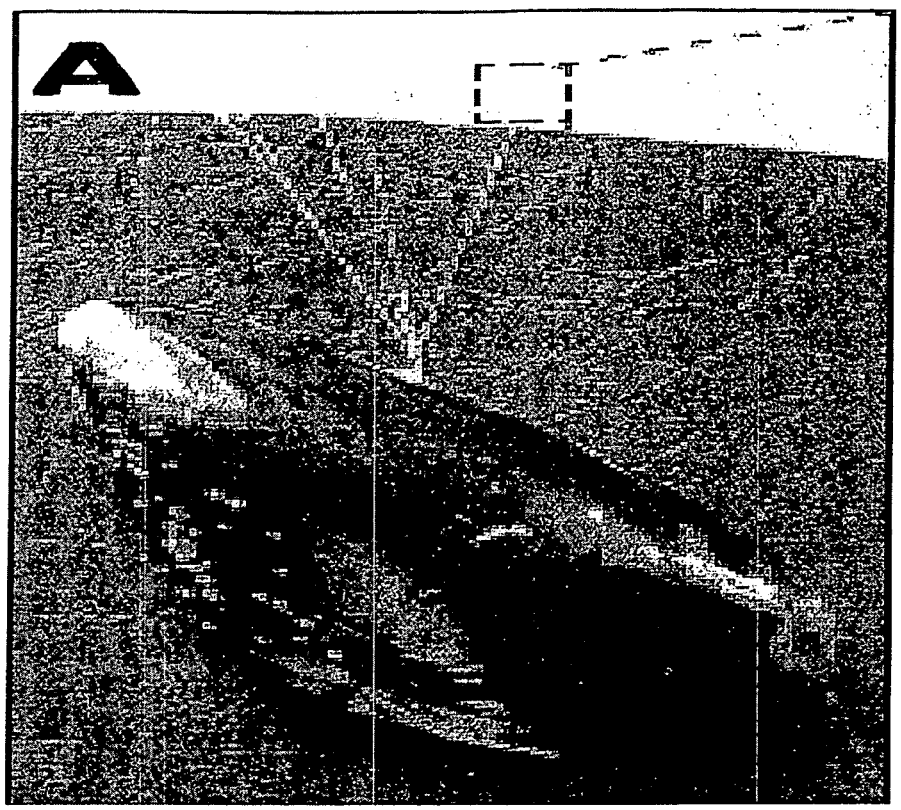
FIG. 1. Mussel-inspired surface-independent adhesive.
Figure 1:
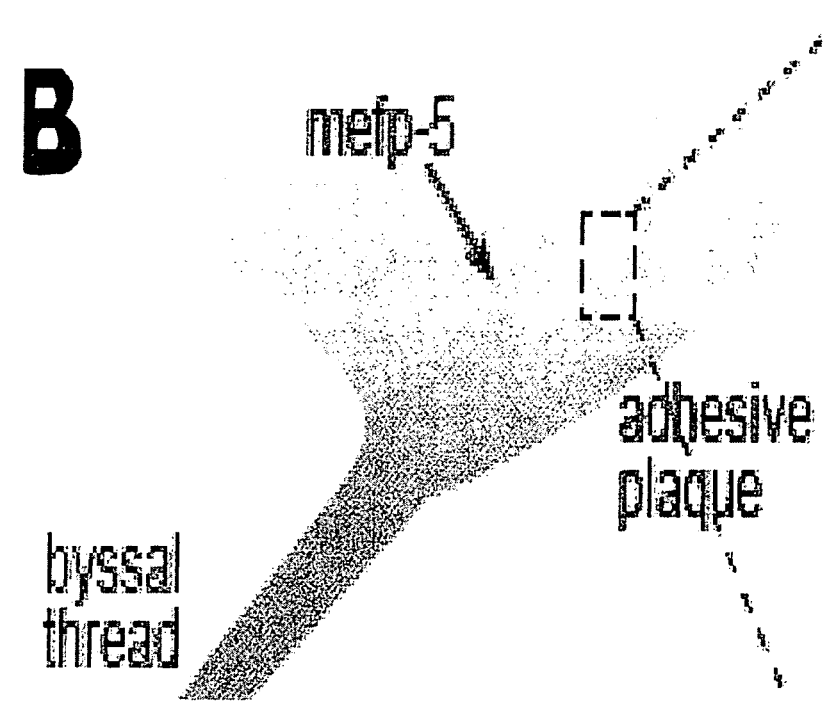
Figure 1:
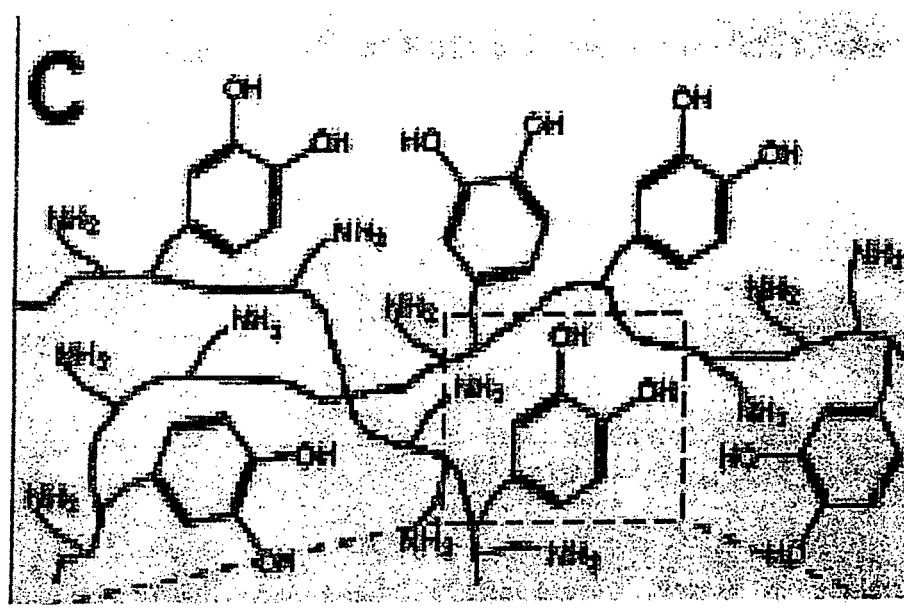
Figure 1:
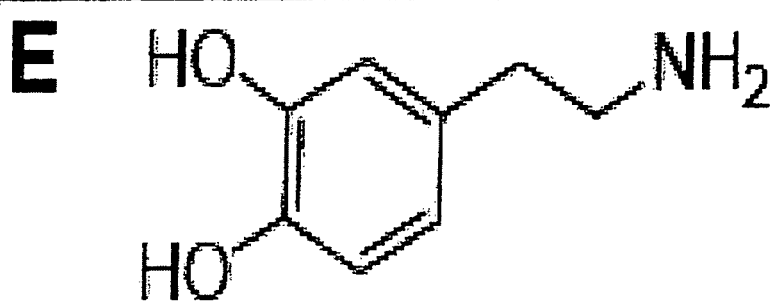
Figure 1:
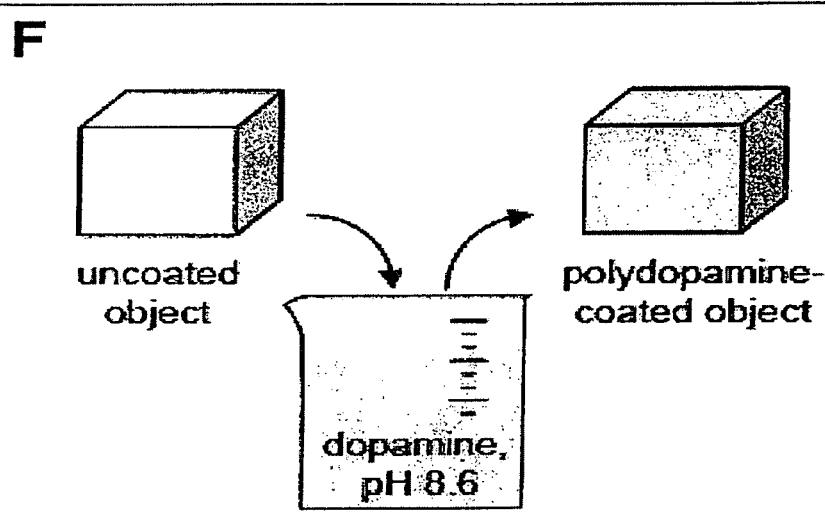
Figure 1:
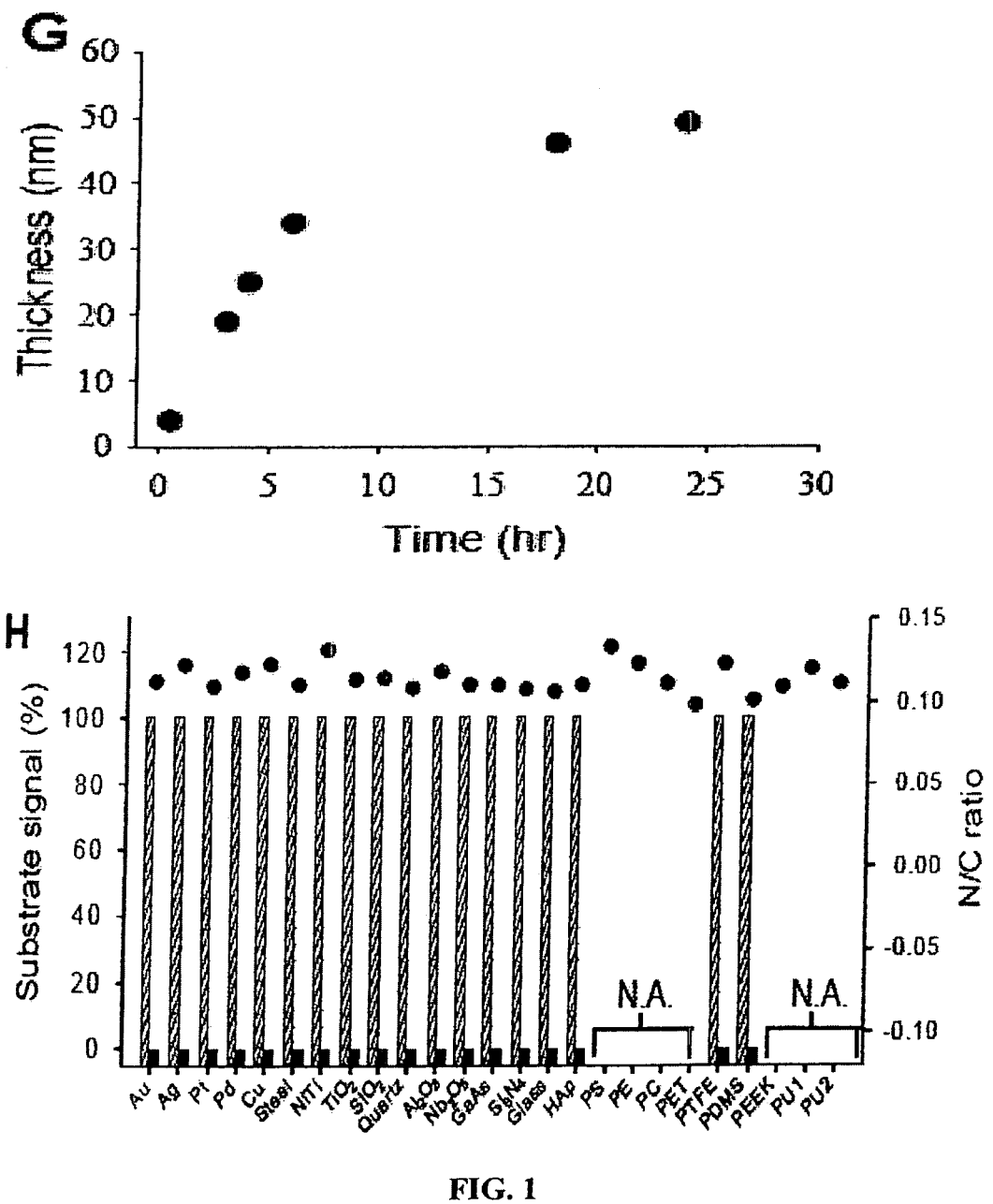

The present invention provides a novel, surface-independent, surface-modification method whereby substrates of all kinds are modified to support at least one functional ad-layer on the substrate's surface. In general, the method comprises contacting at least a portion of the substrate with a surface-modifying agent (SMA) to provide a surface modified to support at least one reactive moiety. The present invention's interfacial chemistry will be useful in important fields including biocompatible coatings of medical devices, surface modifications of drug delivery carriers and tissue engineering scaffolds, biosensors, biofouling-resistant, industrial and consumer coatings, semiconductors, metal removal, surface catalysts and next generation electronic displays.

The method comprises contacting at least a portion of a substrate with an alkaline solution under oxidizing conditions, the solution comprising a SMA according to Formula I:

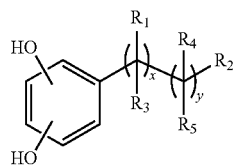

wherein each of $R_1$, $R_2$, $R_3$, $R_4$ and $R_5$ is independently selected from the group consisting of a thiol a primary amine, a secondary amine, a nitrile, an aldehyde, an imidazole, an azide, a halide, a polyhexamethylene dithiocarbonate, a hydrogen, a hydroxyl, a carboxylic acid, an aldehyde, a carboxylic ester or a carboxamide, provided at least one of $R_1$, $R_2$, $R_3$, $R_4$ and $R_5$ is not a hydrogen atom; wherein x ranges from 0 to 10 and wherein y ranges from 0 to 10, provided that x or y is at least 1; and wherein the substrate surface is modified.

After contact with the Formula I solution, the substrate surface is modified. In a preferred embodiment the substrate surface is modified to comprise a polymeric coating. The SMA-treated surface may then be contacted with a reactive moiety to provide a SMA-treated surface having a functional ad-layer. The ad-layer can be tailored for specific applications and may include one or more ad-layers. For instance, in one embodiment, the SMA-treated surface may be modified to provide an ad-layer comprising at least one reactive moiety such as metals, nucleophiles and polymers.

The following paragraphs enumerated consecutively from 1 through 31 provide for various aspects of the present invention. In one embodiment, in a first paragraph (1), the present invention pertains to a method of modifying a substrate surface, the method comprising contacting at least a portion of the substrate with in alkaline solution under oxidative conditions, the solution comprising a SMA according to Formula I:

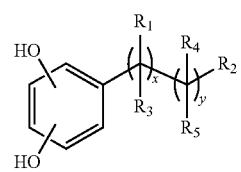

wherein each of $R_1$, $R_2$, $R_3$, $R_4$ and $R_5$ is independently selected from the group consisting of a thiol, a primary amine, a secondary amine, a nitrile, an aldehyde, an imidazole, an azide, a halide, a polyhexamethylene dithiocarbonate, a hydrogen, a hydroxyl, a carboxylic acid, an aldehyde, a carboxylic ester or a carboxamide, provided at least one of $R_1$, $R_2$, $R_3$, $R_4$ and $R_5$ is not a hydrogen atom; wherein x ranges from 0 to 10; wherein y ranges from 0 to 10, provided that x or y is at least 1; and wherein the substrate surface is modified.

In a second paragraph (2), the invention relates to the method of paragraph 1, wherein x and y are both 1, and where $R_1$ and $R_4$ form a double bond when eliminated.

In a third paragraph (3), the invention relates to the method of either of paragraphs 1 or 2, wherein $R_2$ is $NH_2$ or NHR, wherein R is an alkyl or aromatic group.

In a fourth paragraph (4), the invention relates to the method of any of paragraphs 1 through 3, wherein one of $R_1$ or $R_4$ is a halide, a hydroxyl or a thiol and one of $R_3$ or $R_5$ is a hydrogen atom.

In a fifth paragraph (5), the invention relates to the method of paragraph 1, wherein x is 1, y is 1, $R_1$ is a hydroxyl and $R_3$, $R_4$ and $R_5$ are a hydrogen.

In a sixth paragraph (6), the invention relates to the method of paragraphs 4 and 5, wherein $R_2$ is a $NH_2$.

In a seventh paragraph (7), the invention relates to the method of paragraph 1, wherein x and y are each 1 and each of $R_1$, $R_3$, $R_4$ and $R_5$ are hydrogen atoms.

In an eighth paragraph (8), the invention relates to the method of paragraph 7, wherein $R_2$ is $NH_2$ In a ninth paragraph (9), the invention relates to the method of paragraph 1, wherein $R_2$ is $NH_2$ or NHR, wherein R is an alkyl or aromatic group In a tenth paragraph (10), the invention relates to the method of any of paragraphs 1 through 9 wherein one of $R_1$ or $R_4$ is a halide, a hydroxyl or a thiol and one of $R_3$ or $R_5$ is a hydrogen atom.

In an eleventh paragraph (11), the invention relates to the method of either of paragraphs 9 or 10, wherein $R_2$ is an amine.

In a twelfth paragraph (12), the invention relates to the method of any of paragraphs 1 through 11, wherein x+y is at least 2.

In a thirteenth paragraph (13), the invention relates to the method of any of paragraphs 1 through 12, wherein x+y is at least 3.

In a fourteenth paragraph (14), the invention relates to the method of any of paragraphs 1 through 13 wherein the hydroxyls of the phenyl moiety are positioned at the 3 and 4 positions of the phenyl group relative to the side chain.

In a fifteenth paragraph (15), the invention relates to the method of any of paragraphs 1 through 14, wherein Formula I forms a polymeric coat on the substrate surface.

In a sixteenth paragraph (16), the invention relates to the method of paragraph 1 wherein the surface-modifying agent is selected from the group consisting of 3,4-dihydroxy-L-phenylalanine (DOPA), 3,4-dihydroxyphenylalanine methyl ester, dopamine, norepinephrine, epinephrine and salts thereof.

In a seventeenth paragraph (17), the invention relates to the method of any of paragraphs 1 through 16 wherein the solution is aqueous.

In an eighteenth paragraph (18), the invention relates to the method of any of paragraphs 1 through 17 wherein x+y ranges from 1 to 6.

In a nineteenth paragraph (19), the invention relates to a method of modifying a substrate surface to provide a desired functionality, the method comprising contacting at least a portion of the substrate surface with an alkaline, aqueous solution under oxidative conditions, the solution comprising a surface-modifying agent according to Formula I:

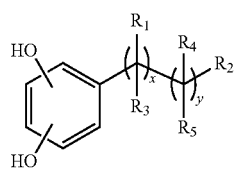

wherein each of $R_1$, $R_2$, $R_3$, $R_4$ and $R_5$ is independently selected from the group consisting of a thiol, a primary amine, a secondary amine, a nitrile, an aldehyde, an imidazole, an azide, a halide, a polyhexamethylene dithiocarbonate, a hydrogen, a hydroxyl, a carboxylic acid, an aldehyde, a carboxylic ester or a carboxamide, provided at least one of $R_1$, $R_2$, $R_3$, $R_4$ and $R_5$ is not a hydrogen atom; wherein x ranges from 0 to 10 and wherein y ranges from 0 to 10, provided that x or y is at least 1; and wherein the substrate surface is modified; and contacting the surface-modified substrate with a reactive moiety, wherein the reactive moiety reacts with and is bound to the modified surface.

In a twentieth paragraph (20), the invention relates to the method of paragraph 19, wherein the reactive moiety comprises a nucleophile.

In a twenty-first paragraph (21), the invention relates to the method of paragraph 19 wherein the reactive moiety comprises a metal.

In a twenty-second paragraph (22), the invention relates to a method of reducing amounts of metal in a fluid comprising the steps of contacting at least a portion of a substrate with an alkaline, aqueous solution under oxidative conditions, the solution comprising a SMA according to Formula I:

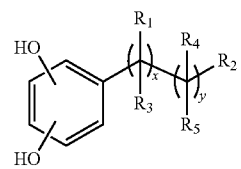

wherein each of $R_1$, $R_2$, $R_3$, $R_4$ and $R_5$ is independently selected from the group consisting of a thiol, a primary amine, a secondary amine, a nitrile, an aldehyde, an imidazole, an azide, a halide, a polyhexamethylene dithiocarbonate, a hydrogen, a hydroxyl, a carboxylic acid, an aldehyde, a carboxylic ester or a carboxamide, provided at least one of $R_1$, $R_2$, $R_3$, $R_4$ and $R_5$ is not a hydrogen atom; wherein x ranges from 0 to 10 and wherein y ranges from 0 to 10, provided that x or y is at least 1; contacting the surface-modified substrate with a reactive moiety, wherein the reactive moiety reacts with and is bound to the modified surface; and positioning the surface in a fluid with metal, whereby the modified surface binds at least a portion of the metal.

In a twenty-third paragraph (23), the invention relates to the method of paragraph 22 wherein the reactive moiety is a metal.

In a twenty-fourth paragraph (24), the invention relates to a method of modifying a substrate surface to form a biofouling-resistant, modified substrate, the method comprising the steps of contacting at least a portion of the substrate surface with an alkaline solution under oxidative conditions, the solution comprising a SMA according to Formula I:

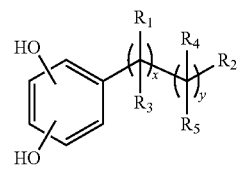

wherein each of $R_1$, $R_2$, $R_3$, $R_4$ and $R_5$ is independently selected from the group consisting of a thiol, a primary amine, a secondary amine, a nitrile, an aldehyde, an imidazole, an azide, a halide, a polyhexamethylene dithiocarbonate, a hydrogen, a hydroxyl, a carboxylic acid, an aldehyde, a carboxylic ester or a carboxamide, provided at least one of $R_1$, $R_2$, $R_3$, $R_4$ and $R_5$ is not a hydrogen atom; wherein x ranges from 0 to 10 and wherein y ranges from 0 to 10, provided that x or y is at least 1; and contacting at least a portion of the surface-modified substrate with a biofouling-resistant reactive moiety, wherein a biofouling-resistant, modified substrate surface is formed.

In a twenty-fifth paragraph (25), the invention relates to the method of paragraph 24 wherein the biofouling-resistant reactive moiety is selected from the group consisting of thiols, primary amines, secondary amines, nitriles, aldehydes, imidazoles, azides, halides, polyhexamethylene dithiocarbonate, hydrogen, hydroxyls, carboxylic acids, aldehydes, carboxylic esters or carboxamides.

In a twenty-sixth paragraph (26), the invention relates to the method of paragraphs 24 and 25 wherein the modified substrate surface is part of a medical device.

In a twenty-seventh paragraph (27), the invention relates to a kit for modifying a substrate surface, the kit comprising a SMA according to Formula I:

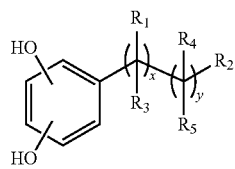

wherein each of $R_1$, $R_2$, $R_3$, $R_4$ and $R_5$ is independently selected from the group consisting of a thiol, a primary amine, a secondary amine, a nitrile, an aldehyde, an imidazole, an azide, a halide, a polyhexamethylene dithiocarbonate, a hydrogen, a hydroxyl, a carboxylic acid, an aldehyde, a carboxylic ester or a carboxamide, provided at least one of $R_1$, $R_2$, $R_3$, $R_4$ and $R_5$ is not a hydrogen atom; wherein x ranges from 0 to 10 and wherein y ranges from 0 to 10, provided that x or y is at least 1; and instructions for use.

In a twenty-eighth paragraph (28), the invention relates to the kit of paragraph 27 further comprising a reactive moiety selected from the group consisting of thiols, primary amines, secondary amines, nitriles, aldehydes, imidazoles, azides, halides, polyhexamethylene dithiocarbonate, hydrogen, hydroxyls, carboxylic acids, aldehydes, carboxylic esters or carboxamides.

In a twenty-ninth paragraph (29), the invention relates to the kit of paragraphs 27 and 28 further comprising a substrate surface to be modified.

In a thirtieth paragraph (30), the invention relates to the kit of paragraphs 27 through 29, wherein the surface-modifying agent is in solution In a thirty-first paragraph (31), the invention relates to the kit of paragraphs 27 through 29, wherein the surface-modifying agent is in powdered form.

These embodiments are described in more detail below.

II. Surface-Modifying Agents (SMAs)

Formula I.

In a preferred embodiment, the substrate surface is modified by contacting at least a portion of the substrate with a dilute, alkaline solution under oxidizing conditions, the solution comprising a SMA according to Formula I:

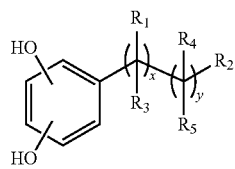

wherein each of $R_1$, $R_2$, $R_3$, $R_4$ and $R_5$ is independently selected from the group consisting of a thiol, a primary amine, a secondary amine, a nitrile, an aldehyde, an imidazole, an azide, a halide, a polyhexamethylene dithiocarbonate, a hydrogen, a hydroxyl, a carboxylic acid, an aldehyde, a carboxylic ester or a carboxamide, provided at least one of $R_1$, $R_2$, $R_3$, $R_4$ and $R_5$ is not a hydrogen atom; wherein x ranges from 0 to 10 and wherein y ranges from 0 to 10, provided that x or y is at least 1; and wherein the substrate surface is modified.

Dopamine.

In another preferred embodiment, the substrate surface is modified by contacting at least a portion of the substrate with a SMA wherein the SMA is dopamine or dopamine salts:

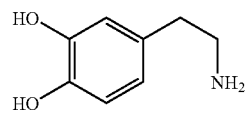

Figure 2A:
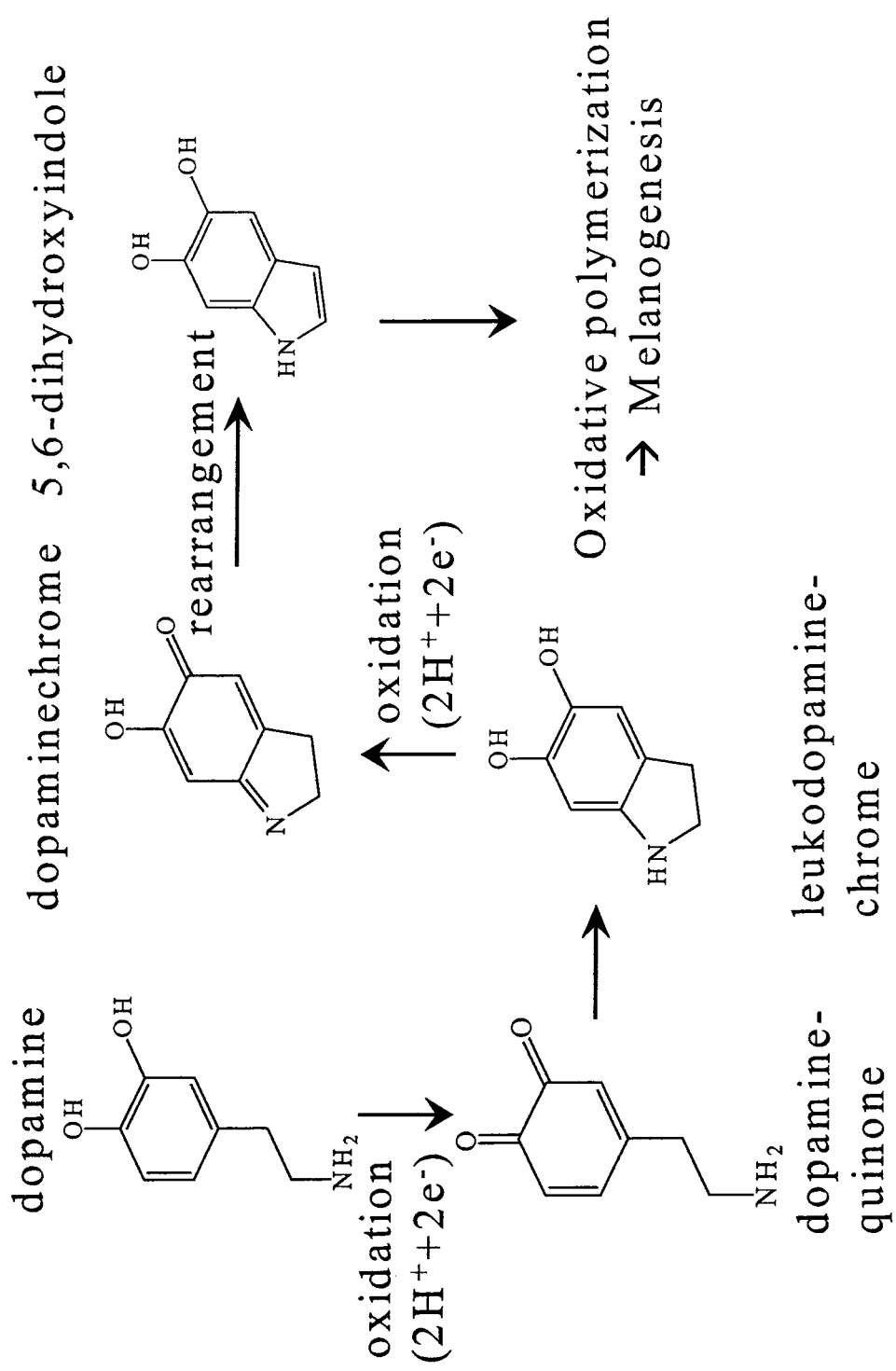
FIG. 2. Reaction schemes I (A) and II (B) of dopamine oxidation.
Figure 2B:
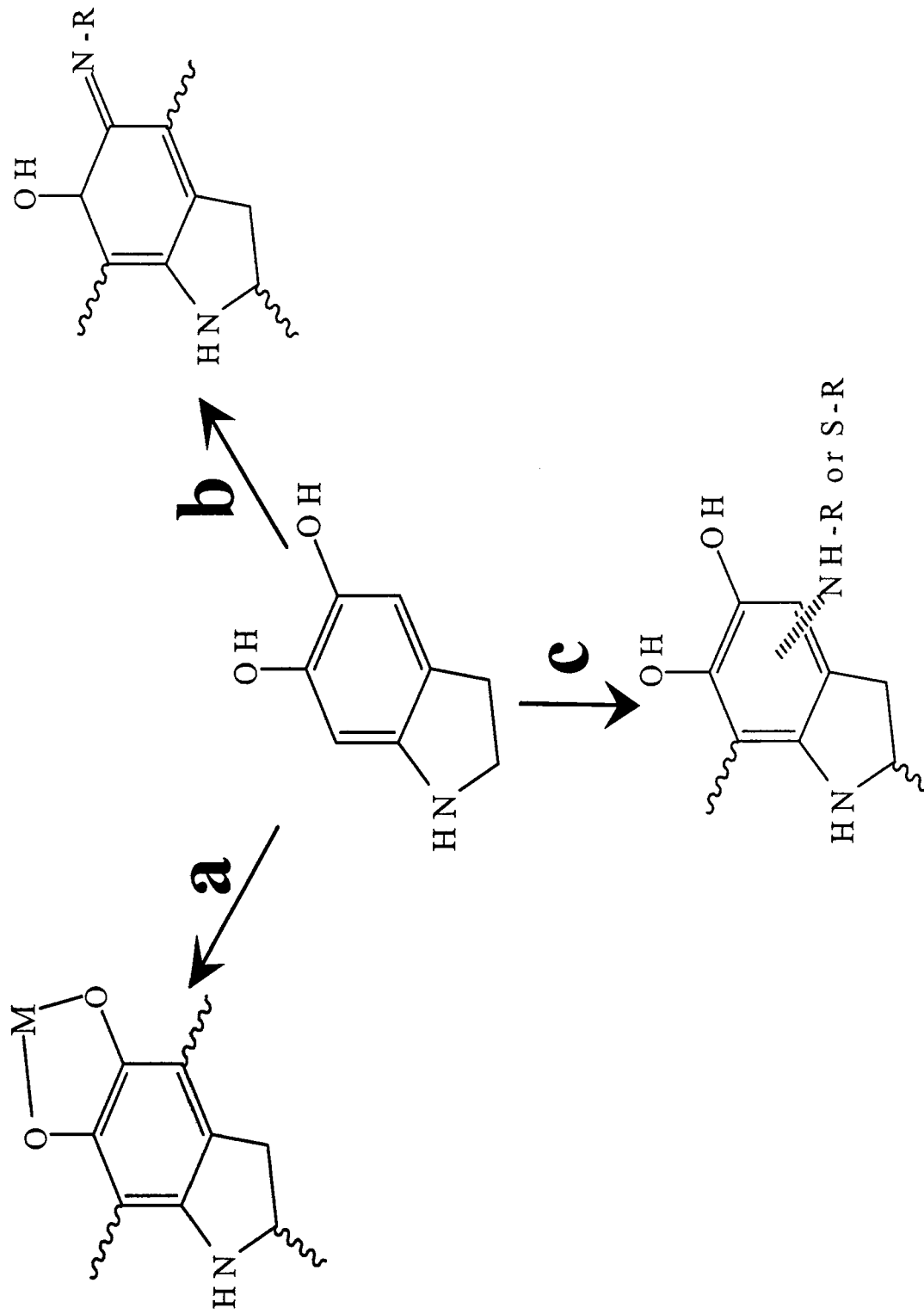

Substrates treated with dopamine are reactive with organic heteroatoms such as amine and thiol groups by Schiff base or Michael addition reactions (pathway "b," "c" reaction sequence II-FIG. 2B) and also strongly binds to various metals such as Fe, Cu, Hg, and Zn (pathway "a" of reaction sequence II-FIG. 2B). Thus our new concept of surface-independent, surface-modifying chemistry emerges: the self-polymerized multilayer nanofilm of dopamine provides multifunctionality due to chemical reactions or metal bindings at a top layer of a solid-liquid or solid-vapor interface whereas the bottom layer is attached to versatile organic and inorganic substrates. These very unique; current interface modifiers require chemical synthesis incorporating chemical orthogonality at each end.

In one preferred embodiment dopamine is used. When a substrate is contacted with dopamine, an adherent polydopamine polymeric film is coated on the substrate. Dopamine oxidation chemistry may be summarized by reaction sequence (I) in FIG. 2A. There, dopamine's dihydroxyl groups are deprotonated under oxidative conditions (neutral or alkaline), becoming dopamine-quinone. Rearrangement results in intra-molecular cyclization which reproduces dihydroxyl groups from quinone.

The second oxidation generates dopamine-chrome which quickly rearranges to form a stable phenyl ring structure creating an additional double bond in the 5-membered ring (5,6-dihydroxyindole). The third oxidation starts inter-molecular cross-linking due to the full unsaturated nature of indole forming polymer both in solution and on the substrate. Norepinephrine.

In another preferred embodiment, the substrate surface is modified by contacting at least a portion of the substrate with a SMA wherein the SMA is norepinephrine or norepinephrine salts:

Norepinephrine is a neurotransmitter found in the brain which has an additional hydroxyl group in the carbon spacer of dopamine.

Other preferred SMAs include 3,4-dihydroxy-L-phenylalanine (DOPA), 3,4-dihydroxy-L-phenylalanine methyl ester, epinephrine and salts thereof.

The alkaline solution of SMA of the present invention can also include additives such as fillers, pigments, wetting agents, viscosity modifiers, stabilizers, anti-oxidants or cross-linking agents. The SMA can be cross-linked if desired. If desired, the SMA solution can include various adjuvants such as small particle fillers, surface active agents, UV absorbers, photo-initiators, colorants and indicators.

The surface-independent, surface-modification method of the present invention comprises contacting at least a portion of the substrate surface with a SMA under oxidative conditions to form a surface-modified substrate surface having at least one reactive moiety on the substrate's surface. The method comprises contacting at least a portion of the substrate with an alkaline solution under oxidizing conditions, the solution comprising a SMA according to Formula I:

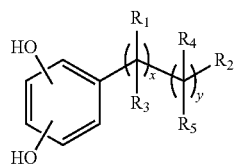

wherein each of $R_1$, $R_2$, $R_3$, $R_4$ and $R_5$ is independently selected from the group consisting of a thiol, a primary amine, a secondary amine, a nitrile, an aldehyde, an imidazole, an azide, a halide, a polyhexamethylene dithiocarbonate, a hydrogen, a hydroxyl, a carboxylic acid, an aldehyde, a carboxylic ester or a carboxamide, provided at least one of $R_1$, $R_2$, $R_3$, $R_4$ and $R_5$ is not a hydrogen atom; wherein x ranges from 0 to 10 and wherein y ranges from 0 to 10, provided that x or y is at least 1; and wherein the substrate surface is modified.

By "dilute," we mean that the concentration of SMA is 0.01 mg/ml-100 mg/ml, preferably ranging from about 0.05 mg/ml or higher.

By "alkaline," we mean that the pH value of the solution ranges from 7.1 to 12, with a preferred pH ranging from 7.5 to 10, with a further preferred pH ranging from 7.5 to 8.5. An alkaline solution triggers polymerization of SMAs onto the substrate surface.

By "solution," we mean both aqueous and non-aqueous solvents, including miscible solutions of water and organic solvents such as acetone, chloroform, dichloromethane, methanol, ethanol, isopropanol, dimethylformamide, dimethylsulfoxide and hexane. Preferably, the solution is made just prior to contacting the substrate, although the solution may be stored for at least brief periods of time before use.

By "under oxidative conditions," we mean alkaline pH of aqueous solutions and non-aqueous solvents with dissolved oxygen or organic bases such as triethylamine. In alternative embodiments, solutions comprising oxidants such as hydrogen peroxide, sodium periodate, tertiary butylhydroperoxide, organic peroxides, quinones including benzoquinones, napthoquinones, anthraquinones, nitroaryl compounds, metal oxidants including $Cu^{2+}$, $Fe^{3+}$, $Co^{3+}$ and $Mn^{3+}$, phenols, indoles, aminobenzenes and more can be used to initiate polymerization via oxidization of the SMA.

By "contacting," we mean exposing at least a portion of the substrate to the SMA for a period of time ranging from 1 minute to 24 hours and a range of temperatures from 0° C. to 100° C.

In a preferred embodiment, the substrate is exposed to the SMA for a period of time ranging from 2 hrs to 18 hrs, preferably for 5 hrs to 15 hrs, even more preferably for 8 hrs to 12 hrs.

In a preferred embodiment the entire substrate is immersed or dipped in the SMA solution. The examples below illustrate preferred contacting methods. However, a variety of techniques can be employed to contact the substrate surface with the SMA solution including, without limitation, swabbing, dip coating, spin coating, die coating, ink jet coating, spraying, screen printing (e.g., rotary screen printing), gravure printing, photolithographic printing and flexographic printing, microcontact printing, nanolithography.

On contact, the substrate surface is preferably modified so as to provide a substrate surface having at least one reactive moiety. In a preferred embodiment, the reactive moiety comprises a smooth, continuous polymeric coating on the substrate surface, the polymeric coating having a substantially constant thickness. As a general guide, the polymeric coating exists on the substrate surface in a thickness ranging from about 1 to 1000 nnm, preferably ranging from about 1 to 100 nm, more preferably ranging from about 5 to 50 nm, and even more preferably ranging from about 10 to 50 nm.

IV. Substrates

The method comprises contacting at least a portion of the substrate with the SMA described above.

By "substrate," we mean any inorganic or organic substrate. For instance, the substrate can be an organic solid, an inorganic solid, or a combination of organic and inorganic solids that provides a surface for receiving the adherent polymer. Suitable organic or inorganic substrates may also be fibrous, filamentous, meshes, porous or solvent-swollen (e.g. hydrogel or organogel) objects. Preferably, care is taken when selecting the substrate so that there will be an adequate degree of adhesion between the substrate and the SMA.

Suitable inorganic substrates include but are not limited to inorganic substrates such as quartz, glass, silica and other oxides or ceramics such as alumina, indium tin oxide, lithium tantalate (LiTaO3), lithium niobate (LiNbO3), gallium arsenide (GaAs), silicon carbide (SiC), langasite (LGS), zinc oxide (ZnO), aluminum nitride (AlN), aluminum oxide ($Al_2O_3$), silicon (Si), silicon nitride (Si3N4), and lead zirconium titanate ("PZT"), titanium oxide ($TiO_2$), niobium oxide ($Nb_2O_5$); and metals or alloys such as aluminum, copper, gold, silver and steel. Other suitable inorganic substrates include, without limitation, mica, diamond and nickel titanium (NiTi).

Suitable organic substrates include but are not limited to organic substrates such as thermoplastics including polyesters (e.g., polyethylene terephthalate or polyethylene naphthalates), polyacrylates (e.g., polymethyl methacrylate or "PMMA"), poly(vinyl acetate) ("PVAC"), poly(vinylbutyral) ("PVB"), poly(ethyl acrylate) ("PEA"), poly(diphenoxyphosphazene) ("PDPP"), polycarbonate ("PC"), polypropylene ("PP"), high density polyethylene ("HDPE"), low density polyethylene ("LDPE"), polysulfone ("PS"), polyether sulfone ("PES"), polyurethane ("PUR"), polyamide ("PA"), poly(dimethylsiloxane) ("PDMS"), polyvinyl chloride ("PVC"), polyvinylidene fluoride ("PVdF"), polystyrene ("PSy") and polyethylene sulfide; and thermoset plastics such as cellulose derivatives, polyimide, polyimide benzoxazole and polybenzoxazole. Other suitable organic substrates include, without limitation, graphite, carbon nanotubes, fullerenes, graphene, poly(glycolic acid), poly(lactic acid), and poly(lactic-co-glycolic acid) and Teflon®.

Untreated Substrates.

The method of the present invention can be used on substrates in any condition (see Examples 2 and 3). For instance, substrates having existing coatings such as paint, oil, grease, protectants and the like can be used without any additional pre-treatments or cleaning.

Pre-treated Substrates.

In another embodiment, the substrate can instead or in addition to be pretreated to enhance surface-modification. Preferred pretreatments include but are not limited to electron and ion beam irradiation, electrical discharge in the presence of a suitable reactive or non-reactive atmosphere (e.g., plasma, glow discharge, corona discharge, dielectric barrier discharge or atmospheric pressure discharge); chemical pretreatment (e.g., with a low solids solution of polyvinylidene dichloride or with a solvent-borne mixture of a polyester resin and an aziridine cross-linker); flame pretreatment; ultraviolet light pretreatment with or without ozone pretreatment; and incorporating functional polymers into the substrate when a polymeric substrate is employed. In an alternative embodiment, the present invention provides a method of enhancing coatings on artificially or naturally damaged/altered substrates.

V. Reactive Moiety

The surface-independent, surface-modifying biocoating of the present invention provides in amazingly versatile platform for secondary reactions, allowing one to tailor specific reactive moieties to substrates for diverse functional uses. For instance, the SMA-treated substrates of the present invention are conformal and chemically reactive with a wide variety of organic and inorganic species such as metal ions, thiols, primary amines, secondary amines, nitriles, aldehydes, imidazoles, azides, halides, polyhexamethylene dithiocarbonate, hydrogen, hydroxyls, carboxylic acids, aldehydes, carboxylic esters or carboxamides. Thus, secondary reactions between the SMA-treated substrates and such reactive moieties can be exploited to impart specific functionalities to the surface-modified substrate.

The oxidative pathways for adding the secondary reactions are set forth in reaction sequence II in FIG. 2B. There, pathway 'a' represents various metal bindings of dopamine. The metal 'M' can be titanium (Ti), iron (Fe), copper (Cu), zinc (Zn), silver (Ag), or many others. Pathway 'b' is Schiff base and 'c' is Michael addition reactions which were used for the interfacial reactions with PEG-amine, PEG-thiol, and proteins (flagella).

Current applications for SMA-treated substrates having a reactive moiety are many and include, without limitation, applications for anti-biofouling surfaces; medical devices for catheters, stents, artificial bones, teeth, and dialysis tubes; semiconductors for bio-MEMS, and sensors; and metal nanoparticles and quantum dots for sensors, diagnostics, and cellular imaging.

Thus, in an alternate embodiment of the invention, a method of applying a reactive moiety to a SMA-treated substrate is provided. The method comprises contacting at least a portion of a substrate with an alkaline solution under oxidizing conditions, the solution comprising a SMA to form a substrate having a modified surface and then contacting the SMA-treated substrate with a reactive moiety to form a functional ad-layer on the SMA-treated substrate.

By "reactive moiety" we mean to include any reactive moiety including metals, nucleophiles and polymers. Specifically, we include thiols, primary amines, secondary amines, nitrites, aldehydes, imidazoles, azides, halides, polyhexamethylene dithiocarbonate, hydrogen, hydroxyls, carboxylic acids, aldehydes, carboxylic esters or carboxamides.

By "ad-layer" we mean an additional layer of reactive compounds which binds to the modified surface of the SMA-treated substrate and alters the functionality of the substrate.

Electroless Metallization.

In this embodiment, one would preferably treat a surface with an SMA as described above and then expose the treated surface to metal solutions to form an adherent metal film. Example 5, below, describes the dip-coating of an SMA-treated substrate in a silver nitrate and copper (II) chloride solution. In general, one would wish to expose the SMA-treated substrate to a solution of 10-500 mM metal, pH 3-8, and 20-70° C.

Nucleophile Addition.

In this embodiment, one would preferably contact a substrate with an SMA as described above and then expose the SMA-treated substrate to nucleophile. By "nucleophile" we mean an electron-rich species with a tendency to be attracted to the nuclear charge of an electron-poor species, the electrophile. Important nucleophiles include primary and secondary amines, thiols, azides, nitrites, aldehydes, imidazoles, azides, polyhexamethylene dithiocarbonate, hydrogen, hydroxyls, carboxylic acids, aldehydes, carboxylic esters or carboxamides, etc.

A partial list of important nucleophiles can be seen in Table 1:

TABLE 1

| $Cl^-$ | $Br^-$ | $I^-$ | |
| | $HO^-$ | $*R-OH$ | $*RO^-$ |
| $H_2S$ | $HS^-$ | $*R-SH$ | $*R-S^-$ |
| $-NH_2$ | $N_3^-$ | $^-C \equiv N$ | $*R-C \equiv C^-$ |

*R can be anything.

Suitable nucleophiles may comprise parts of more complex molecules, such as proteins or nucleic acids. For instance, Example 9 describes labeling surfaces with flagella. Example 10 describes fibroblast adhesion to surfaces, Example 11 describes adding hyaluronic acid to surfaces and Example 13 describes addition of histidine to surfaces. In general, macromolecules containing the nucleophiles described above react to SMA-treated substrates.

Polymer Grafting.

In this embodiment, one would preferably contact a substrate with an SMA as described above and then expose the SMA-treated substrate to polymers including any synthetic polymers that contain nucleophiles as described above. For example, in the case of poly(ethylene glycol) (PEG), $NH_2-$PEG-$NH_2$, methoxy-PEG-$NH_2$, methoxy-PEG-SH, SH-PEG-SH, branched-PEG-NH2, and branched-PEG-SH are the polymer structures reacting to SMA-treated surfaces. For instance, Example 8 describes grafting PEG to SMA-treated surfaces. However, alternative forms of polymeric grafting are also envisioned, including free radical graft polymerization, atom-transfer radical polymerization, plasma polymerization/deposition, plasma treatment and surface irradiation, and cationic and anionic monomer or oligomer additions.

Metal Scavenging.

In this embodiment, the amount of metal ions in a fluid can be reduced by binding to SMA-treated substrates. By "reducing" we mean any reduction in the amount of metal ions in solution, preferably to below maximum contaminant levels (MCL) or other established benchmarks for all metals. The method comprises contacting at least a portion of a substrate with an alkaline, aqueous solution comprising Formula I. One then positions the surface-modified substrate in a solution with metal, whereby the surface-modified substrate reduces the amount of metal in the solution. The method can be performed in either flow-through or batch mode. See Example 12 below for a preferred example.

VI. Kits

In an alternate embodiment of the invention, a kit for modifying a substrate's surface is provided. In one embodiment, the kit comprises a dilute, alkaline solution comprising a SMA according to Formula I, and, optionally, a substrate to be modified, and instructions for use. In a preferred embodiment, the kit comprises a powdered form of at least one SMA, wherein the powdered SMA is hydrated by the user and for immediate contacting with the substrate. For example, dopamine powder can be provided for dissolving in a provided alkaline solution.

In an alternate embodiment, the kit comprises an SMA formulated, delivered and stored as a liquid in a nonoxidizing condition, for example at a low pH. In this case the user would neutralize the liquid SMA to pH>7 for subsequent contacting with the substrate. For example, dopamine dissolved in acidic water can be provided for users to add base (NaOH) and substrates for coating.

In another alternative embodiment, a reactive moiety is also included, wherein a user can modify the SMA-treated substrate to include a reactive moiety.

By "substrate" we mean any substrate described above, including any substrate wherein having at least one reactive moiety on the surface would be useful.

By "instructions for use" we mean a publication, a recording, a diagram, or any other medium of expression which is used to communicate the usefulness of the invention for one of the purposes set forth herein. The instructional material of the kit can, for example, be affixed to a container which contains the present invention or be shipped together with a container which contains the invention. Alternatively, the instructional material can be shipped separately from the container or provided on an electronically accessible form on a internet website with the intention that the instructional material and the SMA solution and substrate be used cooperatively by the recipient.

VII. Applications for SMA-Treated Substrates

Photolithography.

SMA-treated substrates can be used for subsequent photolithography micropatterning and photoresist etching. Photolithography is a process used to selectively apply very precise geometric patterns onto substrates. Typically only very clean, flat substrates can be used for photolithography. However, SMA-treated substrates allow virtually any substrate to be modified for use with photolithography, greatly expanding the types of materials which can be used in applications requiring very small, very precise patterns including drug delivery carriers, micro- and nano-wires for photonics, peptide arrays, protein arrays, oligonucleotide arrays, electronic circuitry and integrated electronic chips, electronic displays and the like.

SMA-Assisted Electroless Metallization.

SMA-treated substrates can be used to accept adherent and uniform metal coatings by electroless metallization. Metals are often used as synthetic catalysts for chemical reactions with accelerated turn-over rates, such as platinum catalysts used to facilitate reactions of aromatic conversion or branched isomers from straight alkane chains. Copper layers on substrates such as metals, semiconductors, and polymers are important for various electronic and packaging technologies, particularly in copper deposition on synthetic organic substrates for flexible printed circuit, electromagnetic interference shielding of display panels, and multichip module packing. However, current approaches can be applied for only one or a few types of substrates and often involve complicated multi-step procedures. The present invention therefore describes a method of modifying the surface of any substrate to include a metal coating for use as, among other things, synthetic catalysts, semiconductors, display panels, surface-metallization of cantilever- or beam-based sensor devices, and carbon nanotubes.

Further, SMA-treated substrates can be used to accept electroless metal deposition combined with conventional lithography processes to yield micropatterned metal-deposition on SMA-treated substrates. This provides an aqueous, cost-effective and surface-independent preparation process that does not require toxic Pd/Sn colloids for catalysis, yielding substrates useful in, for example, electronic circuit fabrication.

Biofouling-Resistance.

SMA-treated substrates can be used to provide biofouling-resistant substrates for use in medical and dental devices and implants, watercraft hulls, off-shore and on-shore structures of manmade or natural composition, water treatment facilities, liquid handling or movement structures such as pipelines and chemical treatment facilities, food processing surfaces, and construction and housing materials. By "biofouling" we mean the nonspecific adsorptions of macromolecules, cells, proteins, bacteria, algae and other organisms and their byproducts at solid-liquid or solid-air interfaces, often resulting in adverse effects on performance, safety, and longevity of, for instance, medical devices and sensors. By "resistant" we mean substrates modified so as to prevent the nonspecific adsorptions of macromolecules, cells, proteins, bacteria, algae and other organisms and their byproducts at solid-liquid or solid-air interfaces associated with biofouling. Currently, surface immobilization of polyethylene glycol (PEG or PEGylation) has been the most popular approach for nonfouling surface preparation, but anchoring PEG molecules in a surface independent manner remains a major challenge.

Biosensors.

SMA-treated substrates can be used to immobilize proteins and DNA on substrates for use in diagnosis, therapy of disease and experimental tools for research in tissue and cellular proteomics and genomics. Immobilizing proteins and DNAs on substrates has revolutionized throughput of medical diagnostics and biological research for library screening and gene expressions. So called protein and DNA chips require chemical conjugations of biomacromolecules (DNA and proteins) onto substrates. Glass has dominated in this area due to its optical transparency and low cost. However, efforts have been made to develop bioconjugate chemistry onto portable substrates such as paper for convenient diagnostic purposes. Thus the versatile SMA-treated substrates and method thereof presented herein can be applied to develop portable diagnostic kits including biosensors, functional genomics, proteomics, and metabolomics, or hospital/clinic-base diagnostic devices or their components.

Self-Assembled Monolayers.

Figure 5A:
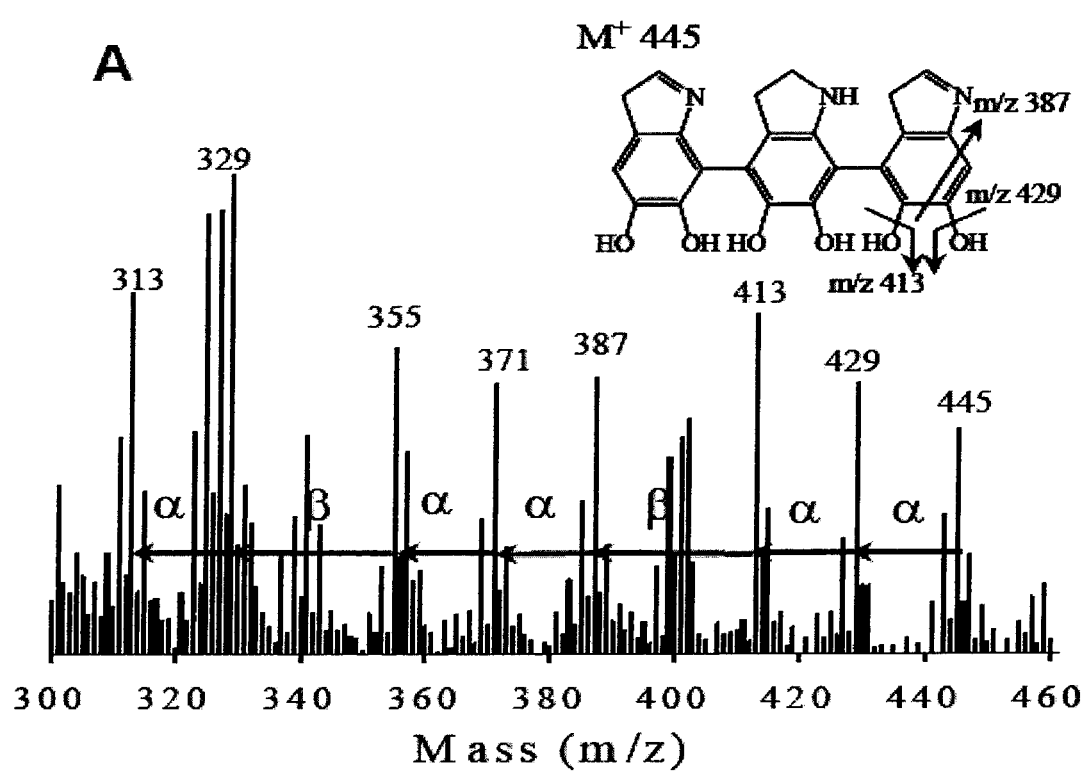
FIG. 5A. ToF-SIMS spectra of polydopamine-coated glass. The mass spectrum showed a trimer of 5,6-dihydroxyindole, possibly fragmented from a long-chain polymer of similar composition. The characteristic pattern of fragmentation suggests liberation of two hydroxyl groups and a portion of the phenyl group, identifying each subunit as derived from dopamine polymerization.
Figure 5B:
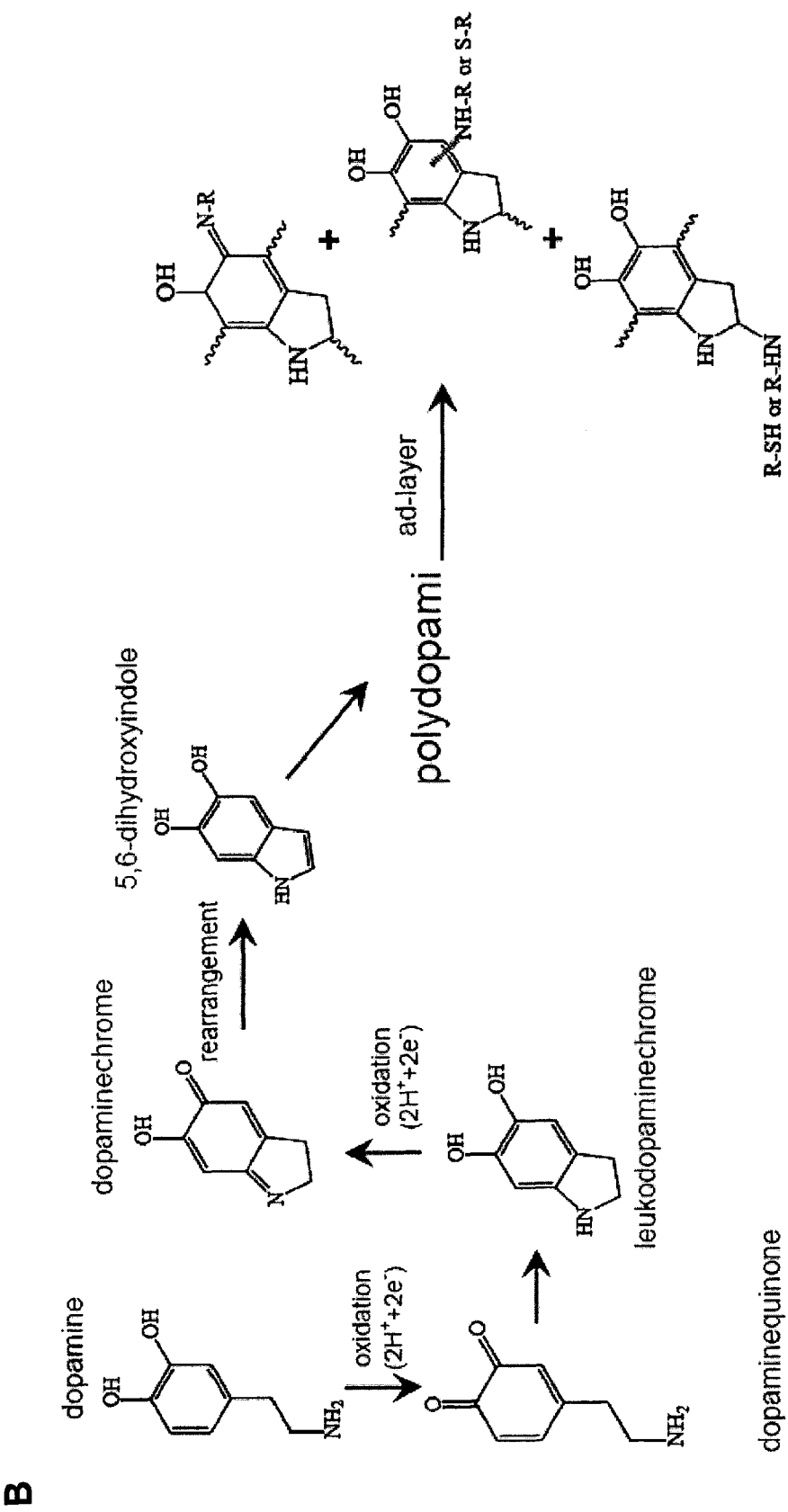
FIG. 5B. Possible structural evolution and polymerization mechanisms of dopamine, as well as suggested reaction mechanisms for organic ad-layer formation on polydopamine-coated substrates. Under an oxidative condition (e.g. alkaline pH, oxidants, etc.) dihydroxyl group protons in dopamine are deprotonated, becoming dopaminequinone, which subsequently rearranges via intramolecular cyclization to leikodopaminechrome. Further oxidation and rearrangement leads to 5,6-dihydroxyindole, whose further oxidation causes inter-molecular cross-linking to yield a polymer that is structurally similar to the bio-pigment melanin. The polydopamine-coated substrate subsequently reacts with a variety of molecules via Shiff-base (top) and Michael addition chemistries.
Figure 13:
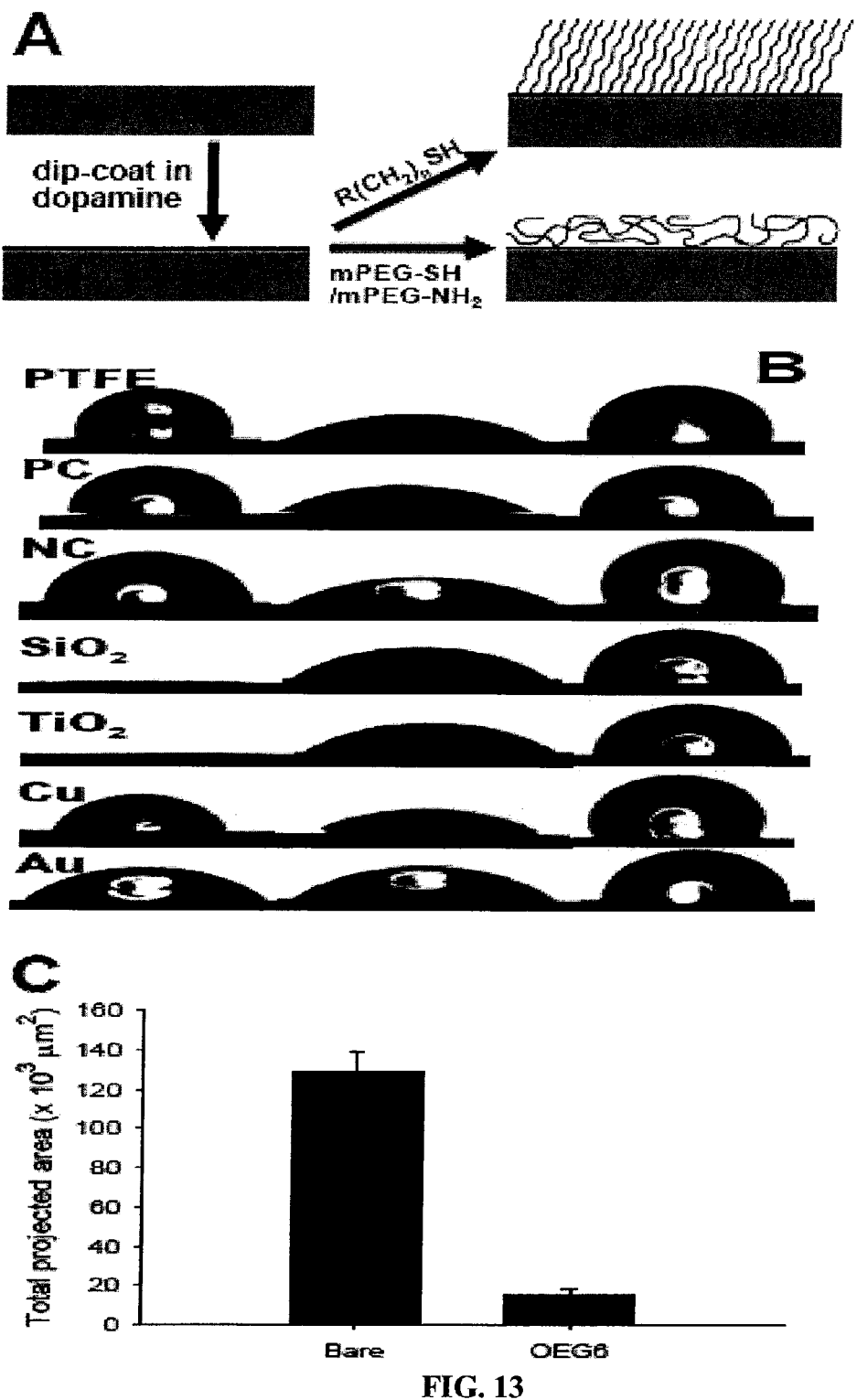
FIG. 13. Polydopamine-assisted grafting of various organic molecules onto polydopamine-coated substrates.
Figure 13:
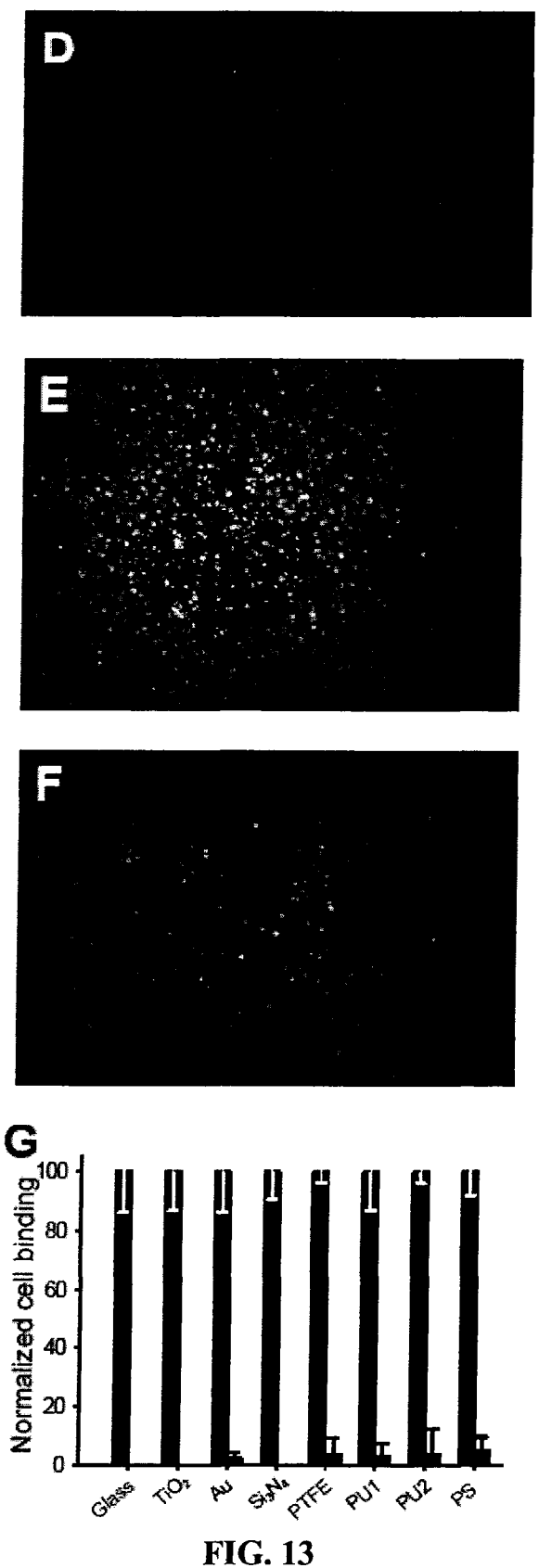

SMA-treated substrates can be used to support a variety of reactions with organic species for creating functional organic ad-layers. For example, under oxidizing conditions, catechols react with thiols and amines via Michael addition or Schiff base reactions (FIG. 5B). Thus, immersing SMA-treated substrates into a thiol- or amine-containing solution provides a convenient route to organic ad-layer deposition through thiol- and amine-catechol adduct formation (FIG. 13A). The following examples demonstrate methods for depositing organic ad-layers in the form of alkanethiol monolayers, synthetic polymers, and biopolymer coatings.

Polymeric Grafting.

SMA-treated substrates can be used to support polymeric ad-layers, including PEG, hyalurinic acid (HA), polyethylenimine, heparine, chitosan, or any other moiety described above. For example, PEG-grafted, SMA-treated substrates can be used for fouling-resistant substrates, and HA-immobilized surface is useful in hematopoietic cell cultures. Polymer ad-layers were grafted onto SMA-treated substrates in a method according to the present invention, wherein the secondary reactive moiety comprises thiol- or amine-functionalized polymers, thus yielding bioresistant and/or biointeractive substrates. Alternative forms of polymeric grafting are also envisioned, including free radical graft polymerization, atom-transfer radical polymerization, plasma polymerization/deposition, plasma treatment and surface irradiation, and cationic and anionic monomer or oligomer additions.

Protein Labeling.

SMA-treated substrates can be used to support protein ad-layers such as flagella, antibodies for diagnostic devices as well as therapeutic proteins and peptides for therapeutic purposes. For instance, flagella-labeled substrates are useful in chemotaxis and cellular network studies. Currently, the only approach for single flagella-labeling has been the physical adsorption of flagella antibody on micro-bead substrates and subsequent incubation in the presence of bacteria. By taking advantage of the chemical reactivity of SMA-treated substrates to flagella proteins, a general route for bacteria-independent flagella labeling is proposed, thereby providing a useful labeling technique for research in areas such as food science, bacterial chemotaxis, internal (stomach and intestine) medicine.

Amino Acid Ad-Layers.

SMA-treated substrates can be used to create peptide, protein and other organic ad-layers on SMA-treated substrates. Peptide, protein and other organic ad-layers are useful for bio-active, bio-inert, and diagnostic surfaces. For example, histidine has been widely used as an affinity tag to purify engineered proteins using a nickel-immobilized resin. Histidine is an amino acid containing an imidazole side chain with a relatively neutral pKa (approximately 6). The imidazole side chains and the relatively neutral pKa mean that relatively small shifts in cellular pH will change its charge. For this reason, histidine is useful as a coordinating ligand in metalloproteins, as a catalytic site in certain enzymes, such as iron-sulfur containing oxygenase (sulfite oxygenase, rubredoxin, etc) and hemoproteins.

Histidine-tags are also often used for affinity purification of recombinant proteins expressed in *E. coli* or other prokaryotic expression systems. Histidine-tagging is the option of choice for purifying recombinant proteins in denaturing conditions, and can also be used to detect proteins via anti-histidine-tag antibodies in gel staining (SDS-PAGE) with fluorescently labeled metal ions. This is useful in subcellular localization, ELISA, Western blotting or other immuno-analytical methods. However, histidine-tagging cannot be used to detect protein-protein interactions under reducing conditions or in combination with EDTA and many types of detergents. The approach described herein therefore represents a facile approach to linking His-tagged proteins onto SMA-treated substrates. This is useful for protein immobilization because it can be a convenient way to control the orientation of immobilized proteins on surfaces, diagnostic and/or purification purposes.

VIII. Examples

The following examples describe various new and useful embodiments of the present invention. While the examples refer to substrates treated with dopamine, it is envisioned that any SMA according to Formula I will also be useful in the methods described herein.

General Methods and Materials.

Materials and substrate preparation. Platinum, silver, copper, and palladium (Alfa Aesar, Ward Hill, Mass.), sapphire ($Al_2O_3$, Rubicon Tech Inc. IL), quartz (MTI crystal, MA), stainless steel, NiTi, Si (MEMC electronics, Italy), Carbothane®, Tecoflex®, polycarbonate and polyethylene terephthalate (PET) (McMaster Carr Inc, Chicago, Ill.), poly(styrene) (Sigma), glass (Fischer scientific), polydimethysiloxane (PDMS, Sylgard 184, Dow corning), GaAs (University Wafer, Boston, Mass.), and silicon nitride (generous donation by Dr. Keun-Ho Kim and Prof. H. Espinosa, Northwestern University) were cleaned ultrasonically in 2-propanol for ten minutes before use. Titanium (20-50 nm) and gold (20 nm deposited onto 5 nm Ti) substrates were prepared by electron beam deposition (Edwards FL400, Boc Edwards, Sussex, UK) on Si-wafers. PDMS (Dow Corning) was prepared by mixing 10 parts of backbone and 1 part of curing agent and cured at 100° C. for 2 hrs.

Example 1

SMA Solution

As shown herein, simple immersion of virtually any substrate in a dilute alkaline aqueous solution of dopamine buffered to a pH typical of marine environments (pH>7.5) results in spontaneous deposition of a reactive moiety on the substrate surface. In the case of dopamine, the substrate surface forms a thin adherent polymer film (FIG. 1F-1H). Atomic force microscopy (AFM) indicated that the polymer film thickness was a function of the immersion time and reached a value of up to 50 nm after twenty-four hours (FIG. 1G). X-ray photoelectron spectroscopy (XPS) analysis of twenty-five diverse materials coated for three hours or more revealed the absence of signals unique to the substrate (solid bars, FIG. 1H, and FIG. 3), indicating the formation of a polymer coating of 10 nm or more in thickness.

Figure 4:
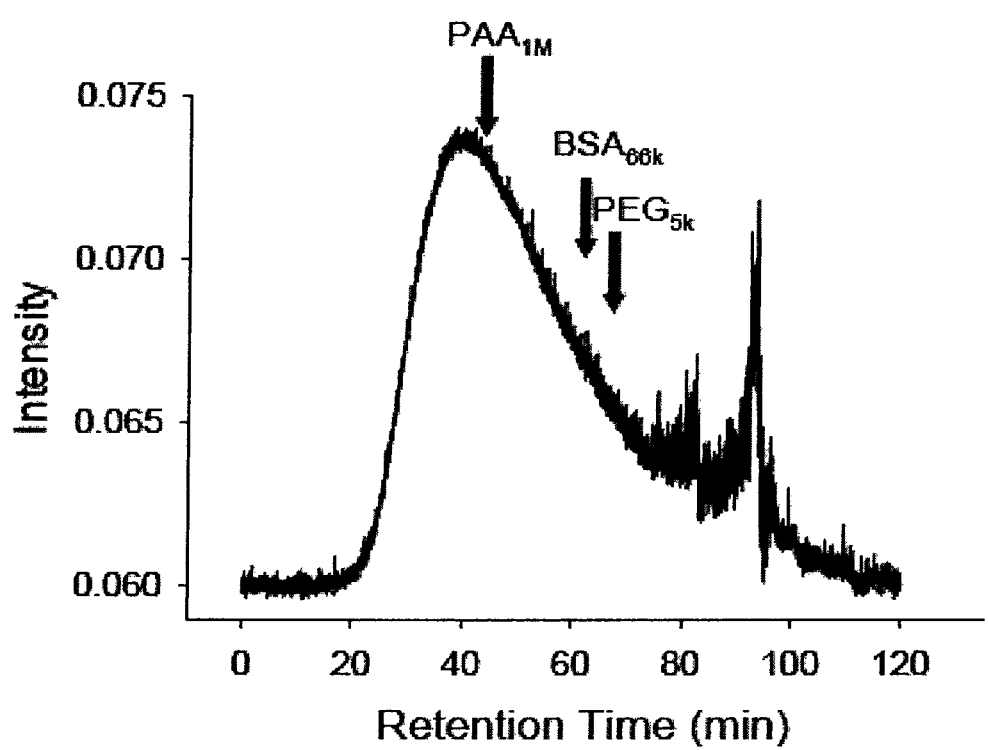
FIG. 4. Preliminary GPC analysis of dopamine solution after incubation for 60 hours at room temperature. Mobile phase buffer: 50 mM sodium phosphate, 100 mM NaCl, pH 6.5 with a flow rate of 0.3 mL/minutes (min). The sample was filtered before injection (pore size—0.8 microns (μm) and the retention times of molecular weight standards are indicated by the arrows. The broad peak at a retention time (40 min) correlates to polydopamine at an approximate molecular weight of about several million Dalton based on molecular weight standards (PEG, 5 kDa, Bovine Serum Albumin (BSA), 66 kDa, and polyacrylic acid (PAA), 1 MDa). A second peak at an elution time of 80 min indicates oligomer formation, and a third peak found at the retention time of 95 min is due to a contaminant in the GPC system.

The atomic composition of the SMA-treated substrate varied little (circles, FIG. 1H), suggesting that the composition of the SMA coating was independent of the substrate. The nitrogen-to-carbon signal ratio (N/C) of 0.1-0.13 is similar to the theoretical value for dopamine (N/C=0.125), implying that the coating is derived from dopamine polymerization. Gel permeation chromatography (FIG. 4) and time-of-flight secondary-ion mass spectrometry (ToF-SIMS) (FIG. 5) also suggest that dopamine polymerization caused the thin adherent film to form on the substrates.

SMA was found both in solution and on the substrate, with ToF-SIMS clearly revealing signals corresponding to dihydroxyphenyl-containing polymer fragments. Although the exact mechanism is unknown at this time, it is likely to involve oxidation of the catechol to a quinone followed by polymerization in a manner reminiscent of melanin formation, which occurs through polymerization of structurally similar compounds (FIG. 5).

Dopamine (2 mg/mL) was dissolved in 10 mM Tris-HCl (pH 8.5), and substrates were dipped into the solution. pH-induced oxidation changes the solution color to dark brown. Stirring and/or vertical sample orientation were necessary to prevent non-specific microparticle deposition on substrates. The polydopamine-coated substrates were rinsed with ultrapure water and dried by nitrogen gas before storage or treated as described below for ad-layer formation. Substrates coated in this manner remain stable on inorganic substrates unless scratched, treated by ultrasound, or dipped in a strong acid solution (<pH 1). Coatings on some organic substrates such as latex beads, Sephadex™ resins and some commercial plastics remain stable even in the presence of 1 N HC1 combined with ultrasound.

Figure 24:
FIG. 24. Different conditions (pH and concentration of dopamine) for polydopamine coating on polystyrene substrates.

In another example, different conditions (pH and concentration of dopamine) for polydopamine coating on polystyrene surfaces were used. At a fixed concentration of 2 mg of dopamine per milliliter of 10 mM Tris buffer, the polydopamine coating was tested as a function of pH (7.4, 8.5 and 10). Also, at a fixed pH of 8.5, dopamine concentration was varied from 0.05 to 2 mg/ml (coating time was 15 hrs for all samples) to test the coating capability (FIG. 24).

All conditions resulted in successful polydopamine coatings except for the coating in the 0.05 mg of dopamine per milliliter of Tris, pH 8.5.

Incubating dopamine solution at room temperature for several days (i.e., greater than three days) prior to immersing the substrates did not produce surface discoloration (to dark-brown) typical of polydopamine coatings, indicating that the coating did not occur or was too thin to observe visually. Furthermore, the modification reaction appears to be prevented under anaerobic conditions, since purging of dopamine solution with argon resulted in dramatically reduced solution color change and coating formation on immersed substrates.

Analyzing polydopamine molecular weight in solution was performed on a Dawn EOS (Wyatt Technology, Santa Barbara, Calif.) GPC system using a mobile phase buffer (50 mM sodium phosphate, 100 mM NaCl, pH 6.5, flow rate of 0.3 mL/min) and Shodex-OH columns. The sample was filtered before injection (pore size 0.8 wn).

Example 2

SMA-Treated Substrates

Under oxidative conditions (e.g., pH>7.5), a dilute alkaline aqueous solution of dopamine surprisingly modifies substrate surfaces to include reactive, adherent polydopamine nanofilms. Virtually all natural and synthetic substrates including, without limitation, noble metals (Au, Ag, Pt and Pd), metals with native oxide substrates (Cu, stainless steel, NiTi shape memory alloy), oxides ($TiO_2$, NiTt, $SiO_2$, quartz, $Al_2O_3$, and $Nb_2O_5$), semiconductors (GaAs and $Si_3N_4$), ceramics (glass and hydroxyapatite (HAp), and synthetic polymers (polystyrene (PS), polyethylene (PE), polycarbonate (PC), polyethylene terephthalate (PET), polytetrafluoroethylene (PTFE), polydimethylsiloxane (PDMS), polyetheretherketone (PEEK), and polyurethanes (carbothane® (PU1) and tecoflex® (PU2))) (FIG. 1H) were effectively modified using the SMA-treatment of the present invention.

To date, over twenty-five substrates were successfully modified by a dilute, alkaline solution comprising dopamine using an aqueous one-pot process. Potentially any substrate known to man, including various composite materials, can be used in this process. For instance, x-ray photoelectron spectroscopy (XPS) analysis showed that substrate signals such as Si2p, Ti2p, and Au4d were completely suppressed by the SMA-treated substrates as described in Example 1 (Table 1). Instead, carbon, oxygen, and nitrogen signals were detected after the modification with a similar atomic composition of a nitrogen to carbon ratio (experimental N/C=0.09-0.13, theoretical N/$C_{dopamine}$=0.125) irregardless of substrates. Unavoidable carbon contamination in ambient conditions lowered the N/C ratio in XPS.

Figure 3:
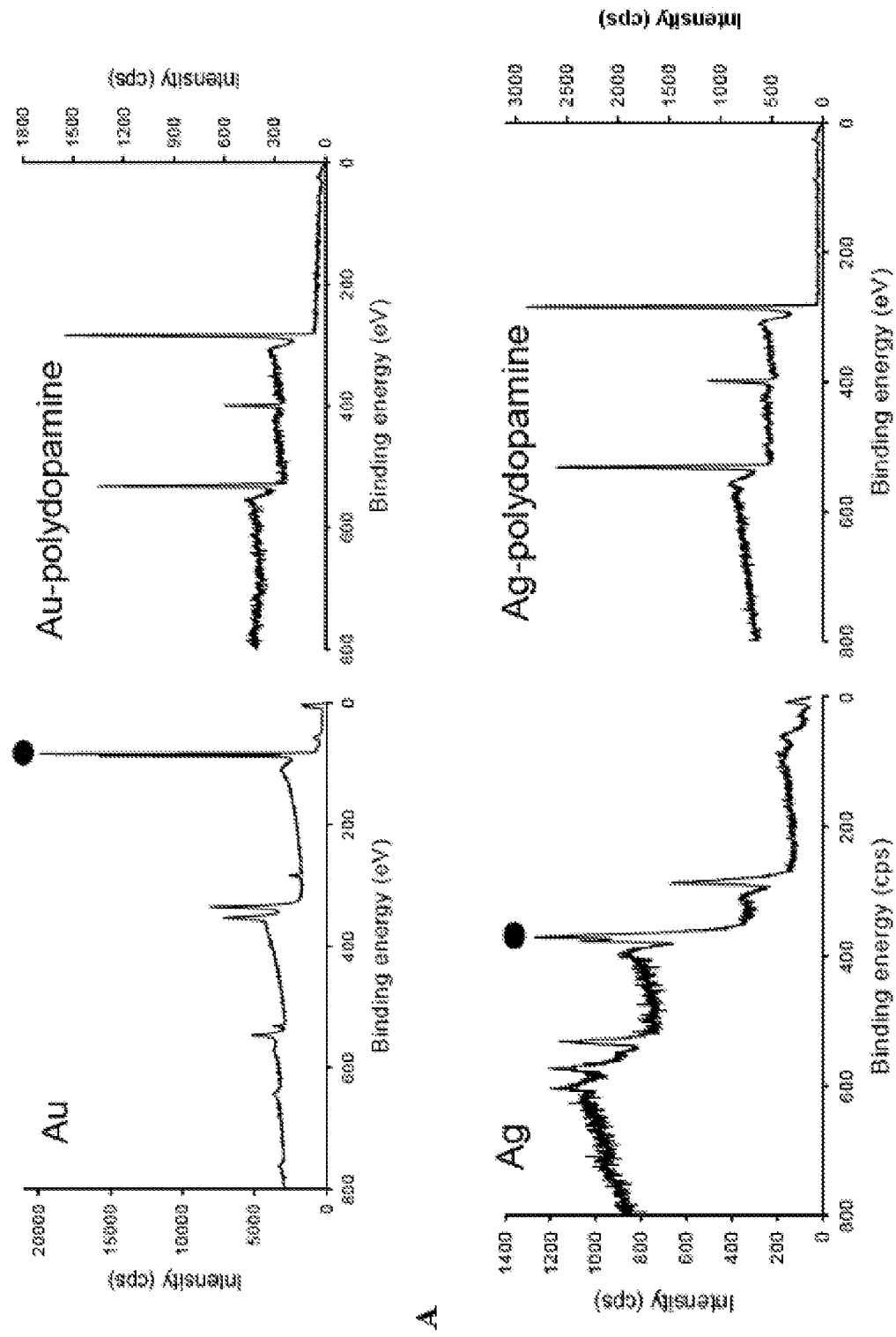
FIG. 3. X-ray Photoelectron Spectroscopy (XPS) characterization of polydopamine-coated substrates. XPS spectral changes of twenty-five substrates (A-Y) before (left column) and after (right column) polydopamine coating. The characteristic XPS substrate signals for unmodified substrates (left) were marked by filled circles, which were completely suppressed after polydopamine coating (right). Instead, carbon (~285 eV), nitrogen (399.5 eV), and oxygen (532.5 eV) photoelectron peaks (in order from low to high binding energy) were observed. The area ratio of nitrogen-to-carbon was determined for twenty-five different substrates, and those values are shown in FIG. 1H (circles). Substrate XPS peaks used in the experiments are summarized in Table 2.
Figure 3:
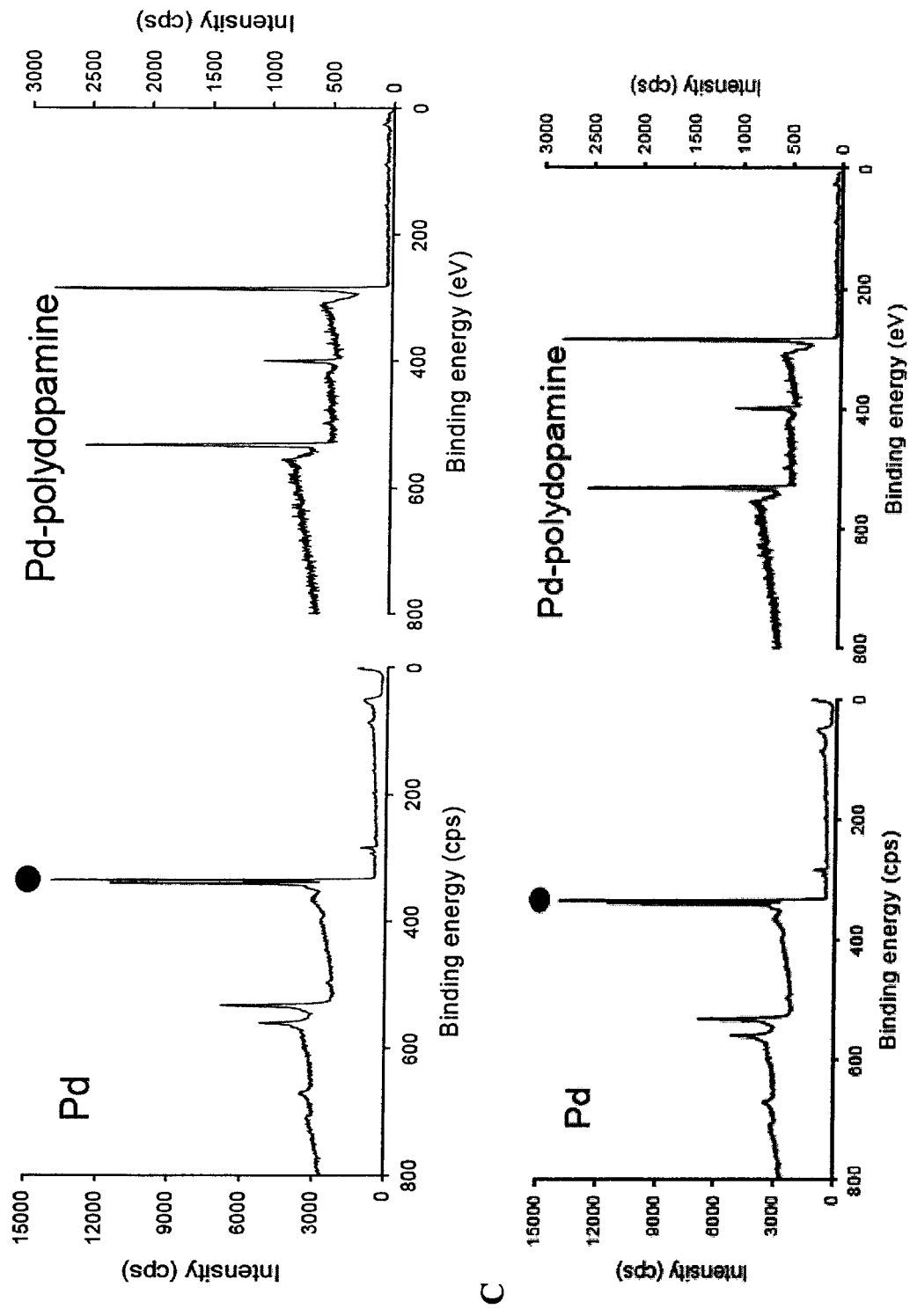
Figure 3:
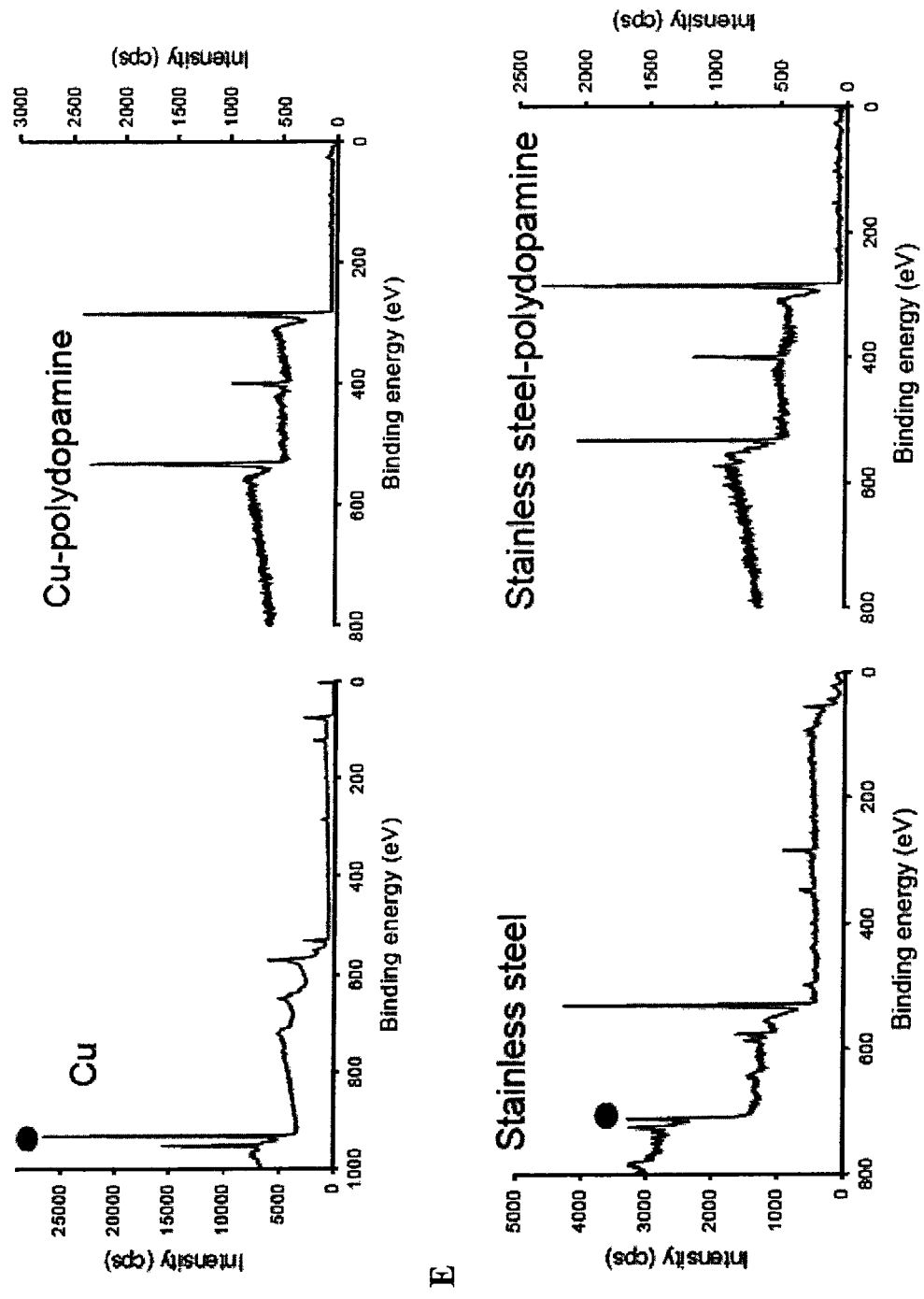
Figure 3:
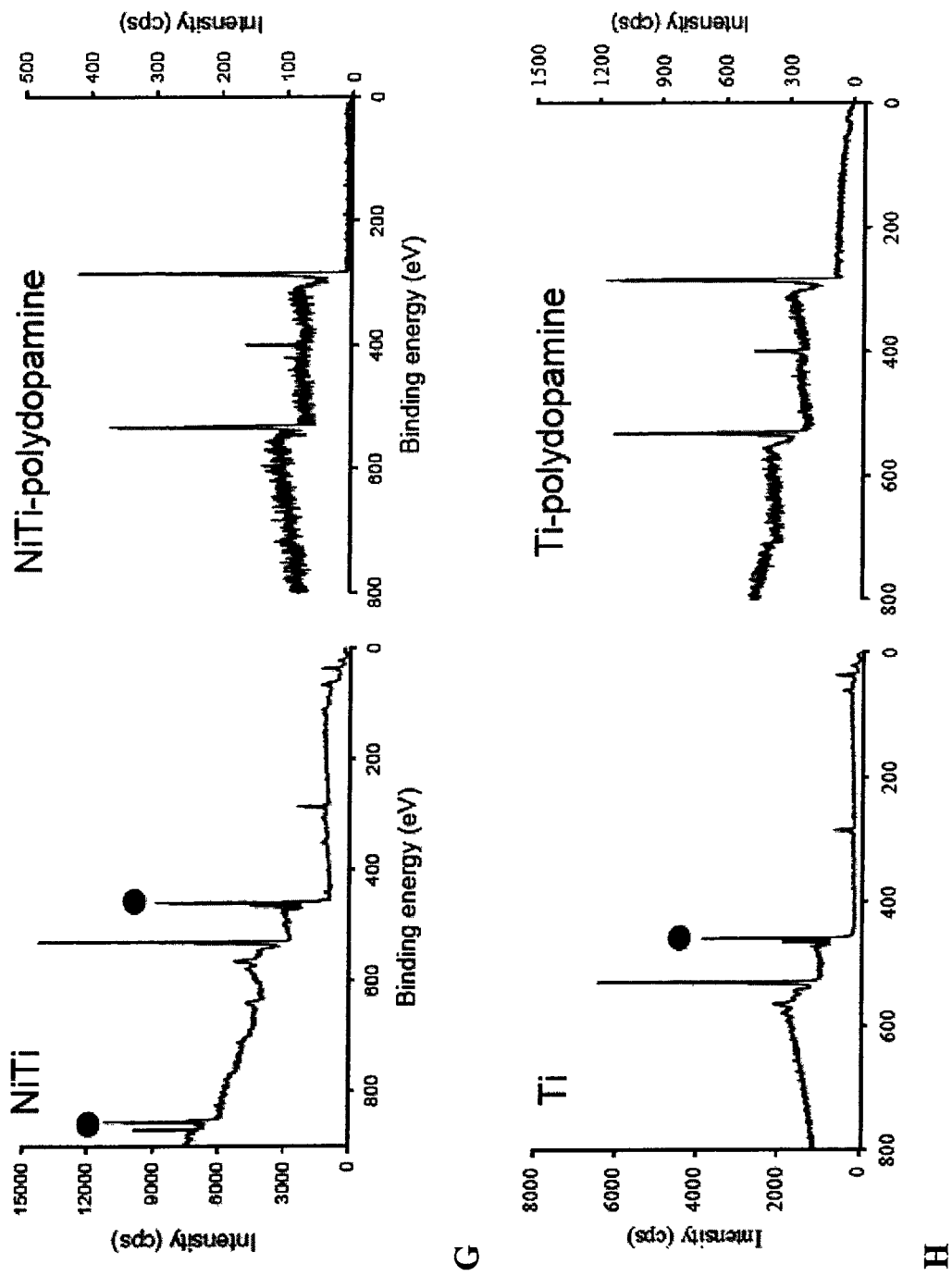
Figure 3:
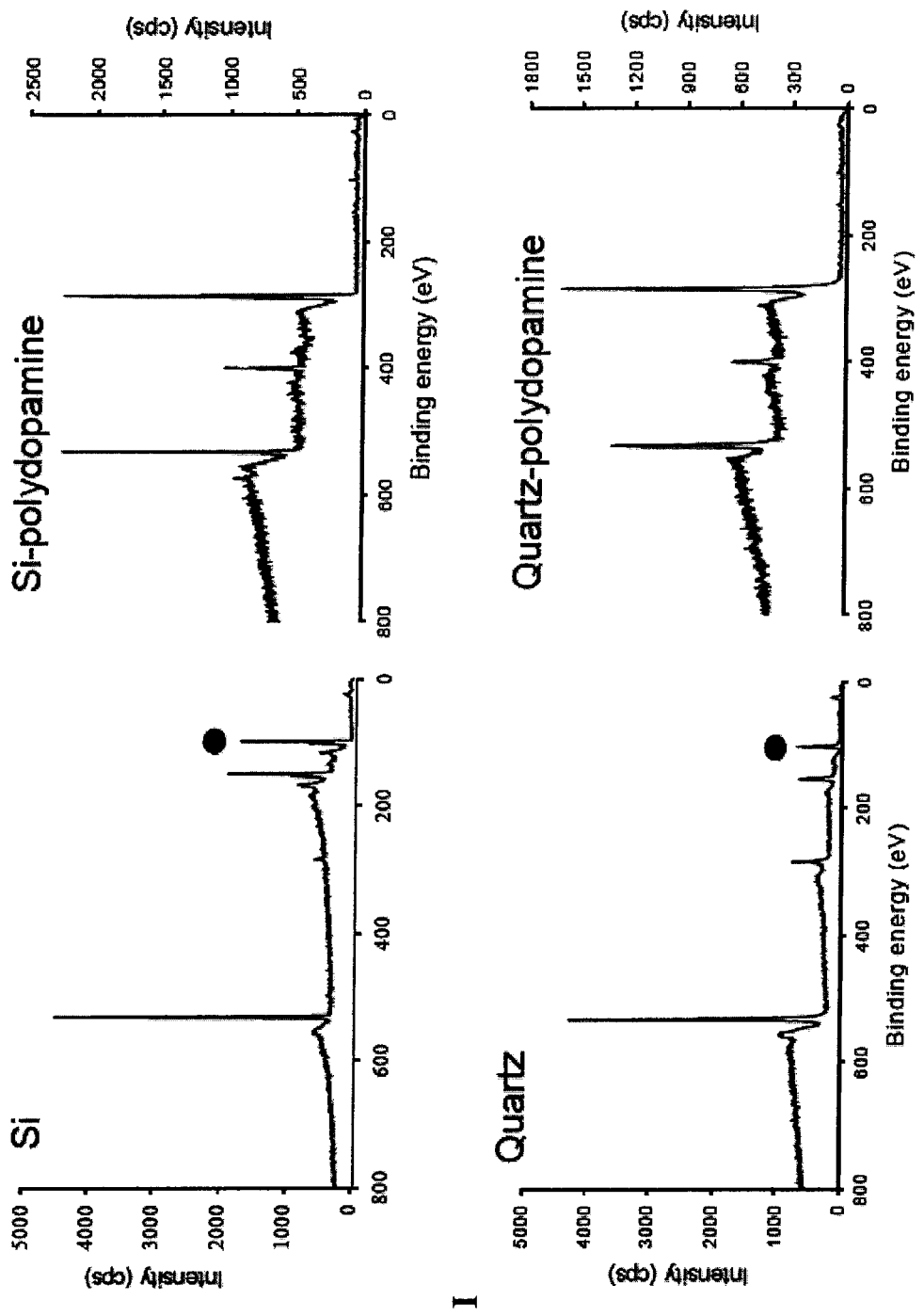
Figure 3:
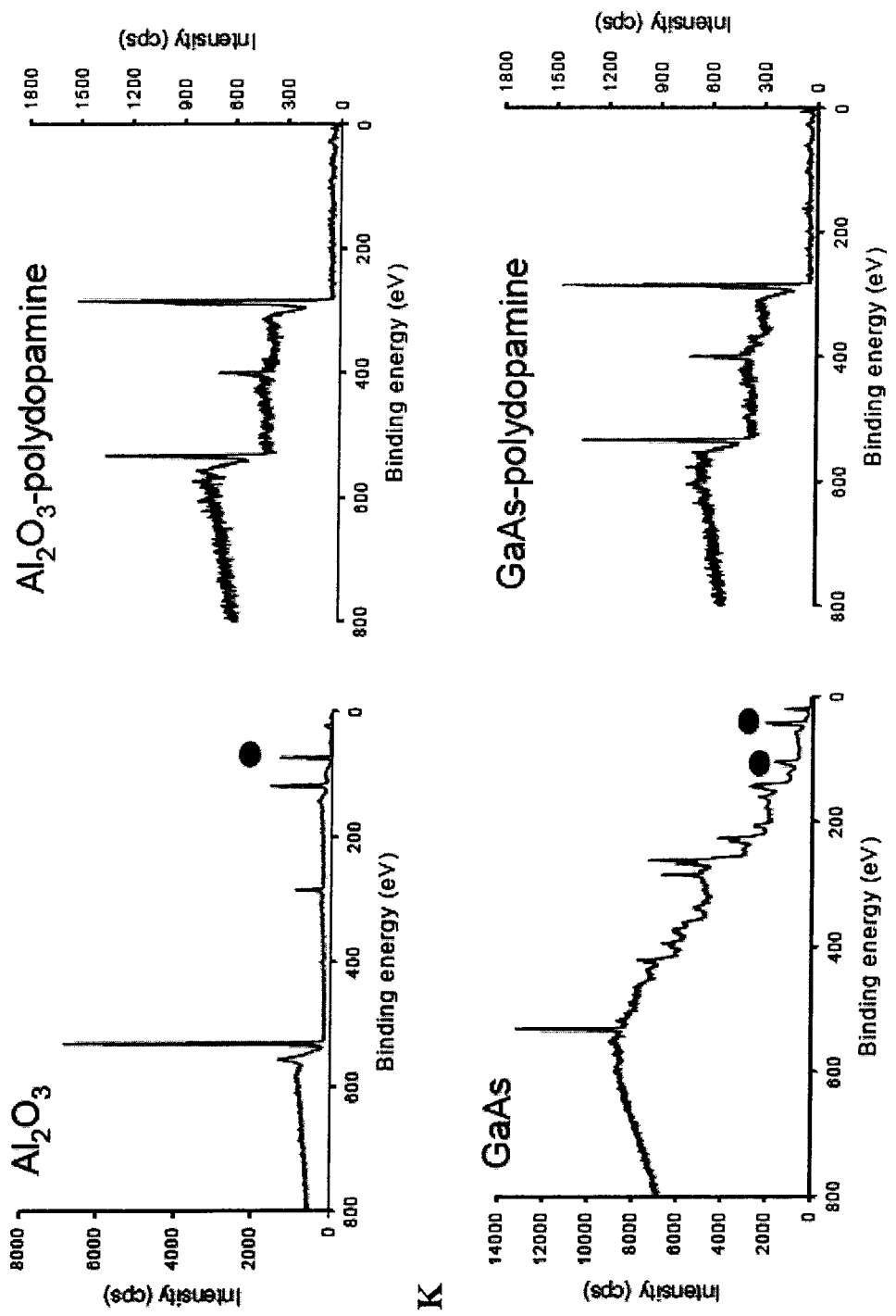
Figure 3:
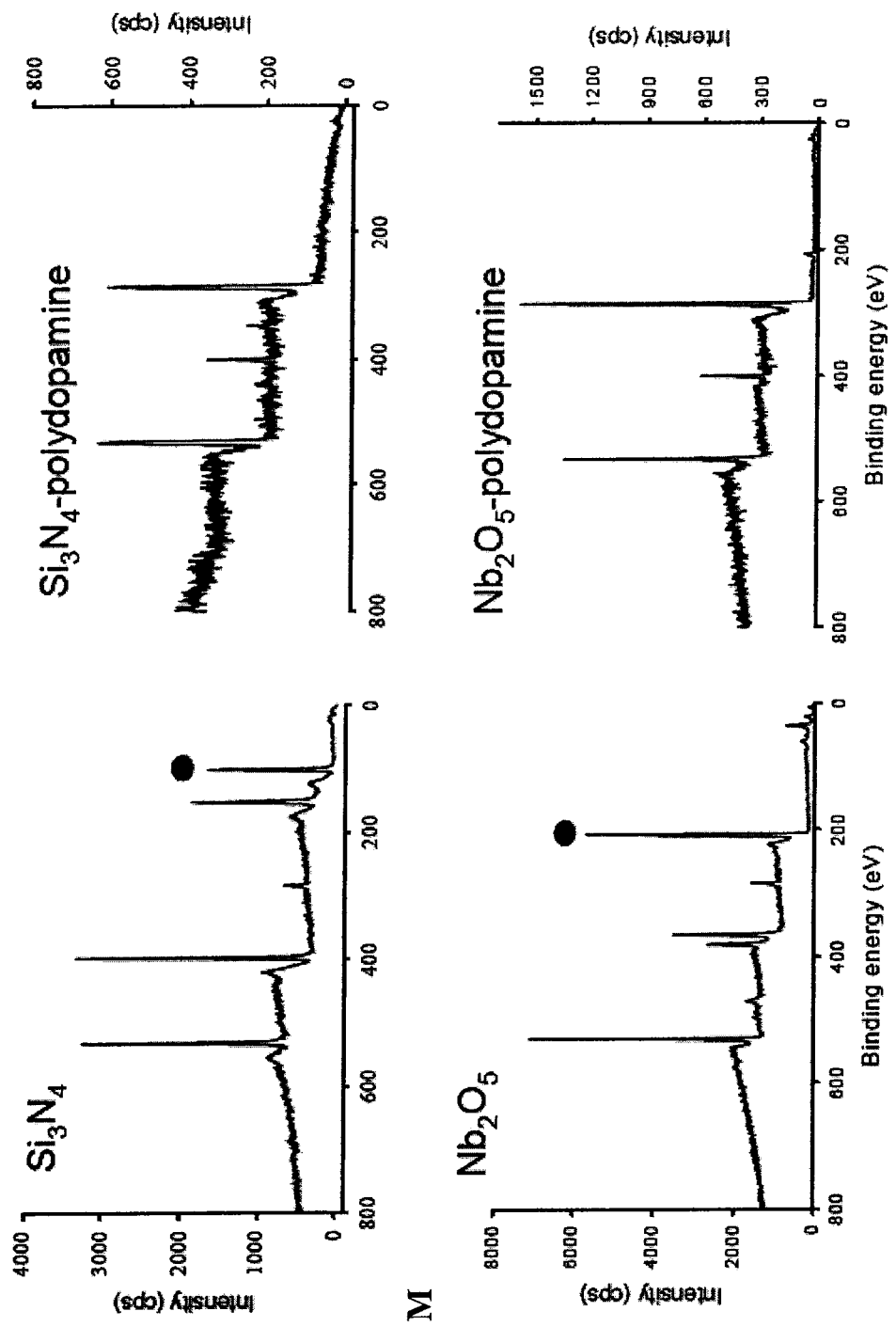
Figure 3:
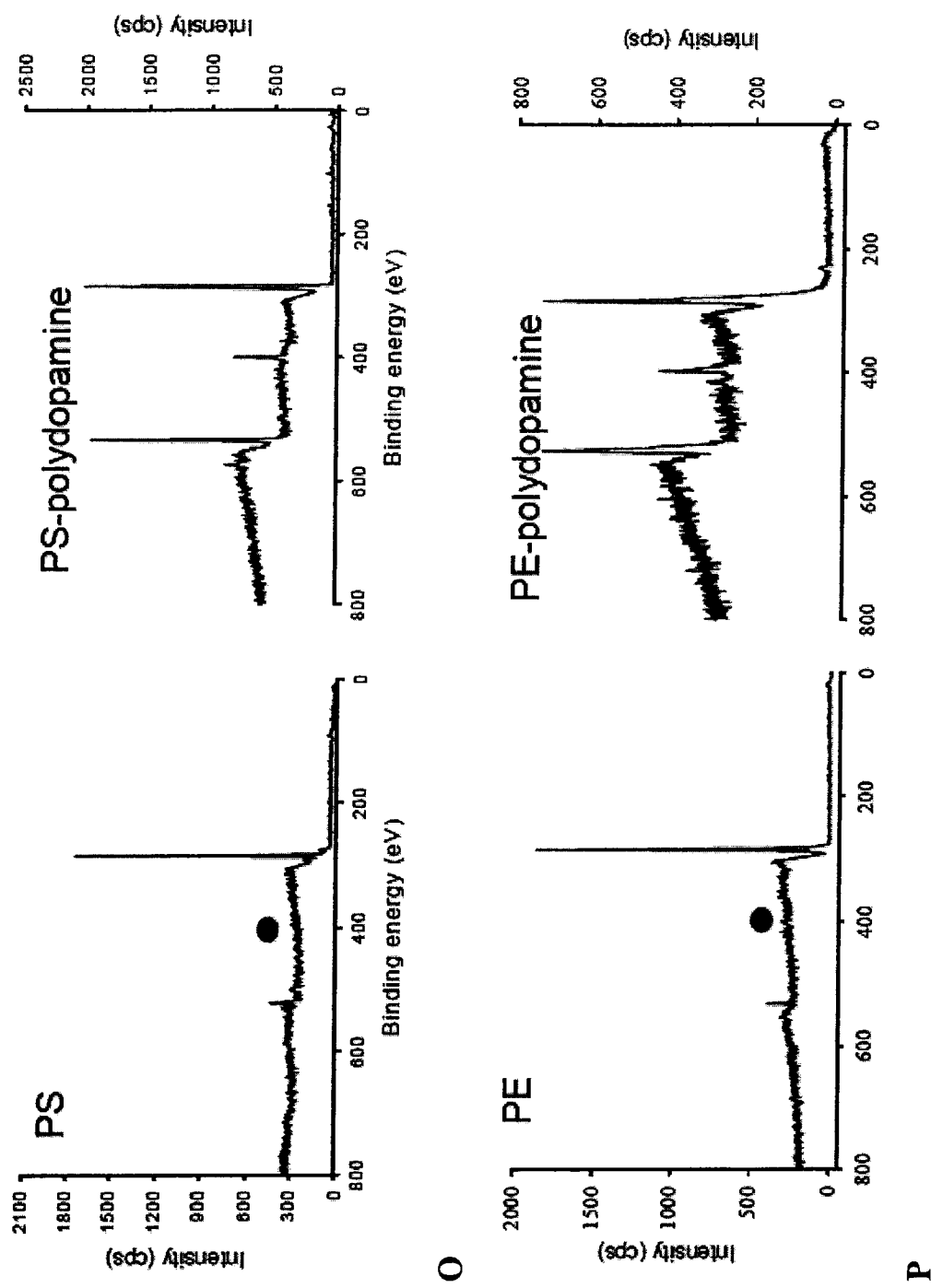
Figure 3:
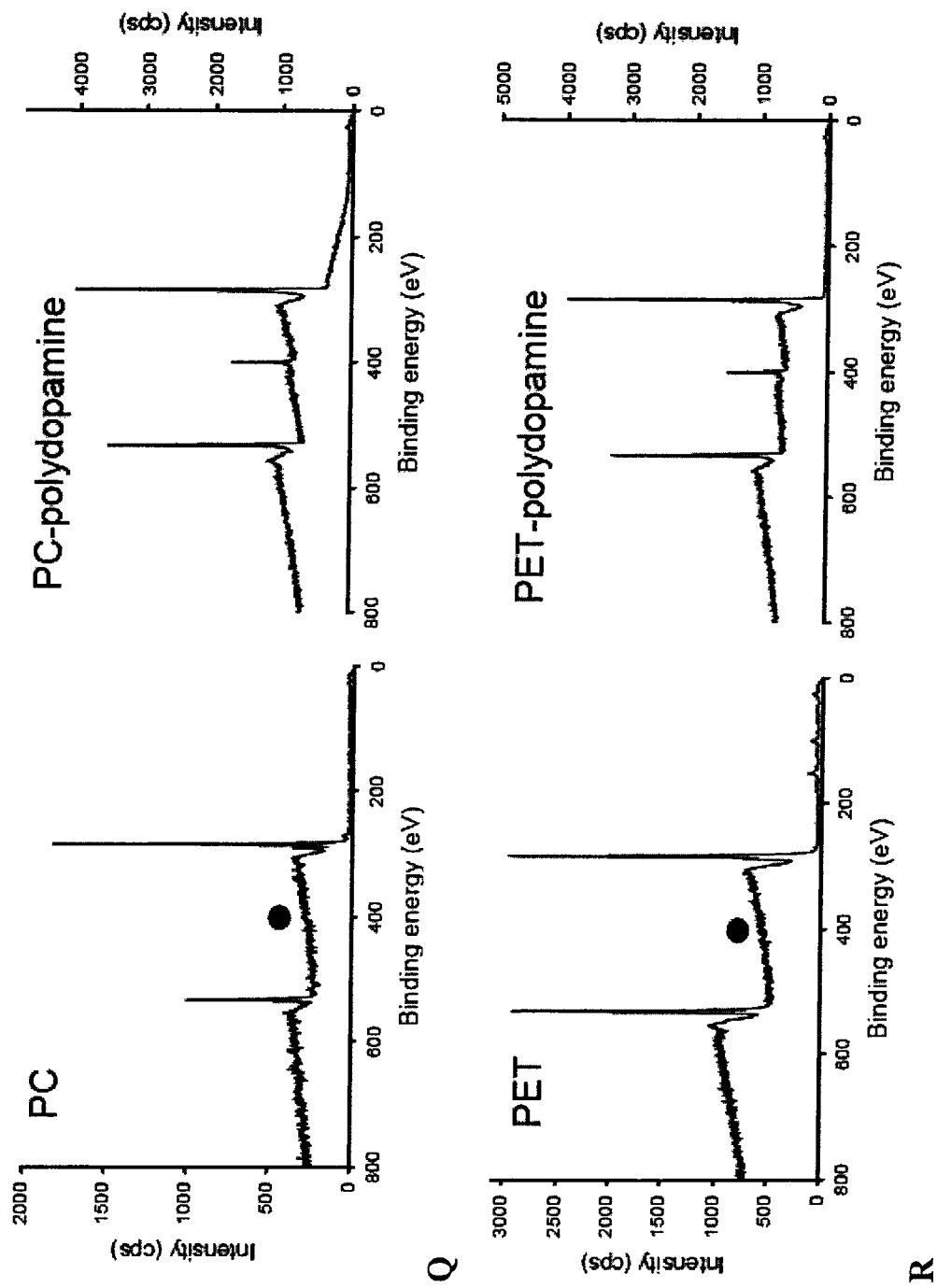
Figure 3:
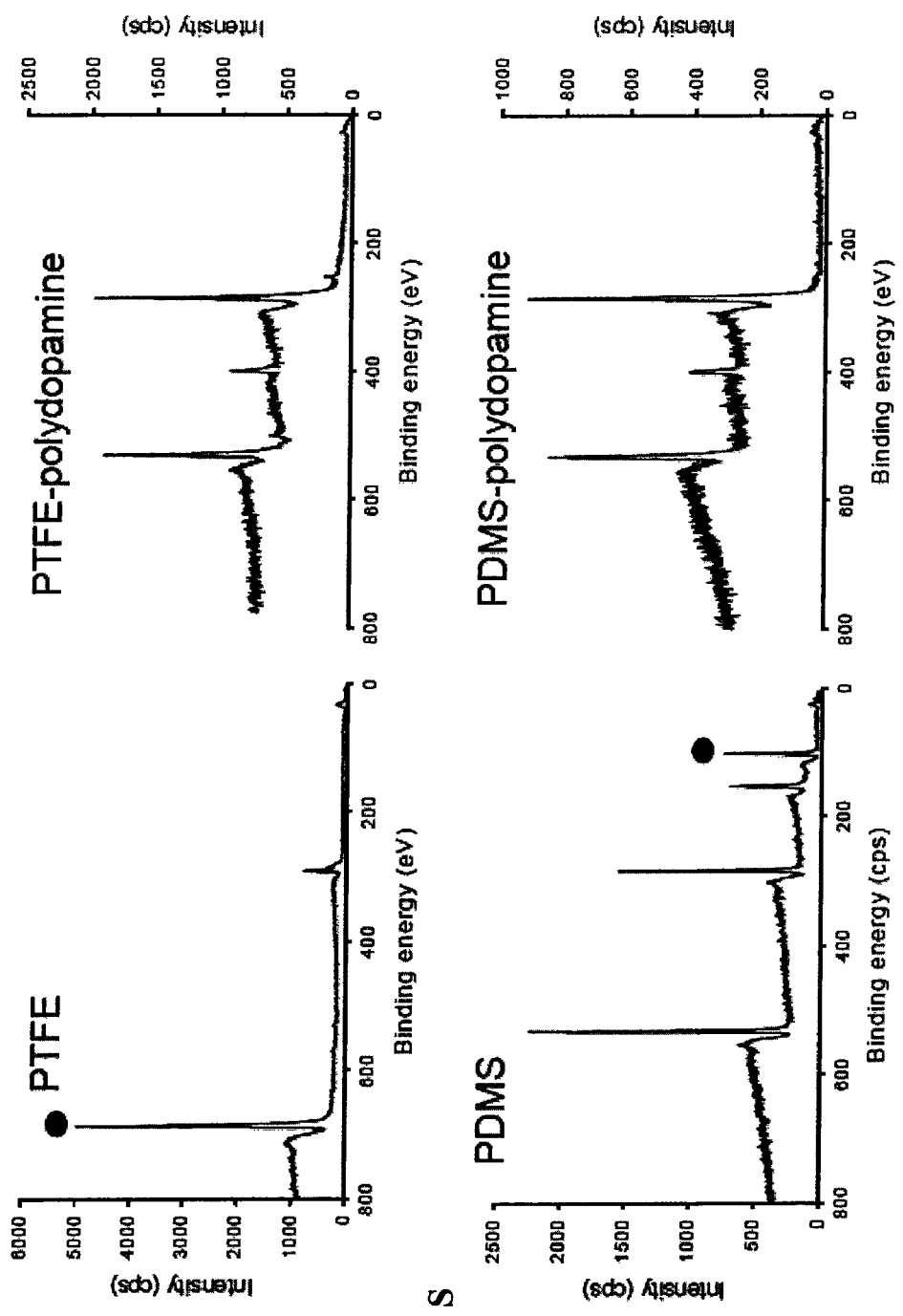
Figure 3:
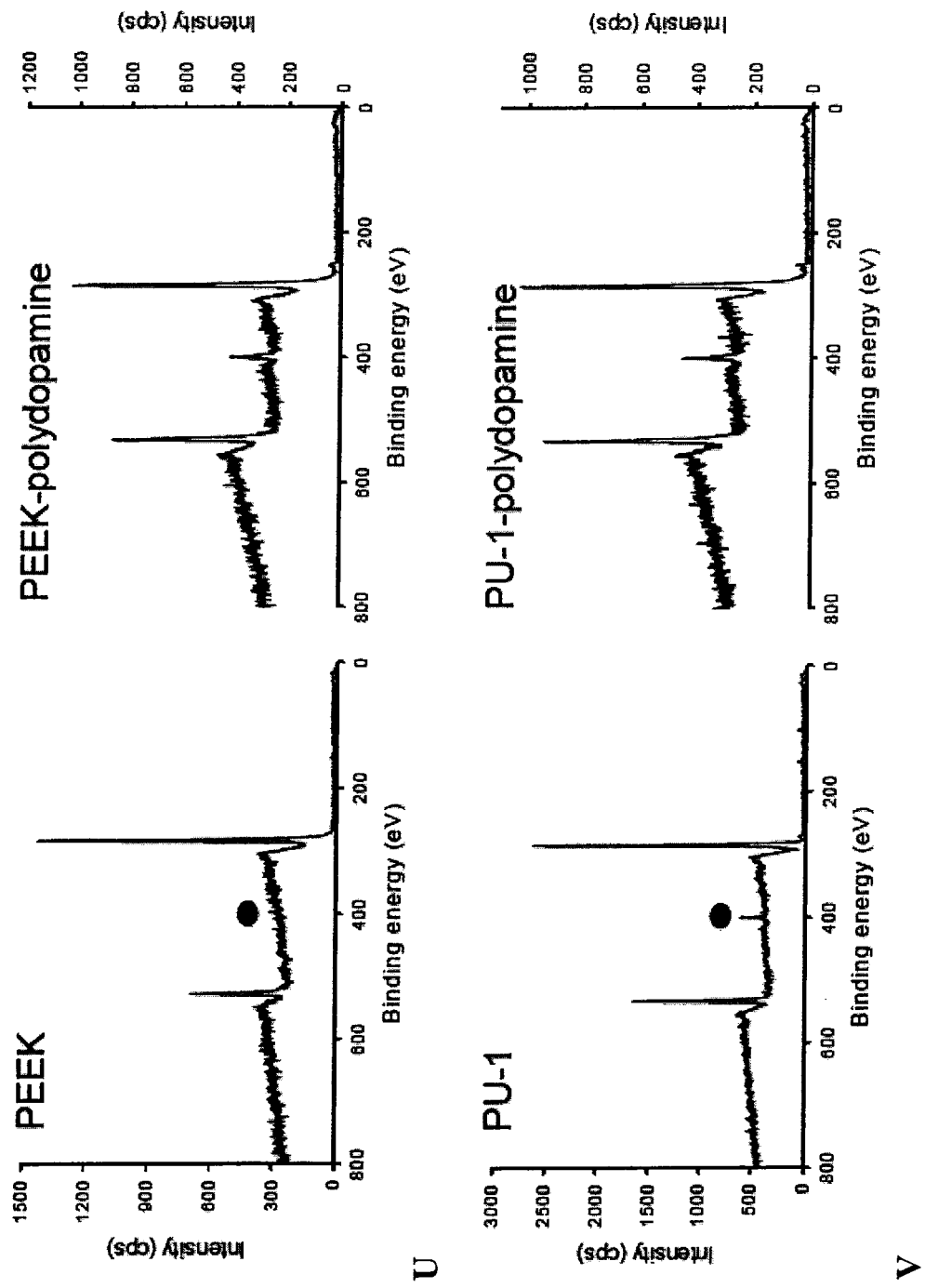
Figure 3:
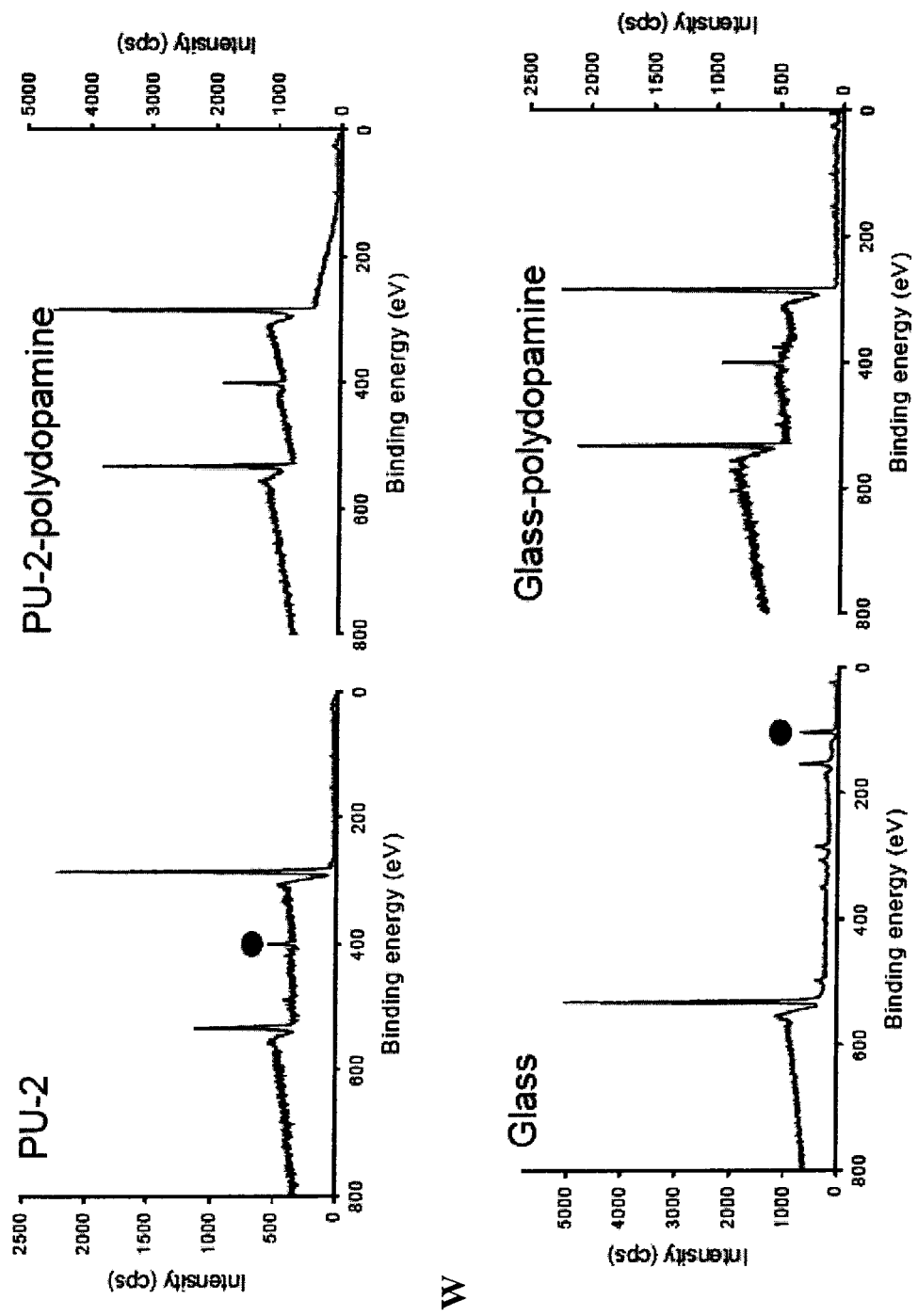
Figure 3:
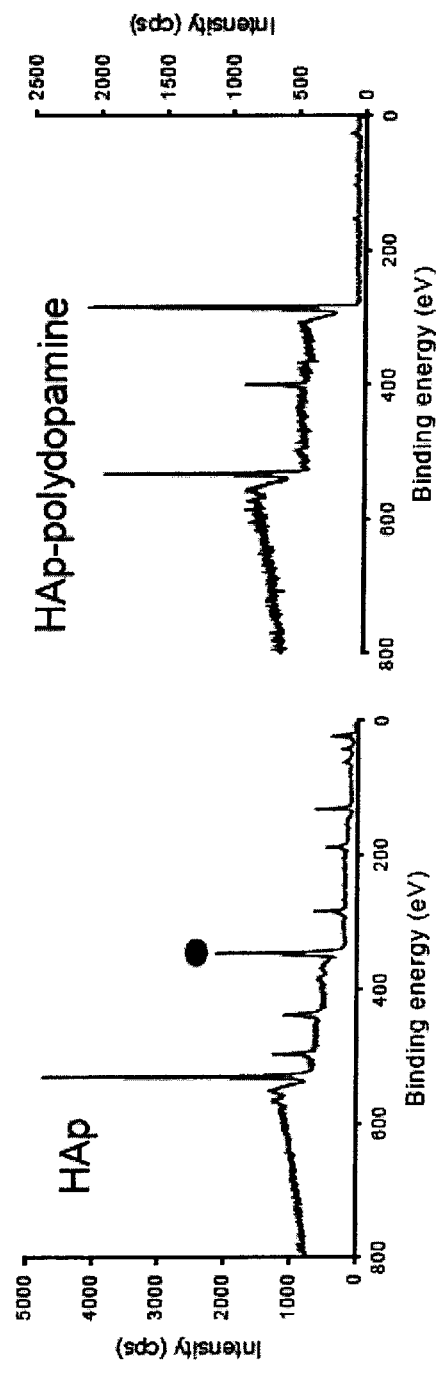

Table 2 illustrates the substrates and corresponding atoms (binding energy and orbital) used as characteristic substrate peaks for XPS characterization (as asterisk indicates synthetic, polymeric substrates without unique XPS signals except for carbon, nitrogen and oxygen.) The presence of the reactive moiety (in the case of dopamine, the reactive moiety formed is an adherent polymeric film) on the substrates was confirmed by the appearance of N1s signal after SMA-treatment, as shown in FIG. 3 (399.5 eV for PS, 399.1 eV for PE, 399.7 eV for PC, 399.6 eV for PET, and 399.8 eV for PEEK). The reactive moiety on PU-1,2 was confirmed by the nitrogen-to-carbon ratio after coating due to the presence of substrate nitrogen).

TABLE 2

| Substrate | Binding energy (eV) (photoelectron orbital) |
| --- | --- |
| Au | 84.1/84.9 (Au4$f_{7/2,5/2}$) |
| Ag | 369.9/373.9 (Ag3$d_{5/2,3,2}$) |
| Pt | 71.1/74.7 (Pt4$f_{7/2,5/2}$) |
| Cu | 952.5/932.5 (Cu2$p_{1/2,3/2}$) |
| Pd | 335.1/340.5 (Pd3$d_{5/2,3/2}$) |
| Stainless steel | 740.0/723.0 (Fe2$P_{3/2,1/2}$) |
| 110$_2$ | 456.5/462.4 (112$p_{3/2\ 1/2}$) |
| NiTi | 854.1/870.9 (Ni2$p_{3/2\ 1/2}$) |
| Quartz, Glass | 103(quartz), 102(glass) (Si2p) |
| $SiO_2$, $Si_3N_4$ | 99.0/99.8 (Si2$p_{3/2,1/2}$) |
| $Al_2O_3$ | 118.6 (Al$_{2s}$) |
| GaAs | 41.7, 106.5 (As3$d_{3/2}$ Ga3$p_{1/2}$) |
| PDMS | 102.2 (Si2p) |
| Nb2O5 | 207/209.5 (Nb3$d_{5/2,3/2}$) |
| PTFE | 686.1 (F1s) |
| PS* | 284.7 (C1s) |
| PE* | 284.8 (C1s) |
| PC* | 284.7 (C1s) |
| PET* | 284.7 (C1s) |
| PEEK* | 284.8 (C1s) |
| HAp | 346.5/350.2 (Ca2$P_{3/2,1/2}$) |

Surface Characterization.

XPS spectra were obtained using an Omicron ESCALAB (Omicron, Taunusstein, Germany) with a monochromatic A1 Ka (1486.8 eV) 300-W X-ray source, a flood gun to counter charging effects, and ultrahigh vacuum ($-10^{-9}$ torr). The take-off angle was fixed at 45° except as otherwise mentioned. High-resolution scans were acquired to calculate the chemical compositions of the substrates. Time-of-flight secondary ion mass spectroscopy (Physical Electronics, Eden Prairie, Minn.) was used to characterize the atomic composition of polydopamine coatings and metal ad-layers (copper and silver). The mass spectrometer was equipped with a Ga ion gun operated at 15 keV with a raster size of typically 100-200 p.m. Multi-mode atomic force microscopy (Veeco Inc., Santa Barbara, Calif.) was used for imaging (tapping-mode using Si-cantilever, Veecoprobes, resonance frequency=210-240 kHz)).

Total Internal Reflection Fluorescence (TIRF) Microscopy.

Detailed experimental procedures have been described elsewhere (Qu et al. *Proc. Natl. Acad. Sci. USA* 101, 11298 (2004)). Briefly, an Olympus 1×71 inverted fluorescence microscope (Melville, N.Y.) and a 60× objective (Olympus, N.A.=1.45 oil immersion) were used for single-molecule adsorption images. A 532-nm laser (New Focus 3951-20, 20 mW power, San Jose, Calif.) was used as a light source. An O.D. equals one neutral density filter was used for most experiments. The incident laser power was roughly 0.5 mW, illuminating a circular region of 40 1.1 m in diameter. After excitation, the emitted photons were collected by a filter cube (Chroma Q560LPBS, HQ585/40M, Rockingham, Vt.), magnified by a 3.3× eyepiece and detected by a TEcooled and frame-transfer CCD (Andor, DV435-BV, South Windsor, Conn.). The protein used in this experiment was Cy3 conjugated Enigma homolog (Enh). The protein was dissolved in 50 mM phosphate buffer pH 7.0 (1 1. IM) and experiments performed at room temperature (exposure time=33 msec).

Example 3

Untreated Substrates

In this example, substrates were tested to determine if substrates could be modified according to the present invention in an untreated condition. Accordingly, the following demonstrates that SMA-treated substrates that have not been cleaned (i.e., are used as received) can be modified to include at least one reactive moiety.

Figure 26:
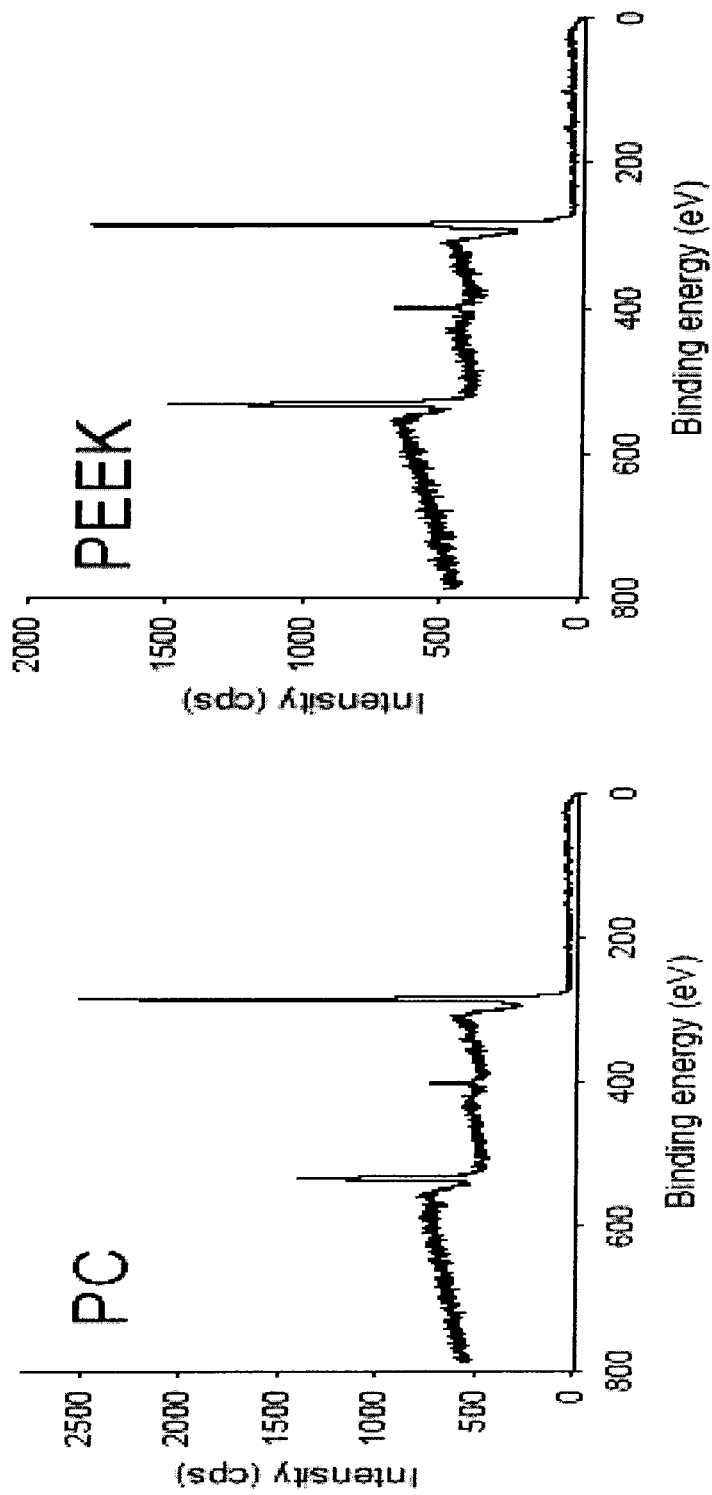
FIG. 26. XPS data to determine SMA-treatment on untreated substrates PC (A) and PEEK (B).

Substrates PEEK and PC were contacted with dopamine in a dilute, alkaline solution (2 mg/mL dopamine dissolved in 10 mM Tris; pH 8.5) for 5 hrs. XPS was used to determine the efficacy of the SMA-treated substrates. The presence of N1s signals (approximately 400 eV) (see FIG. 26A-B) indicated successful polydopamine coating on unclean substrates (bare substrates do not show N1s).

These results indicate that substrates may be modified according to the present invention, even when such substrates are covered in paint, oil, grease, rust, protectant and the like.

Example 4

Photolithography

Figure 6:
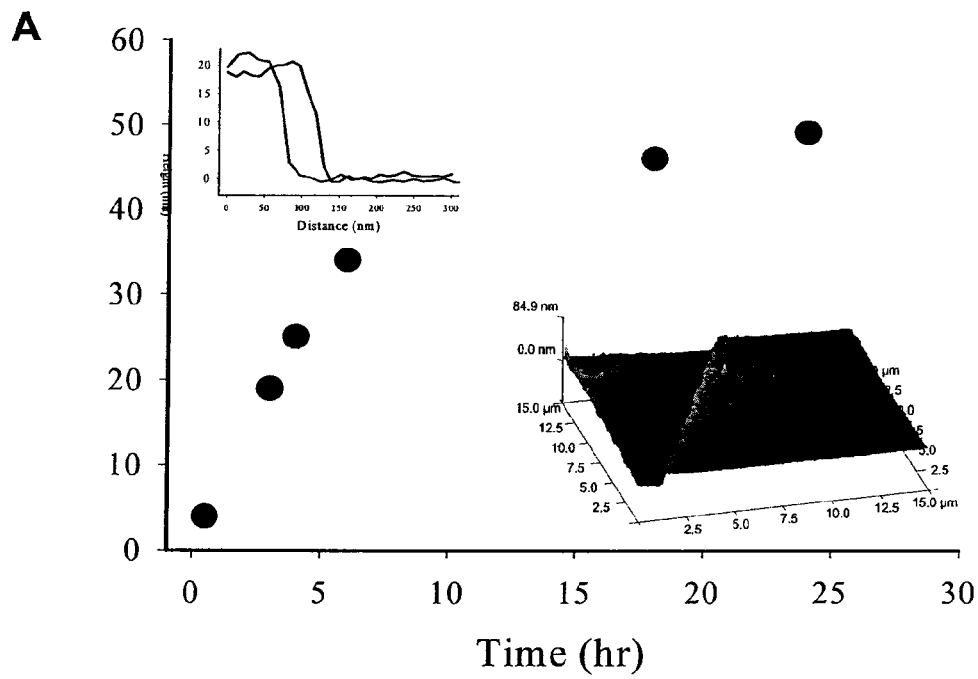
FIG. 6. Characterization of a surface-independent polydopamine-coated substrate.
Figure 6:
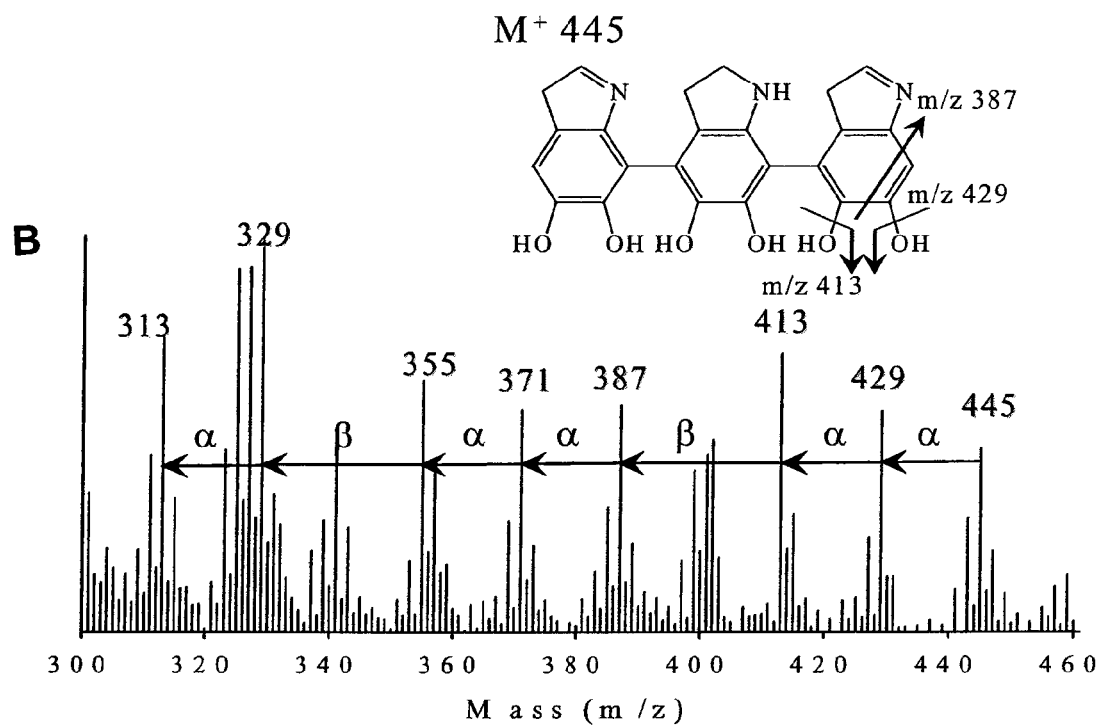

Dopamine's heterogeneous oxidative polymerization causes a substrate treated with dopamine to form a reactive moiety on the surface in the form of an adherent polymeric film. The polymeric film evolves in thickness as analyzed by photolithography micropatterning as a function of time and subsequent photoresist etching. This experiment resulted in substrates modified to include locally patterned thin films of dopamine, and the thickness was assessed by atomic force microscopy (AFM) (FIG. 6A inset). The coating thickness increased in a time-dependent manner and evolved up to 50 nm after one day (FIG. 6A).

The chemical identity of the polydopamine coating was analyzed by time of flight secondary ion mass spectrometry (ToF-SIMS). This technique relies on the ionization of chemical species ($2^{nd}$ ions) adsorbed on substrates which become fragmented molecules by incident primary ion beam ($Ga^+$), and the ionized molecules are analyzed in time-of-flight detectors. ToF-SIMS clearly proved the existence of polymerized dopamine (i.e., melanin ad-layers) by showing a fragmented trimer of 5,6-dihydroxlindole and leukodopaminechrome ($M^+$ 445, FIG. 6B), which are monomeric units generated by the sequential oxidation of dopamine (reaction sequence (I)-FIG. 2A). The ToF-SIMS results also showed interesting cleavage patterns: twice dehydroxylation ($\alpha,\alpha$; OH-phenyl-OH→phenyl-OH→phenyl) and ring opening ($\beta$; $C_6H_6 \to C_2H_2 + C_4H_4$) providing unambiguous evidence of diol and phenyl ring content in the adsorbed layers.

Photoresist (Microposit S-1818, Shipley, Marlborough, Mass.) was spin-cast at 4000 rpm for 50 sec and then baked for 1 mM at 95° C. Utilizing a contact mask aligner (Q2000, Quintel Corp. San Jose, Calif.), the photoresist was exposed to UV (345 nm) light for six seconds and was subsequently developed for forty sec (MF-CD-26, Shipley, Mass.). Polydopamine coating was applied to the patterned substrates for three to six hours as described above. Finally, photoresist was removed by immersion in N-methyl-pyrrolidinone (NMP) for five to ten seconds. The coating thickness (FIG. 3) was measured by AFM on patterned substrates.

Example 5

SMA-Assisted Electroless Metallization

Figure 7:
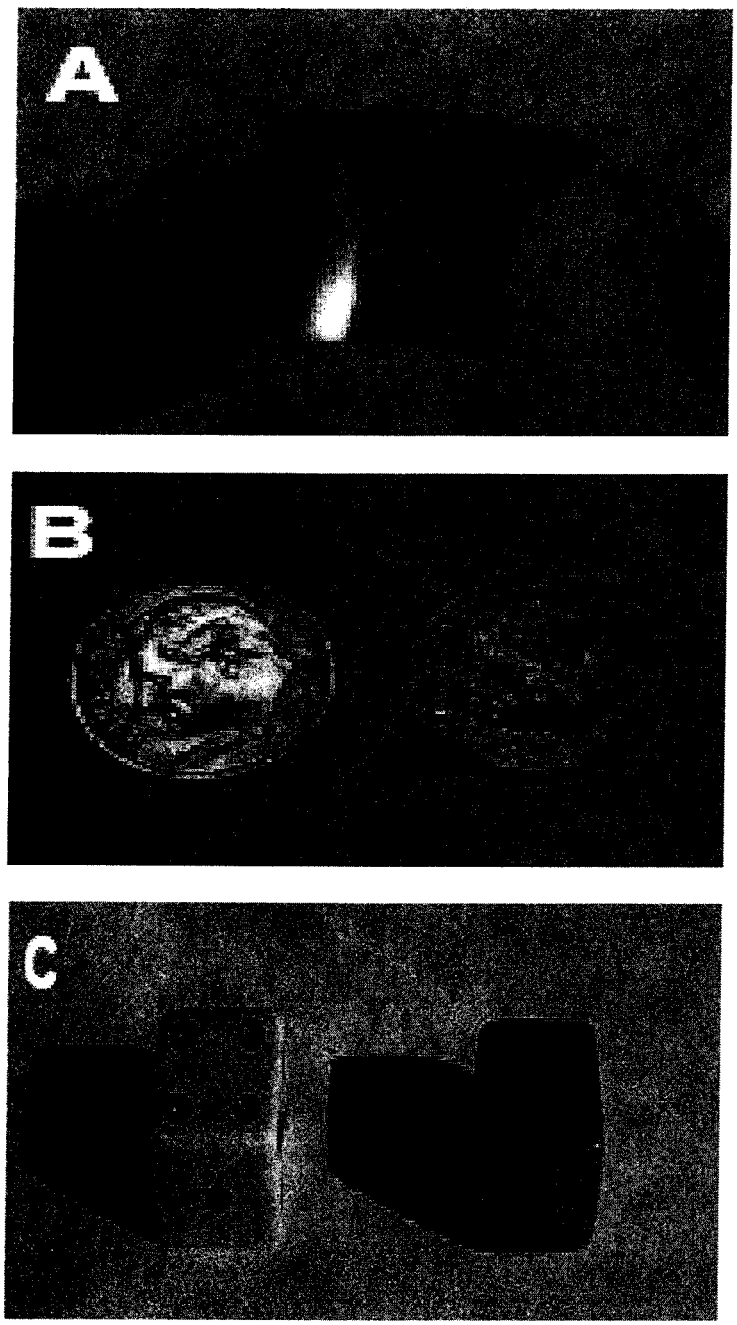
FIG. 7. Polydopamine-assisted electroless metallization of substrates.
Figure 7:
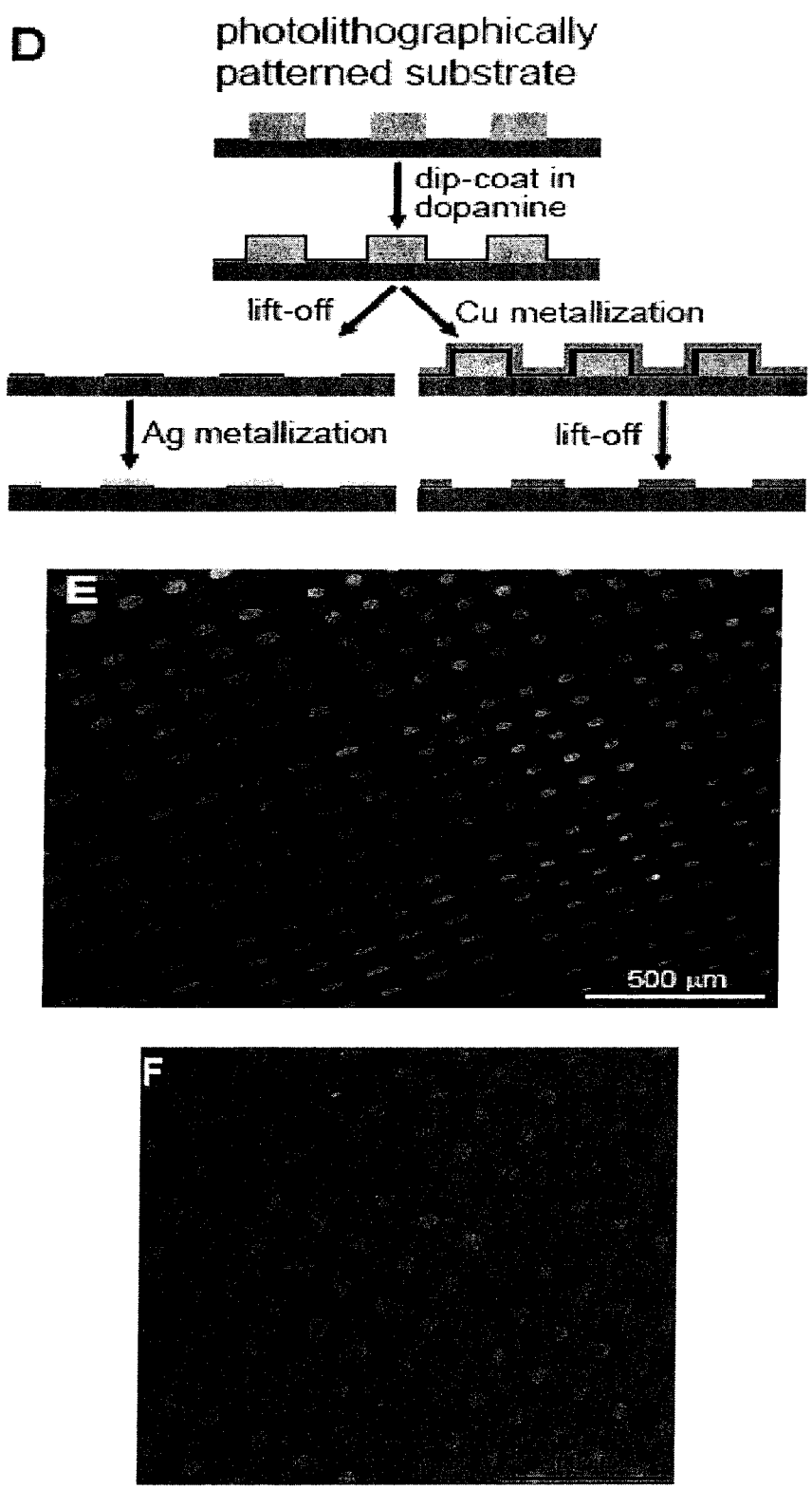
Figure 8A:
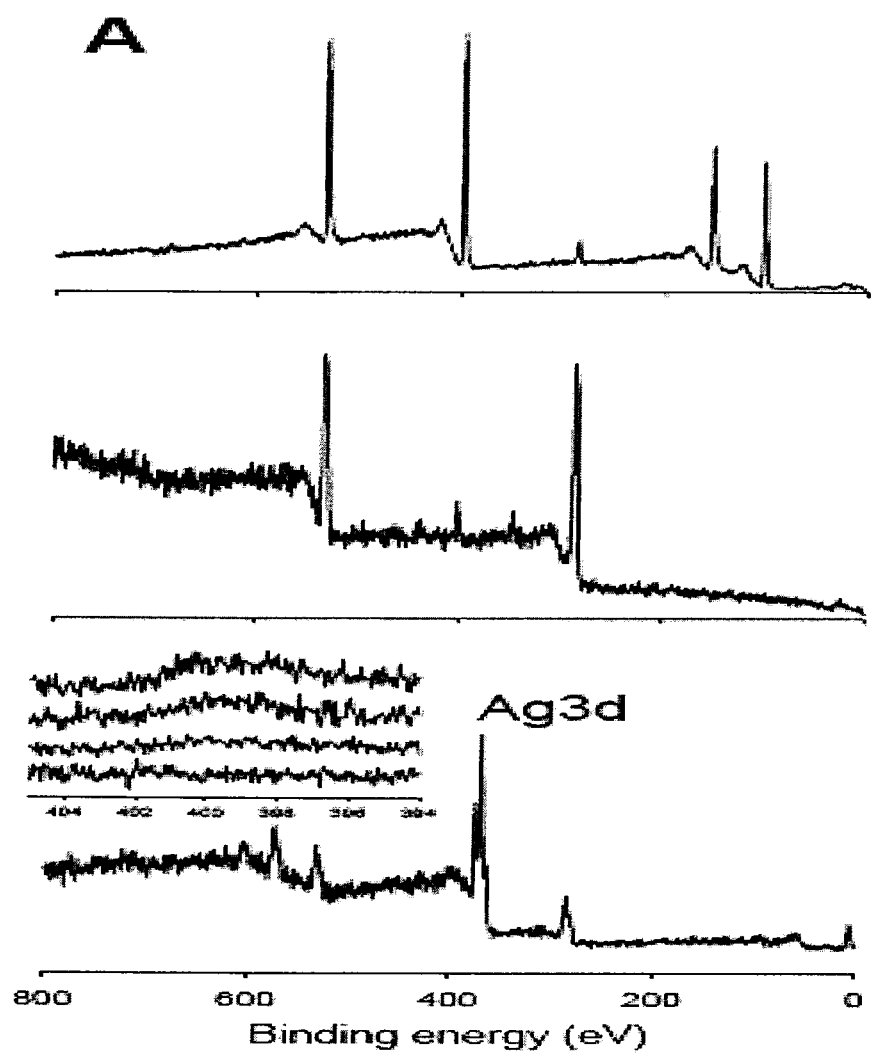
FIG. 8A. XPS spectra taken at each step of surface modification. (Top) Clean unmodified silicon nitride exhibited Si (2p=101.5 eV), N (1s=397.5 eV), and 0 (1s=532.5 eV) peaks. (Middle) Polydopamine-coated silicon nitride exhibited C, N, and O signals characteristic of polydopamine. (Bottom) The silver metal layer formed on polydopamine-coated silicon nitride, showing strong metallic Ag peaks ($3d_{512}$=368.6 eV; $3d_{312}$=374.7 eV) and minor hydrocarbon contamination. Inset: Angle-dependent (60, 45, 30, and 20 degrees from top to bottom). XPS showed no nitrogen is at take-off angles of 30 deg or less, confirming metallic silver ad-layer formation on top of polydopamine.
Figure 8B:
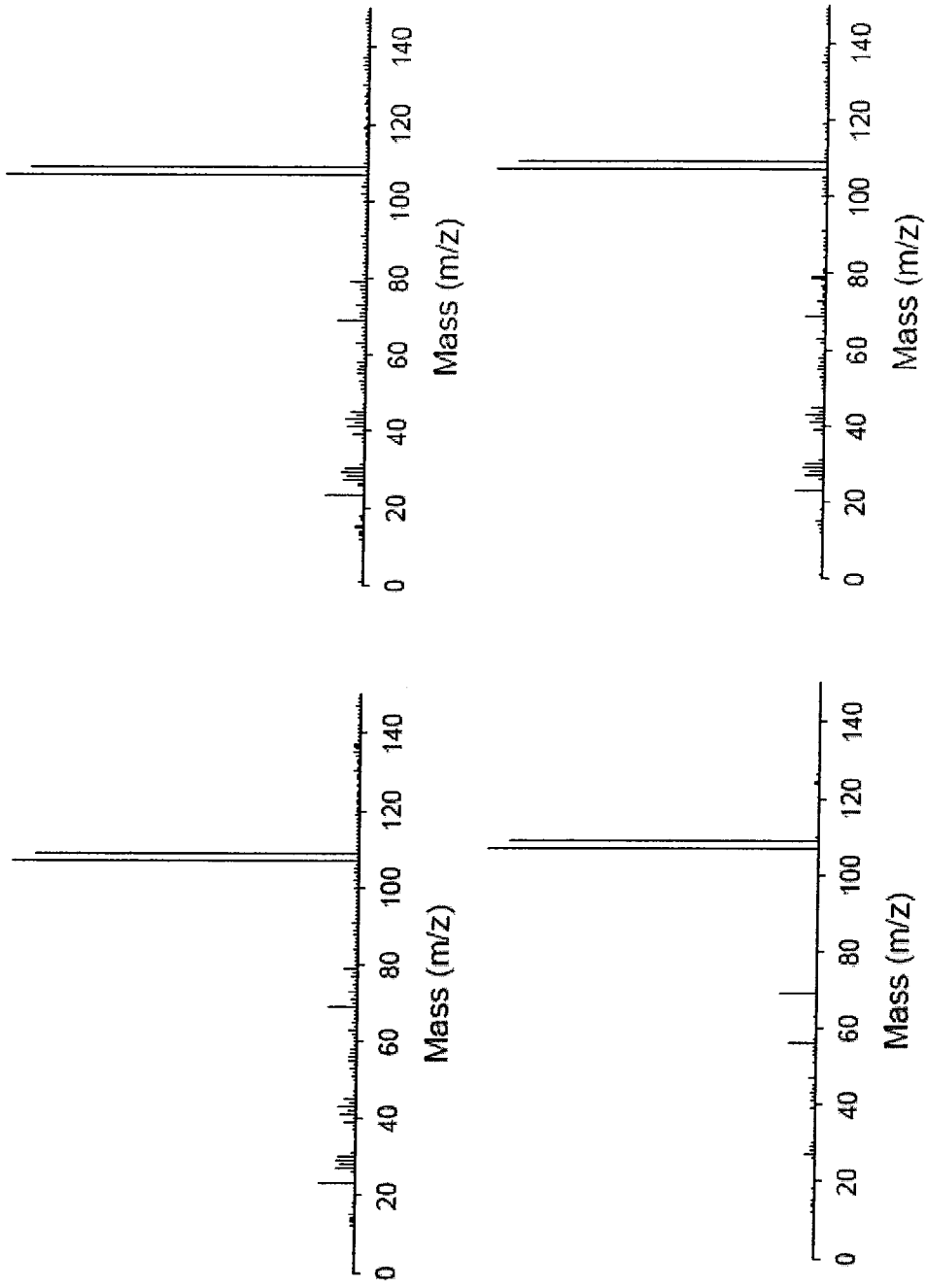
FIG. 8B. Electroless silver deposition on various substrates. Silver on glass (top left), gold (top right), Ti (bottom left), and PEEK (bottom right) showed nearly identical ToF-SIMS spectra in which two strong silver isotope peaks at 106.8 (theoretical 106.9) and 108.8 (theoretical 108.9) m/z were observed.
Figure 9:
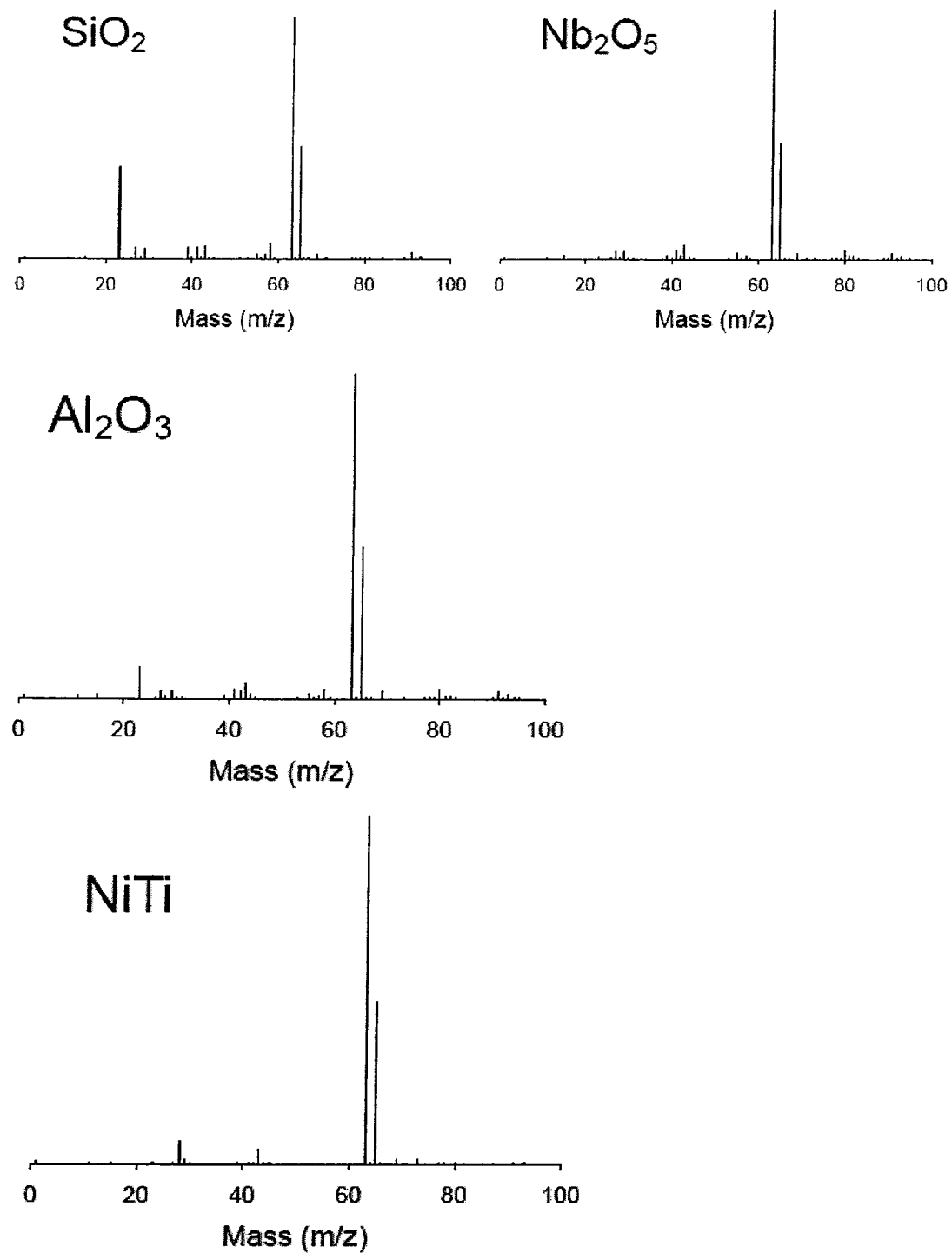
FIG. 9. ToF-SIMS characterization of copper ad-layer deposited by electroless metallization onto diverse polydopamine-coated substrates. All ToF-SIMS mass spectra were similar regardless of underlying substrates (62.9 and 64.9 m/z with an isotopic ratio of roughly 100% (62.9 m/z) to 40% (64.9 m/z)), indicating successful metallic copper deposition in a substrate-independent manner. The peak at 23 m/z was $Na^+$ contamination.
Figure 9:
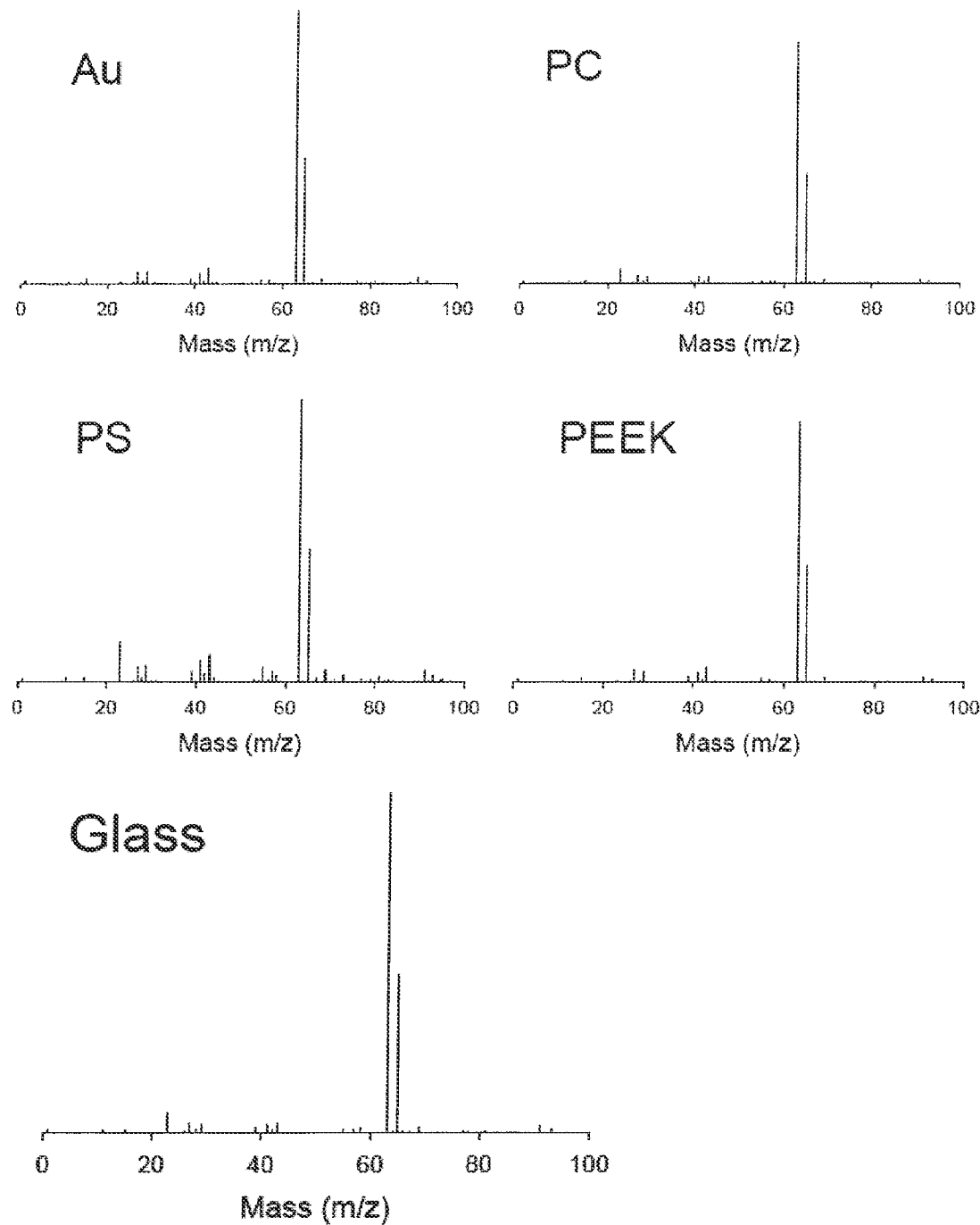
Figure 10:
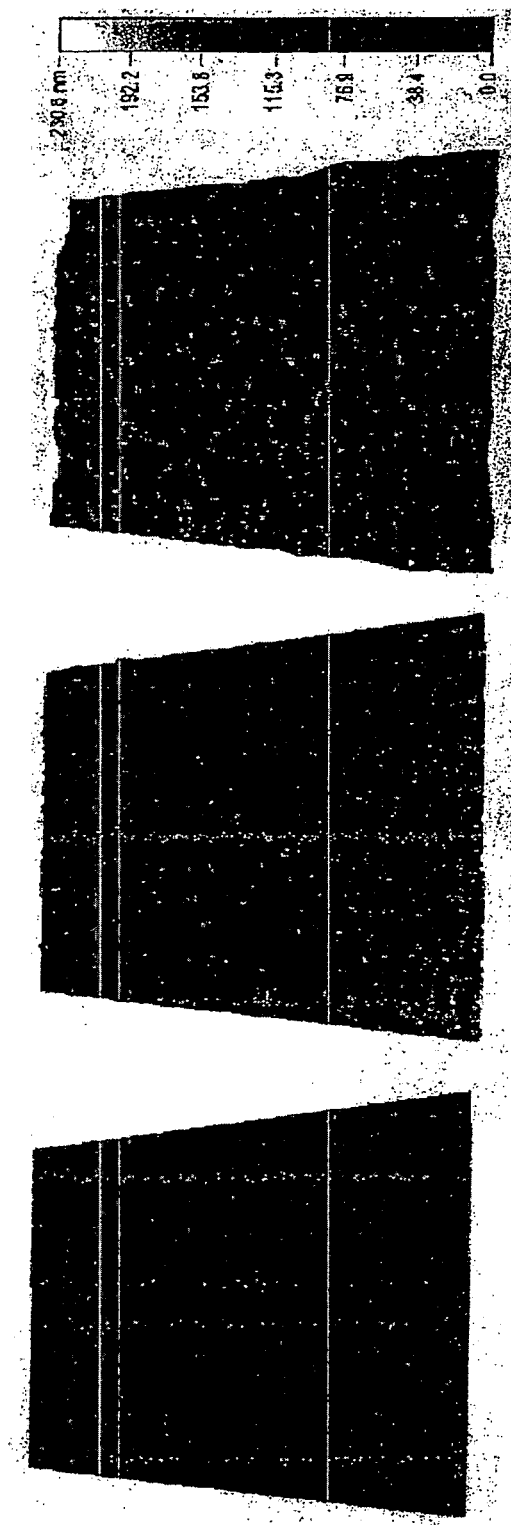
FIG. 10. Roughness analysis of polydopamine- and metallized polydopamine-coated substrates. The root mean square (RMS) roughness of $Nb_2O_5$, polydopamine-coated $Nb_2O_5$, and Cu-polydopamine-coated $Nb_2O_5$ was measured by AFM. The RMS roughness was 0.2 nm for bare $Nb_2O_5$ (left), 3.4 nm for polydopamine-coated $Nb_2O_5$ (middle), and 31.7 nm for Cu-polydopamine-coated $Nb_2O_5$ (right).

The metal binding ability of catechols present in the SMA's of the present invention was exploited to deposit adherent and uniform metal coatings onto substrates by electroless metallization. Silver and copper metal films were deposited on substrates by dip-coating SMA-treated substrates into silver nitrate and copper (II) chloride solutions, respectively (FIG. 7). Metal film deposition and roughness was confirmed by XPS and ToF-SIMS analysis, which demonstrated successful metal film deposition on a number of ceramic, polymer and metal substrates including nitrocellulose, coinage metals, commercial plastics, silicon nitride, glass, gold, titanium, Si, polycarbonate, polystyrene, PEEK, gold, niobium oxide, aluminum oxide, and nickel-titanium (FIGS. 8-10).

Metal coatings were also successfully applied in this manner to SMA-treated substrates including flexible polymer substrates and bulk objects with complex shapes (FIG. 7A-C), as well as flat substrates in which the SMA was patterned using standard photolithography techniques (FIG. 7D-F). Unlike many other approaches to electroless metallization, the use of (immobilized) colloidal metal seed particles was unnecessary for spontaneous formation of adherent metal films.

Surface-Independent Silver Deposition.

Silver has long been recognized as an anti-bacterial agent suitable for medical devices. Using the present invention, any underlying SMA-treated substrate can be modified to have silver metal layers. In the case of dopamine, silver metal layers can be formed solely by the redox power of the dopamine layer without a reducing agent. This implies that the underlying polydopainine coating on the substrate oxidizes during metal ion reduction. SMA-treated substrates were dipped into a 50 mM aqueous silver nitrate solution for eighteen hours (room temperature). Substrates were then washed with ultrapure water and dried with $N_2$ gas.

A series of XPS spectra showed clearly differentiated signals from silicon nitride (FIG. 8A, top), the polydopamine coating (middle), and electroless silver metallization afterward (bottom, reaction in 50 mM silver nitrate in water at room temperature) indicating layer by layer deposition at each step. Strong silver peaks ($Ag_{3d}$ 368.9 eV red line, FIG. 8A) were detected, completely suppressing a nitrogen signal from the underlying dopamine layer at a take-off angle of 20° (bottom inset).

Due to the surface-independent nature of the SMA-treated substrates described herein, virtually any substrate can be modified to include silver metallization. For instance, in addition to modifying silicon nitride, silver metal was successfully deposited on several representative substrates (FIG. 8B, glass (top left), gold (top right), Ti (bottom left) and PEEK (bottom right)). This was confirmed by the characteristic isotopic pattern (106.9 and 108.9 m/z) of silver mass in ToF SIMS.

In addition to the bulk electroless deposition, micropatterned silver deposition was acquired by photolithography followed by polydopamine-coating and silver metallization. The resulting silver pattern demonstrates that the metallization process described herein can be incorporated into conventional lithography processes. Additionally, the method described above provide an aqueous, cost effective and surface-independent preparation process that does not require toxic Pd/Sn colloids for catalysis. The method presented herein thus represents a significant advance in electroless silver deposition.

Surface-Independent Electroless Copper Metallization.

Using the method described herein, electroless copper metal plating was achieved on virtually all substrates, and was especially successful with synthetic polymer substrates. For instance, polyethylene terephthalate (PET) has been used for a substrate for flexible displays, an important commercial substrate for future electronic devices. Integrated copper circuit on PET substrates will supply power to organic light emitting diodes (OLED). Contacting PET substrates with dopamine followed by electroless copper plating is a simple and cost-effective method potentially revolutionizing integrated circuits.

The enediol group in dopamine has a strong affinity to various metals including copper so bound copper ions on the polydopamine-coated substrate act as seeds for subsequent metallization. Under a reducing condition, metal copper was successfully deposited on various substrates: Si, $Al_2O_3$, $Nb_2O_5$, NiTi, polystyrene, polycarbonate, polyetheretherketone, glass, and gold (FIG. 7). A micropatterning process was also developed to demonstrate a potential usage of circuit board applications on a hard substrate (glass, FIG. 7C) and a flexible substrate (cellulose acetate, FIG. 7D).

Figure 11:
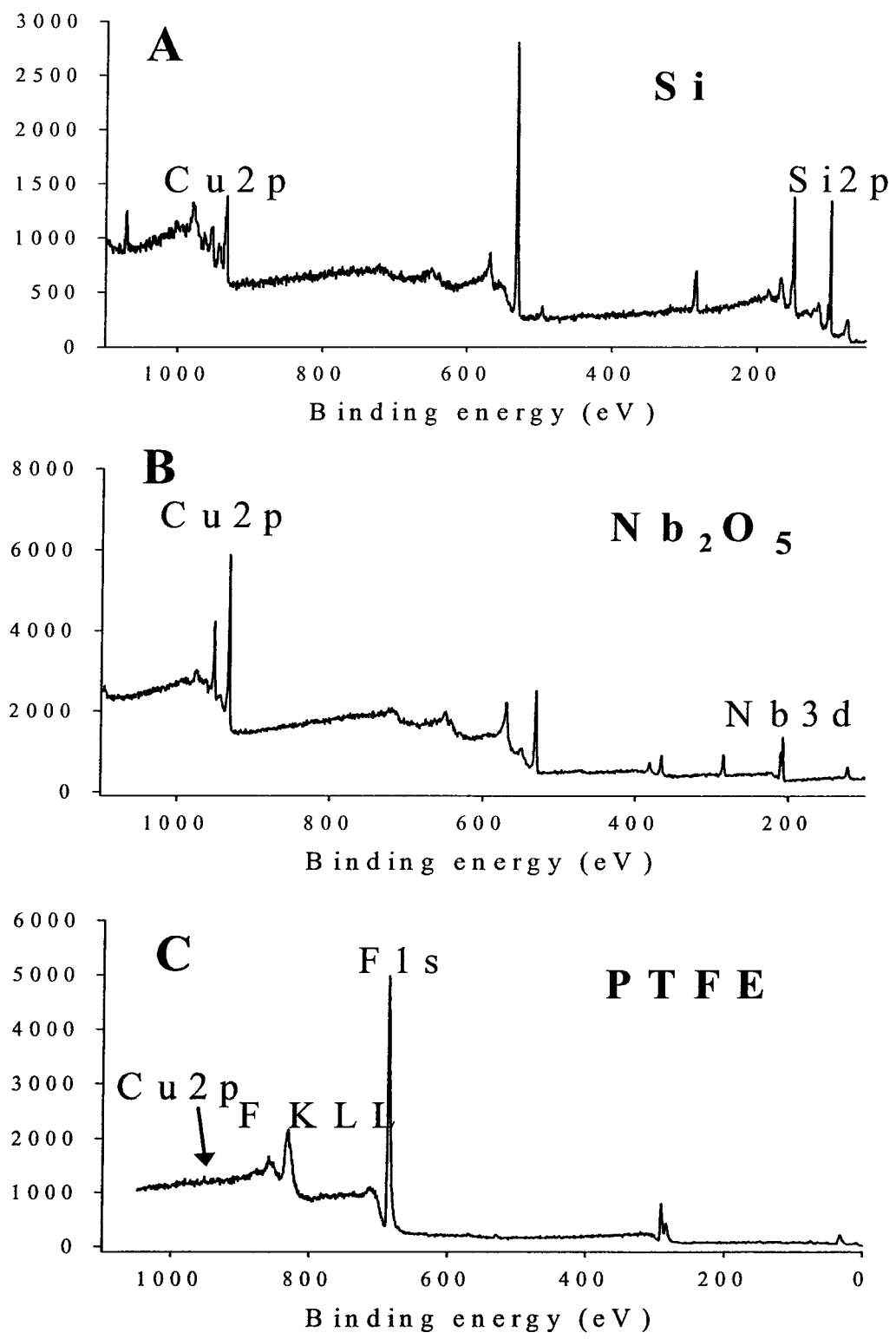
FIG. 11. Copper metallization in the absence of polydopamine-coated substrates. Copper metallization became inefficient without immobilized copper ions on polydopamine-coated substrates. Each tested substrate, silicon (A), niobium oxide (B), and polytetrafluoroethylene (PTFE) (C) showed different preferences for copper metallization without the polydopamine-coating. Metallic copper was barely detected on PTFE similar to unmodified substrates. Although the niobium oxide substrate exhibited good affinity to a copper layer, the niobium signals indicating that the Cu layer was not perfect. Silicon wafer revealed poor adhesion for newly formed metallic Cu layers showing a substrate Si2p signal.

The electroless copper deposition became ineffective without the SMA treatment, indicating the SMA-treated, substrate-bound copper plays a critical role in metallization. Substrates without SMA treatment showed strong substrate peaks: Si2p (103.3 eV) on Si, Nb (202.4 eV) on $Nb_2O_5$, and F1s (685 eV) on polytetrafluoroethylene indicating partial or no metallization (FIG. 11). SMA-treated substrates were metallized through immersion in copper (II) or silver salt solutions.

For electroless copper plating, a solution of 50 mM ethylenediaminetetraacetic acid (EDTA), 50 mM copper(II) chloride ($CuCl_2$), and 0.1 M boric acid ($H_3BO_3$) was prepared in ultrapure water, and the pH was adjusted to 7.0 using 1 N of NaOH. This solution can be stored in a refrigerator for future use. Immediately before use, 0.1 M dimethylamine-borane (DMAB) was added to the copper plating solution, after which the SMA-treated substrates were placed in the solution for two to three hours at 30° C. Substrates were then washed with ultrapure water and dried with $N_2$ gas.

Example 6

Biofouling and Biosensor Applications

Interfacial amino- or cysteinyl-dopamine coupling was performed by transferring pre-SMA-treated substrates to a monofunctional PEG solution (2 mg/mL methoxy-PEG-thiol or amine 5k (mPEG-SH, mPEG-$NH_2$) 10 mM Tris pH 8.5 50° C.). This simple two-step (SMA-treatment followed by PEGylation) aqueous chemistry successfully achieved universally-protein resistant substrates. The protein resistance capabilities were visualized at a resolution of a single molecule level using total internal reflection fluorescence (TIRF) microscopy.

Figure 12:
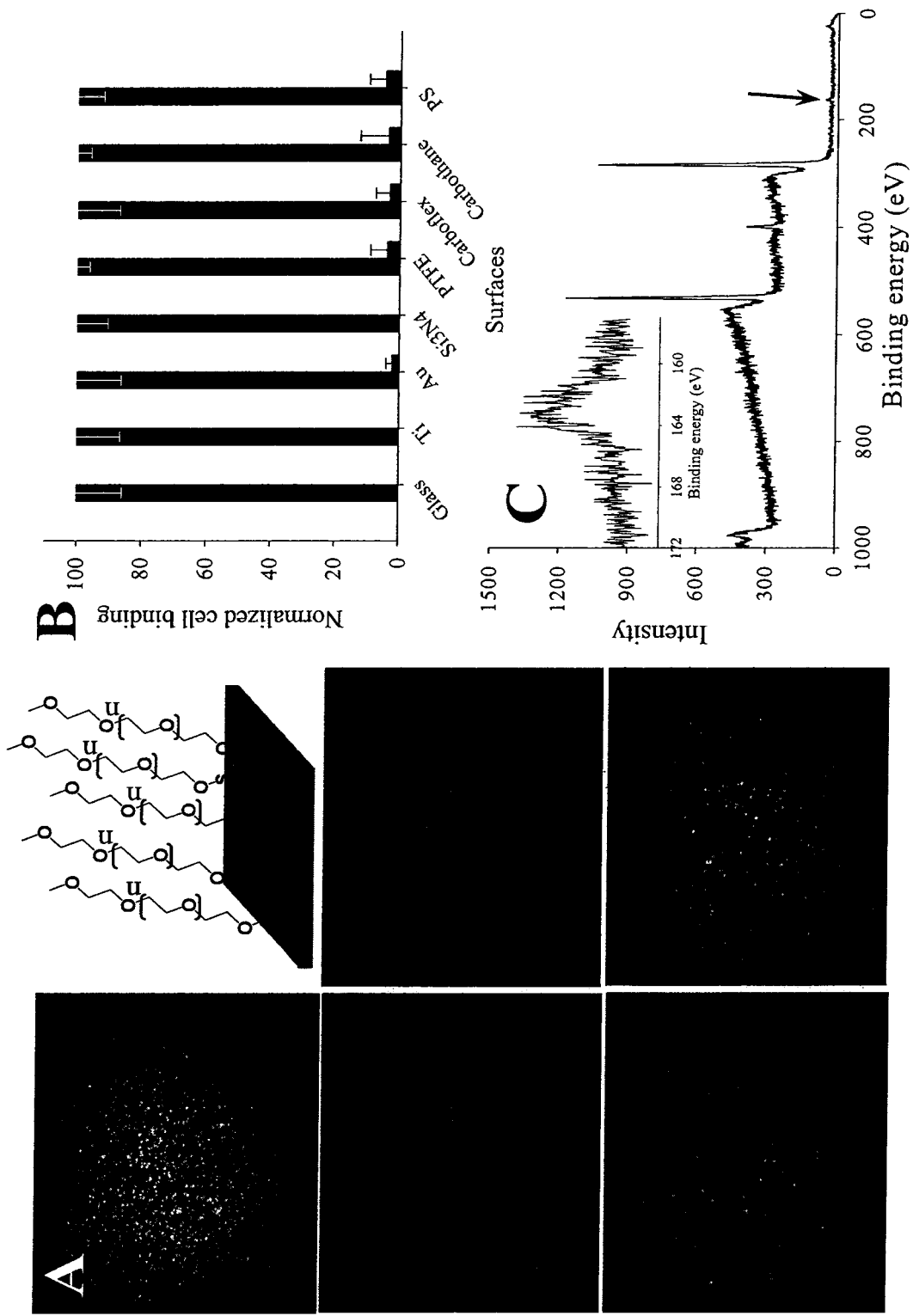
FIG. 12. Preparing surface-independent non-fouling (i.e., protein resistant) substrates.

Unmodified glass substrates upon exposure to proteins showed massive adsorption after 30 minutes (FIG. 12A, top), which was significantly improved by the traditional silane-PEG modification (bottom panel). However, long-term fouling resistance failed under the continuous exposure of a protein solution for 48 hrs (bottom right). SMA-treated substrates modified in a secondary reaction to contain PEG (mPEG-$NH_2$, 5 kDa) exhibited excellent antifouling properties showing incredible short- (30 min) and long-term (48 hrs) stability with virtually no defect (middle left and right respectively).

In the focal area, only fourteen proteins were detected on the SMA-treated, PEG-modified glass substrate, whereas approximately 400 proteins were adsorbed on silane-PEG modified substrates after 48 hrs. This demonstrates the enormously advantages of the present invention.

The proteins resolved by TIRF microscopy correspond to 0.01 pg/$cm^2$ which is below the lowest limit (approximately 1 ng/$cm^2$) of common surface analytical tools such as surface plasma resonance spectroscopy or optical waveguide light spectroscopy. Thus, PEGylated non-fouling substrates can be prepared in a surface-independent way. For non-transparent substrates, the four-hour fibroblast binding assay was used instead of TIRF microscopy (see Example 10). Also, the assay of cell binding resistance is an important criterion to examine antifouling performance of substrates in vitro.

All substrates tested, including oxide (Ti), metal (Au), semiconductor ($Si_3N_4$), polymer (polytetrafluoroethylene (PTFE), polyurethanes (tecoflex®, carbothane®)) and ceramic (glass) substrates exhibited excellent antifouling properties (FIG. 3B). The thiol end group of the PEG chain (mPEG-SH, 5 kDa) in this experiment was used for an elemental probe in X-ray photoelectron spectroscopy (XPS). Sulfur 2p (163 eV) orbital signal was clearly observed (FIG. 12C), demonstrating successful interfacial PEG conjugations.

Example 7

SMA-Assisted SAM formation

For alkanethiol ad-layer formation, 5 mM of dodecanethiol (Sigma-Aldrich, Milwaukee, Wis.), 1-mercapto-11-undecyl tri(ethylene glycol) (0EG3-C11-SH), or OEG6-C11-SH (Asemblon Inc, Redmond, Wash.) was dissolved in dichloromethane (DCM) which was pre-equilibrated by bubbling with He or $N_2$. SMA-treated substrates (SMA according to Formula II) were subsequently added followed by triethylamine (final concentration 10 mM). After five hours or more (typically overnight reaction for eighteen hours), the SMA-treated substrates were rinsed by either DCM or ethanol and dried with nitrogen.

An alkanethiol monolayer was spontaneously formed through simple immersion of the SMA-treated substrates (FIG. 13B). Monolayer formation on the polydopamine sublayer is believed to involve reaction between terminal thiol groups and the catechol/quinone groups of the polydopamine coating of the substrate in a manner analogous to the reaction between thiols and noble metal films in the formation of conventional SAMs. Alkanethiol monolayers formed by this approach (referred to herein as "pseudo-SAMs" or "pSAMs") appear to be functionally similar to conventionally formed SAMs.

Figure 14:
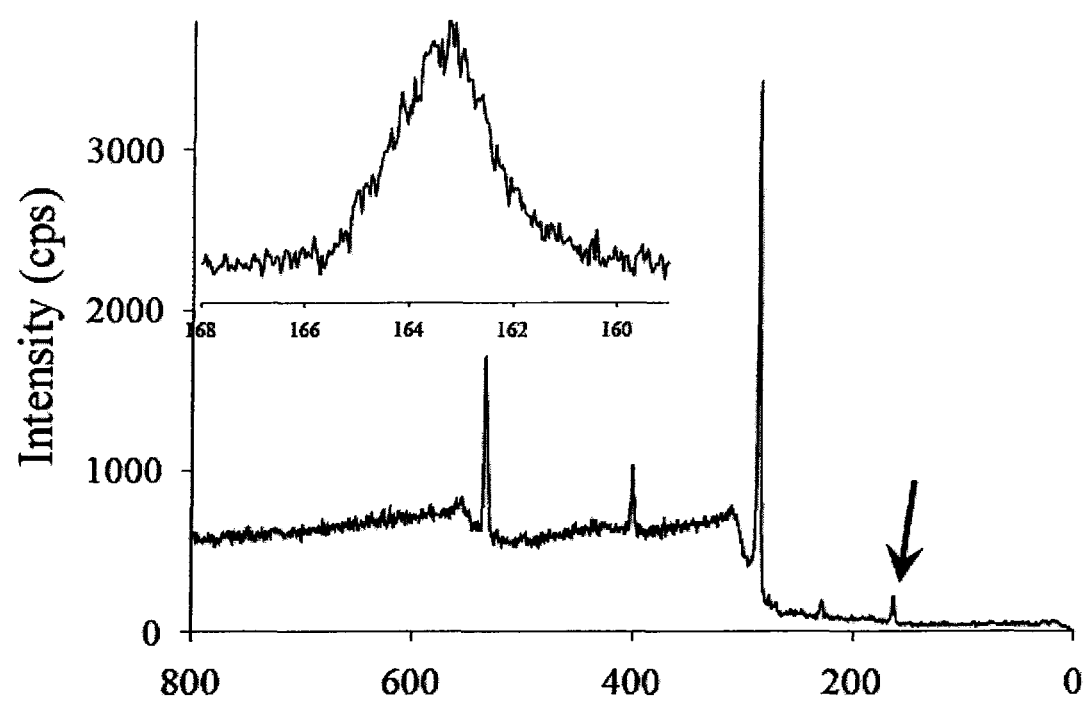
FIG. 14. XPS analysis of self-assembled monolayer formed on polydopamine-coated polycarbonate. XPS survey spectrum after reaction between dodecanethiol and polydopamine-coated polycarbonate. Arrow represents the sulfur 2p (163 eV) signal derived from the surface immobilized dodecanethiol molecules. Inset shows the high-resolution spectrum of the sulfur 2p region marked by the arrow.

For example, spontaneous formation of pSAMs using methyl-terminated alkanethiol (C12-SH) was suggested by water contact angles of greater than 100° (FIG. 13B, Table 3) and XPS spectra revealing the presence of sulfur in the modified substrates (FIG. 14). Table 3 describes the evolution of contact angles of SAMs formed on various polydopamine-coated substrates. $0_{stat}$ and $0_{stat}$ are advancing and static contact angles, respectively. The average contact angles of polydopamine-coated and SAM-formed substrates are shown in the last row. pSAMs were formed in this way on at least seven different materials including several ceramics and polymers.

TABLE 3

| | Bare $\theta_{adv}$ ($\theta_{stat}$) | Polydopamine $\theta_{adv}$ ($\theta_{stat}$) | SAM $\theta_{adv}$ ($\theta_{stat}$) |
|---|---|---|---|
| PTFE | 115 (106) | 60 (49) | 111 (102) |
| PC | 103 (96) | 54 (42) | 104 (96) |
| NC | 95 (84) | 53 (41) | 118 (106) |
| SiO$_2$ | 21 (<10) | 66 (54) | 101 (92) |
| TiO$_2$ | 22 (<10) | 63 (51) | 103 (94) |
| Cu | 88 (78) | 55 (43) | 119 (109) |
| Au | 68 (54) | 57 (46) | 101 (90) |
| Average | — | 58 (47) | 108 (98) |

Example 8

PEG Grafting

Figure 15:
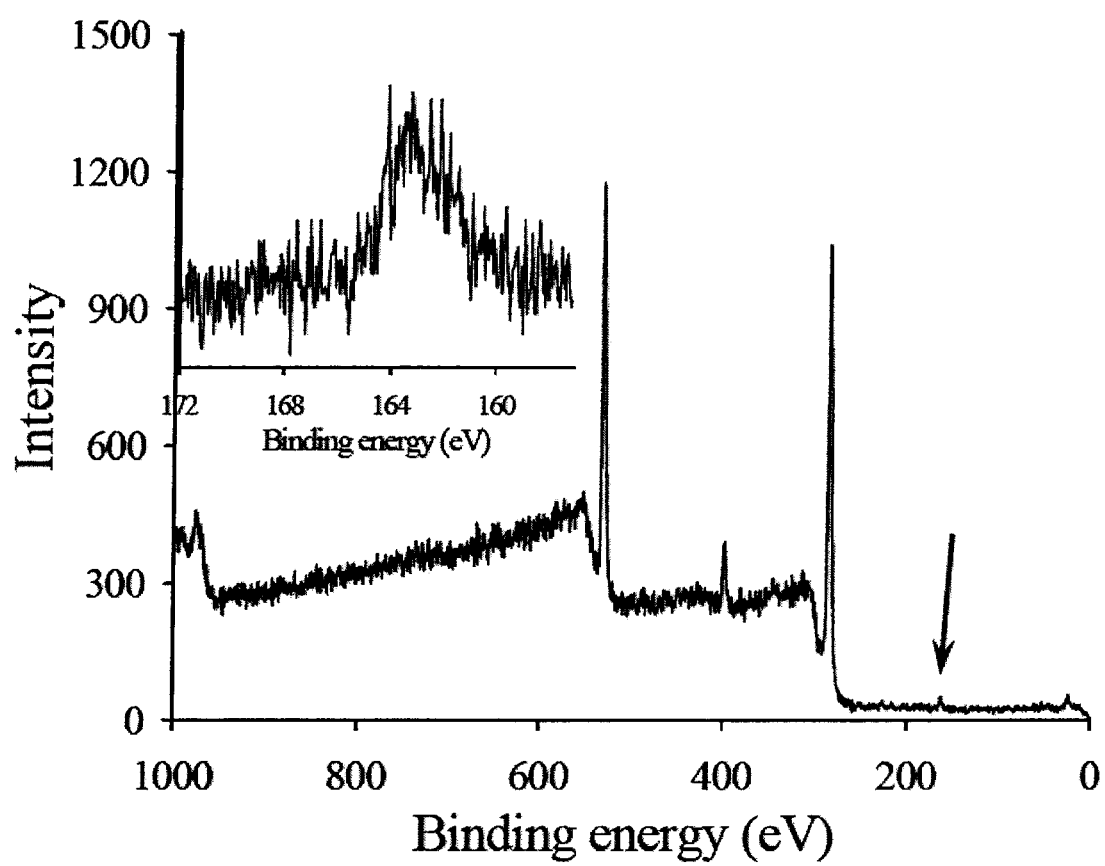
FIG. 15. XPS analysis of PEG grafted onto polydopamine-coated glass. XPS survey spectrum after reaction between mPEG-SH and polydopamine-coated glass. Arrow represents the sulfur 2p (163 eV) signal derived from the surface-immobilized mPEG-SH molecules. Inset shows the high-resolution spectrum of the sulfur 2p region marked by the arrow.

In this example, at least a portion of a substrate was contacted with dopamine to form a reactive, SMA-treated substrate which was contacted with a secondary reactive moiety to form fouling-resistant surfaces. Specifically, fouling-resistant substrates were made by covalently grafting amine- or thiol-terminated methoxy-poly(ethylene glycol) (mPEG-NH$_2$ or mPEG-SH in 10 mM Tris, pH 8.5, 50° C.) to the polydopamine-coated substrate surface (FIG. 15).

For PEG grafting, 5 mg/mL of methoxy-poly(ethylene glycol)-thiol (mPEG-SH, 5 kDa, SunBio, Ahn-Yang, South Korea) or methoxy-poly(ethylene glycol)-amine (mPEG-NH$_2$, 5 kDa, Nektar, San Carlos, Calif.) was dissolved in 10 mM Tris pH 8.0 or sodium phosphate buffer pH 8.0. The buffer used for mPEG-SH was vacuum degassed for more than one hour to prevent oxidation (—S—S—) between thiol groups.

mPEG-NH$_2$-modified, polydopamine-coated glass substrates exhibited substantial reduction in nonspecific protein adsorption compared to uncoated glass, and also outperformed glass substrates modified by a silane-terminated PEG in terms of fouling resistance after two days of continuous exposure to protein solution (FIG. 13D-F). Similarly, mPEG-SH grafting onto a variety of polydopamine-coated substrates led to dramatic reduction of fibroblast cell attachment compared to the unmodified substrates (FIG. 13G, Table 4). The polydopamine coating itself was supportive of fibroblast cell adhesion at a level similar to bare substrates (for example, the total area of attached cells on polydopamine modified SiO$_2$ (46±1.4×10$^3$ µm$^2$) was similar to unmodified SiO$_2$ (55±8.6× 10$^3$ µm$^2$)), leading to the conclusion that the observed decrease in cell adhesion was due to the grafted mPEG-SH.

Example 9

SMA-Treated Substrates Having Flagella Labeling

Figure 16:
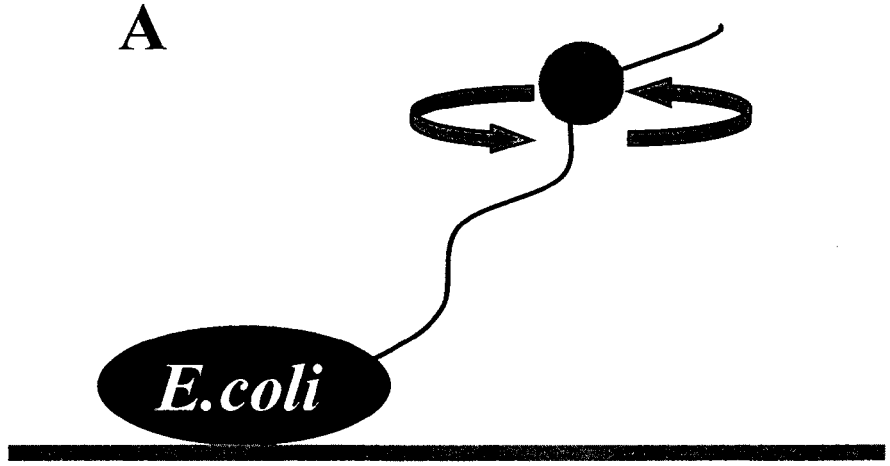
FIG. 16. Chemically 'active' coating targeting cellular proteins for the study of bacterial chemotaxis.
Figure 16:
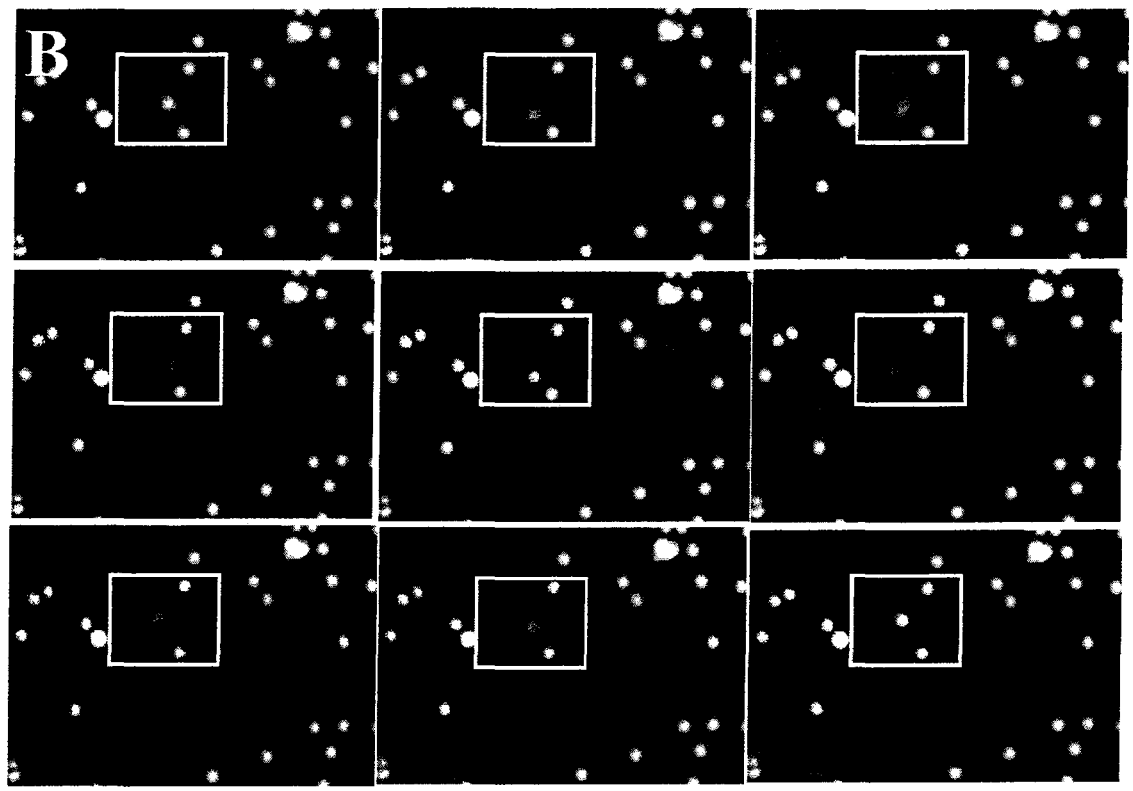

In this example, latex beads were contacted with an aqueous, alkaline solution of dopamine as described in Example 1. The latex beads (1 µm in diameter) were spread onto pre-adsorbed E. coli, resulting in one bead attached to a flagella protein (presumably via N-terminus and lysine residues) as evidenced by the counterclockwise rotation of the flagella (FIG. 16, box). The dots represent an individual bead non-specifically adsorbed onto the glass surface showing no spatial movement.

Example 10

Short-Term (4 hr) Fibroblast Adhesion

NIH 3T3 fibroblasts (ATCC, Manassas, Va.) were maintained at 37° C. with 5% CO$_2$ in Dulbecco's Modified Eagle's medium (DMEM, Cellgro, Herndon, Va.) containing 10% fetal bovine serum (FBS, ATCC, Manassas, Va.) and 100 µg/ml of penicillin and 100 µm' of streptomycin. Trypsinized cells were resuspended in DMEM with 10% FBS and then counted for sub-cultures and/or seeded onto the test substrates at a cell density of 5.0×10$^3$ cells/cm$^2$. After 4 hrs, cells were stained with 2.5 pM Calcein-AM (Molecular Probes) in complete PBS for one hour at 37° C. culture. Cell attachment was quantified by acquiring nine images from random locations of each substrate using a fluorescence microscope (Olympus BX-40, $2_{ex}$=549 nm, $X_{em}$=565 nm) equipped with a CCD camera (Roper Scientific, Trenton, N.J.). Finally, the resulting images were processed using Metamorph software (Universal Imaging, Downington, Pa.).

TABLE 4

| Substrates | # of cells (bare) | # of cells (PEG-polydopamine) |
|---|---|---|
| Glass | 68.7 ± 14 | 0 ± 0 |
| TiO$_2$ | 72.1 ± 13 | 0 ± 0 |
| Au | 62.9 ± 14 | 1.3 ± 1 |
| Si$_3$N$_4$ | 57.1 ± 9 | 0 ± 0 |
| PTFE | 7.8 ± 4 | 0.2 ± 0.4 |
| PU1 | 16.9 ± 13 | 0.6 ± 0.7 |
| PU2 | 15.1 ± 4 | 0.6 ± 1.3 |
| PS | 23.6 ± 8 | 1.1 ± 1.6 |

Example 11

SMA-Assisted Grafting of Hyaluronic Acid

Figure 17:
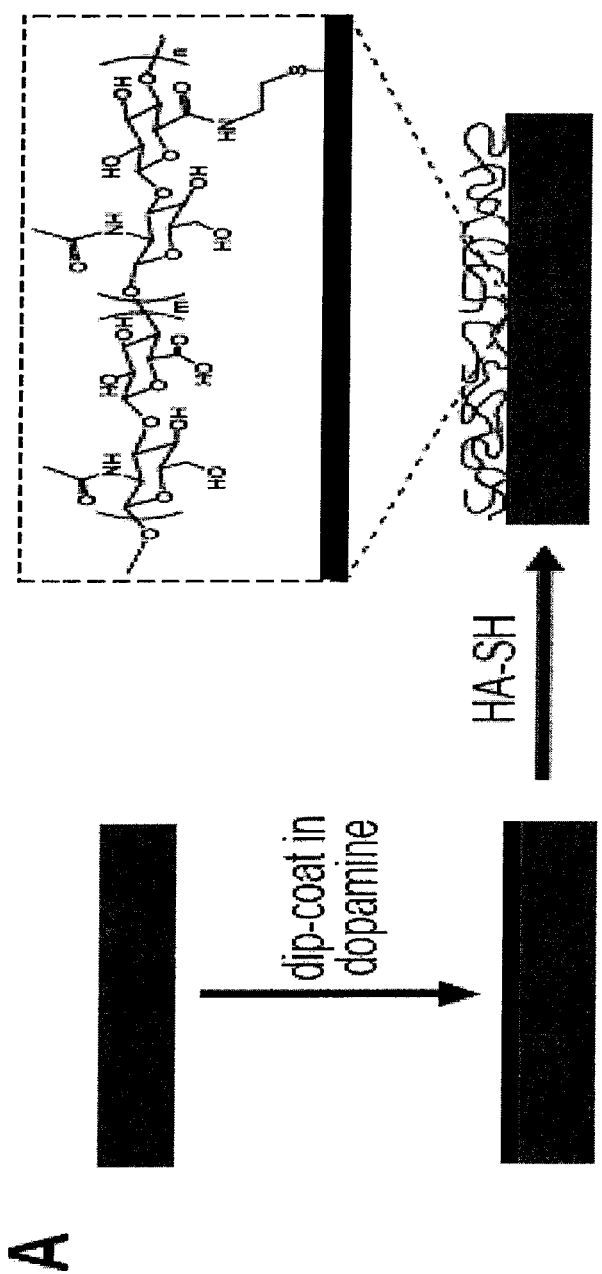
FIG. 17. Polydopamine-assisted grafting of a biomacromolecule for biospecific cell interaction.
Figure 17:
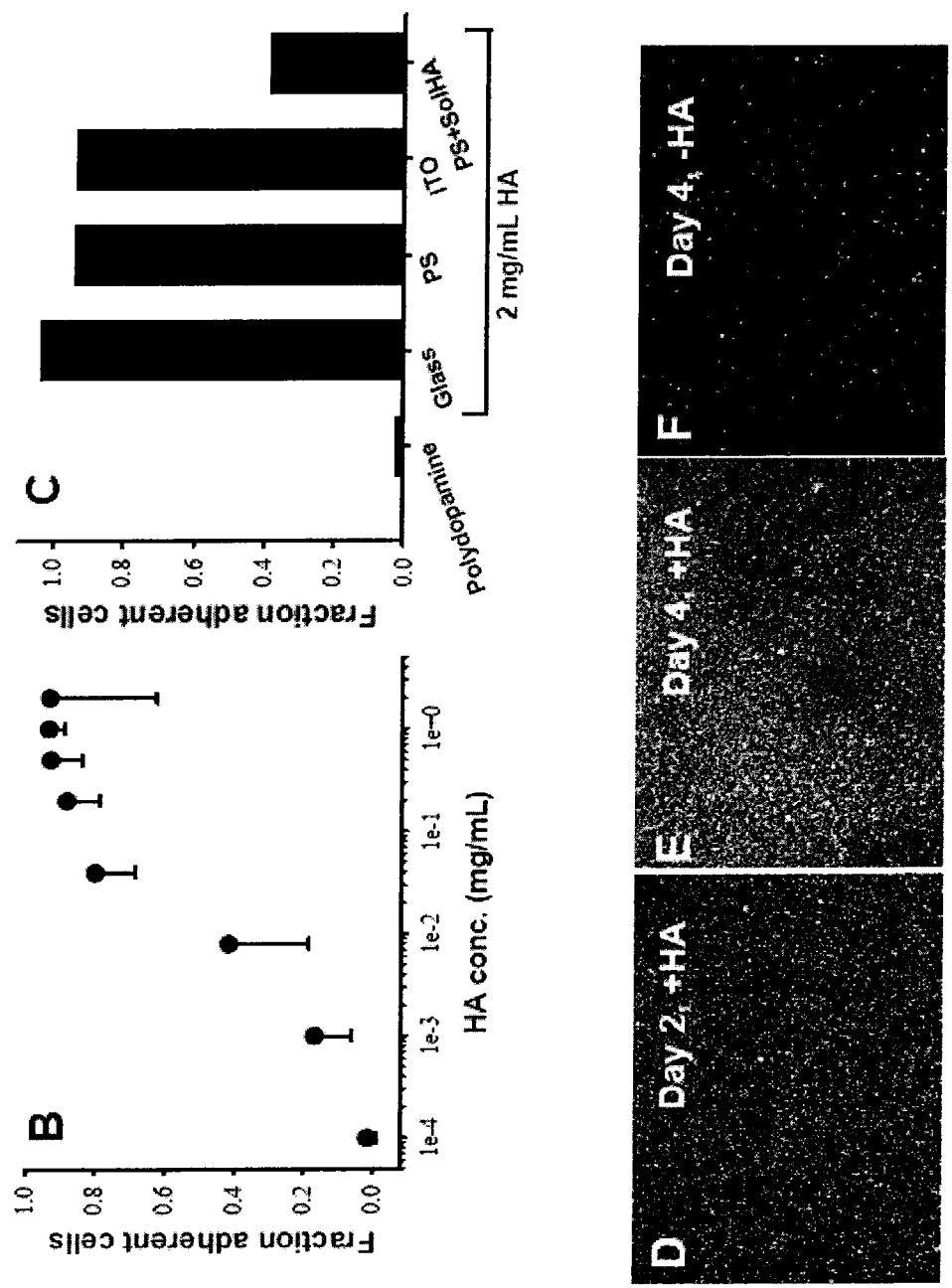

Ad-layers of the glycosaminoglycan hyaluronic acid (HA) were added to SMA-treated substrates prepared according to Example 1 for specific biomolecular interactions. HA/receptor interactions are important for physiological and pathophysiological processes including angiogenesis, hematopoietic stem cell commitment and homing, and tumor metastasis. Partially thiolated HA was grafted onto a variety of SMA-treated substrates (FIG. 17) and HA ad-layer bioactivity was measured via adhesion of the human megakaryocytic M07e cell line. Unlike fibroblasts, M07e cells did not adhere to polydopamine but did adhere to HA-grafted polydopamine-coated substrates in a dose dependent manner (FIG. 17B).

Figure 18:
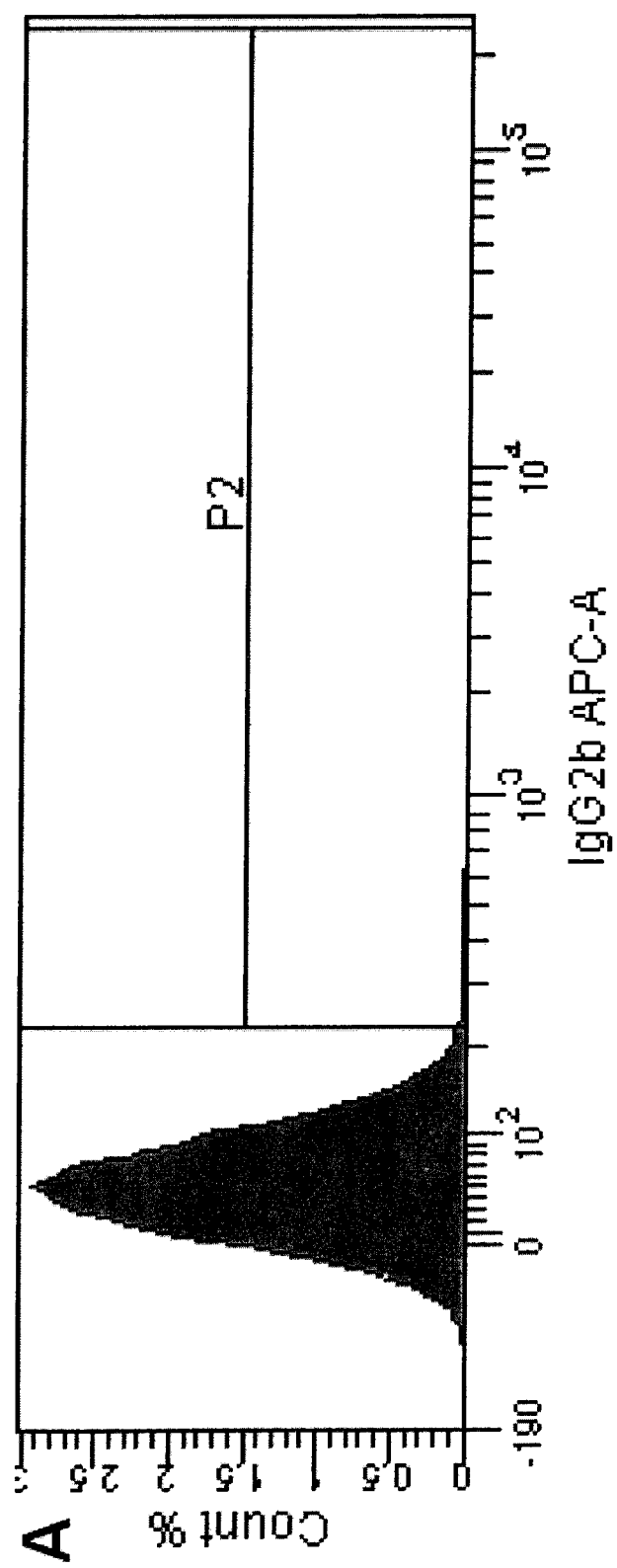
FIG. 18. Flow cytometry analysis of CD44 levels on M07e cells. M07e cells were stained with either isotype control-APC (A) or anti-CD44-APC (B) antibodies to determine the surface expression of CD44 receptors. The fraction of cells expressing CD44 was determined by quantifying the number of cells within the sample having fluorescence intensity greater than isotype-control-stained cells (P2=99.4% for CD44-APC stained cells). Data are representative of two independent experiments.
Figure 18:
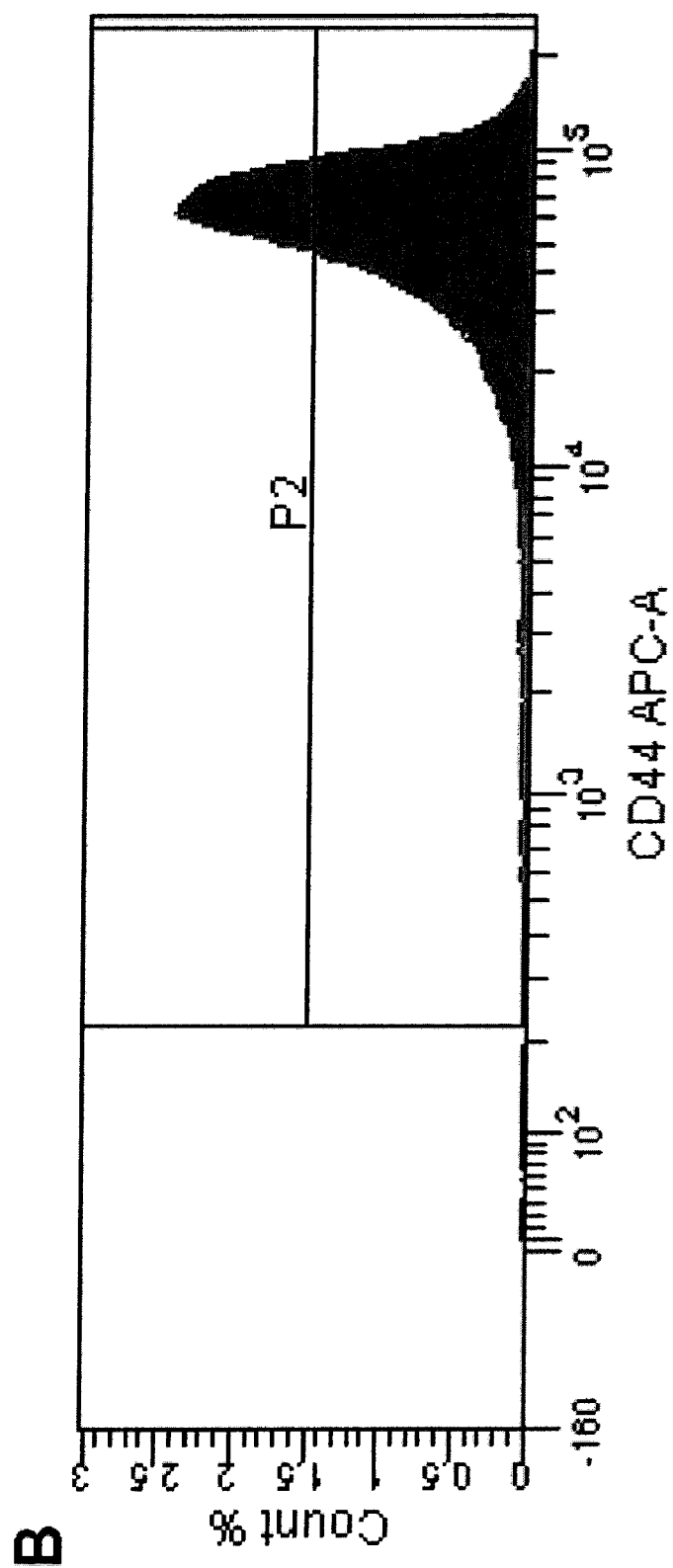
Figure 19:
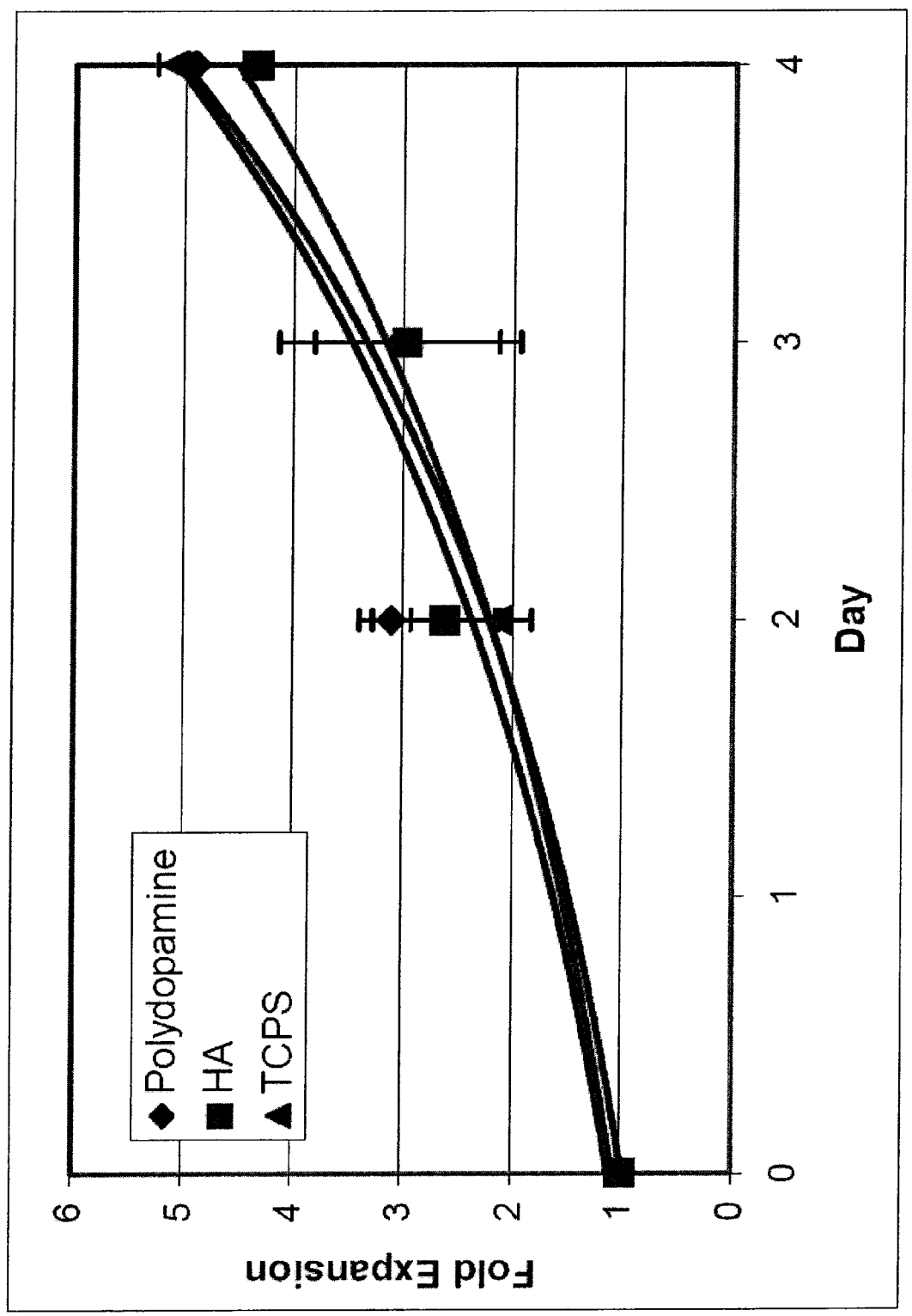
FIG. 19. M07e cell expansion on TCPS, polydopamine, and HA-polydopamine substrates. Similar cell expansion was observed on all three substrates. Curves are best-fit exponential and error bars show standard deviation. Represents average of thirteen experiments/timepoints.

Together with decreased binding in the presence of soluble HA (FIG. 17C), these findings are consistent with expression of the HA receptor CD44 by M07e cells (FIG. 18). Polydopainine and HA-grafted polydopamine-coated substrates were biocompatible as evidenced by similar levels of M07e cell expansion compared to tissue culture polystyrene, although only the HA-grafted polydopamine-coated substrates supported cell adhesion (FIG. 170D-F; FIG. 19).

17 kDa HA (Lifecore, Chaska, Minn.) was thiolated using a previously published protocol (Lee et al., *Macromolecules* 39, 23 (2006)). The modified HA had approximately 50% substitution (by NMR) with thiol groups. Thiolated HA (0.001-2 mg/mL in de-oxygenated 10 mM Tris buffer, pH 8.0) was reacted with polydopamine-coated substrates for typically overnight to yield HAfunctionalized substrates. HA-tethered, polydopamine-coated glass or indium-tin oxide (ITO) substrates were attached to a bottomless sixteen-well chamber slide (Nunc, Rochester, N.Y.) via the injection of a self-curing silicone rubber (Silastic® Dow Corning) gasket. For TCPS, standard ninety six-well plates were used, and the polydopamine coating and HA ad-layer formation steps were performed sequentially in each well. (Please note that the polydopamine coating and HA ad-layer formation can also be performed simultaneously in each well.)

M07e Cell Culture.

M07e cells (DMSZ, Germany) were adapted to grow in IMDM (Sigma) supplemented with 2.5% FBS (Hyclone), 10 ng/mL GM-CSF (Berlex Laboratories), and 1 mg/mL gentamicin sulfate (Sigma). Cells were maintained in exponential growth phase between $5\times10^5$ and $1\times10^6$ cells/mL. Normal-force cell adhesion assays were performed as previously described (Jensen et al., *J. Am. Chem. Soc.* 126, 15223 (2004)). Briefly, M07e cells were stained with 5 ti·g/mL Calcein AM in PBS and incubated in normal growth media on substrates for two hours prior to removing non-adherent cells by inverted centrifugation at 30 rcf in sealed bags filled with PBS. Image analysis of pre- and post-spin images was used to calculate the percent cell adhesion. Substrates for extended cell culture were sterilized with short-wave UV light for thirty minutes prior to seeding cells in normal growth medium at a density of $3.75\times10^5$ cells/mL. Adhesion was measured on days 2 and 4 using the normal-force cell adhesion assay. However, in this case the cells were stained directly in the wells via addition of 40 uL of Calcein AM (diluted to 5 pg/mL PBS) thirty minutes prior to pre-centrifugation imaging. For HA competition, soluble 17 kDa HA was incubated with M07e cells for thirty minutes at 37° C. prior to loading onto HA-grafted, polydopamine-coated wells. For the M07e cell expansion assay, cell density was measured by total nuclei counts in a solution of hexadecyltrimethylammoniumbromide (Sigma; 30 g/L), sodium chloride (8.33 g/L) and EDTA (366.25 mg/L) with a Coulter Multisizer.

Flow Cytometry Analysis of CD44 Levels on M07e Cells.

To determine the expression levels of the HA receptor CD44, M07e cells were washed with PBS containing 1 g/L sodium azide and 0.5% bovine serum albumin. Allophycocyanin (APC)-conjugated mouse anti-human-CD44 antibody or APCconjugated isotype control mouse-$IgG_{2b}$,x antibody (Becton Dickinson) were incubated with the cells for thirty minutes at room temperature. After washing, cells were analyzed on a Becton Dickinson LSRII flow cytometer using FACSDiva software (Becton Dickinson).

Example 12

SMA-Assisted Metal Removal

Twenty mg of dopamine hydrochloride and 1 g of beads were added to 20 ml of pH 8 10 mM Tris buffer. The solution was put on the rocker for three hours for dopamine coating. A column of SMA-treated beads was prepared according to Example 1 and DI water was used to remove excess dopamine hydrochloride. 4.5 ml of metal solution was added to the column. The solution was put on the rocker for certain time to react, and then the filtrate was collected. The concentration of the filtrate was measured using ICP-AES.

Results can be seen in Table 5. Cr, Hg, and Pb showed great affinity for binding to polydopamine-coated beads. Cu showed relatively weak binding. Cd, Ba, and Se showed no affinity for binding. The last three tests on Cr, Hg, and Pb were conducted to see if the SMA-treated beads of the present invention could effectively remove the metal ions at low concentration, and the metal ion concentrations after binding can fall below the MCLs. When measuring such low concentrations, detection limit of the metal ion with ICP-AES and reliability of the data should be considered. ICP-MS can also be used to measure low concentrations. Generally, it falls within the detection limit when it shows a clear intensity peak for a certain concentration of metal ion. Further, the data is reliable when a fit standard can be generated.

For Cr, the data show that its concentration after binding fell below the MCL. The intensity peak for the sample was clear. Thus, polydopamine-coated beads effectively removed Cr to below the MCL. For Pb, the data show that its concentration after binding, although very close, did not fall below the MCL. Further experiments were conducted to test the accuracy of this data.

Hg is the most difficult metal species for ICP-AES to accurately measure the concentration. In ICP-AES, their intensity peaks tend to fluctuate even for the same sample. When measuring fractions of ppm, slight changes in intensity can lead to relatively large change in the calculated concentration. Overall, the data presented herein illustrate that polydopamine-coated substrates can be used to remove metals such as Cr, Hg and Pb from water. An increase in the amount of polymer in the polymeric-coated substrate may likely to reduce the final concentration to below the MCL values for each.

TABLE 5

| Metal (reaction time[1]) | Conc. of added metal solution (ppm) | Conc. without Binding[2] | Conc. Measured (ppm) | MCL[3] (ppm) |
|---|---|---|---|---|
| Cu (overnight) | 10 | 5 | 4.16 | 1.3 |
| Pb (overnight) | 10 | 5 | 2.42 | 0.015 |
| Hg (2 hr) | 10 | 5 | 1.1 | 0.002 |
| Hg (overnight) | 10 | 5 | 1.01 | 0.002 |
| Cr (1 hr) | 10 | 5 | 0.57 | 0.1 |
| Cd (1 hr) | 10 | 5 | 4.85 | 0.005 |
| Se (1 hr) | 10 | 5 | 5.22 | 0.05 |
| Ba (1 hr) | 10 | 5 | 5.22 | 2 |
| Cr (1 hr) | 1 | 0.5 | 0.02 | 0.1 |
| Pb (1 hr) | 1 | 0.5 | 0.031 | 0.015 |
| Hg (1 hr) | 1 | 0.5 | 0.17 | 0.002 |

[1]Reaction time indicates Step 4 in the procedure.
[2]"Concentration without Binding" was obtained from a prediction that 1 g of beads hold about 4.5 mL of water and additional 4.5 mL of metal solution should make the overall concentration half the concentration of the added metal solution.
[3]MCL stands for Maximum Contaminant Level for drinking water set by U.S. Environment Protection Agency.

Example 13

SMA-Treated Substrates Surface Conjugation of poly-L-histidine

Figure 20:
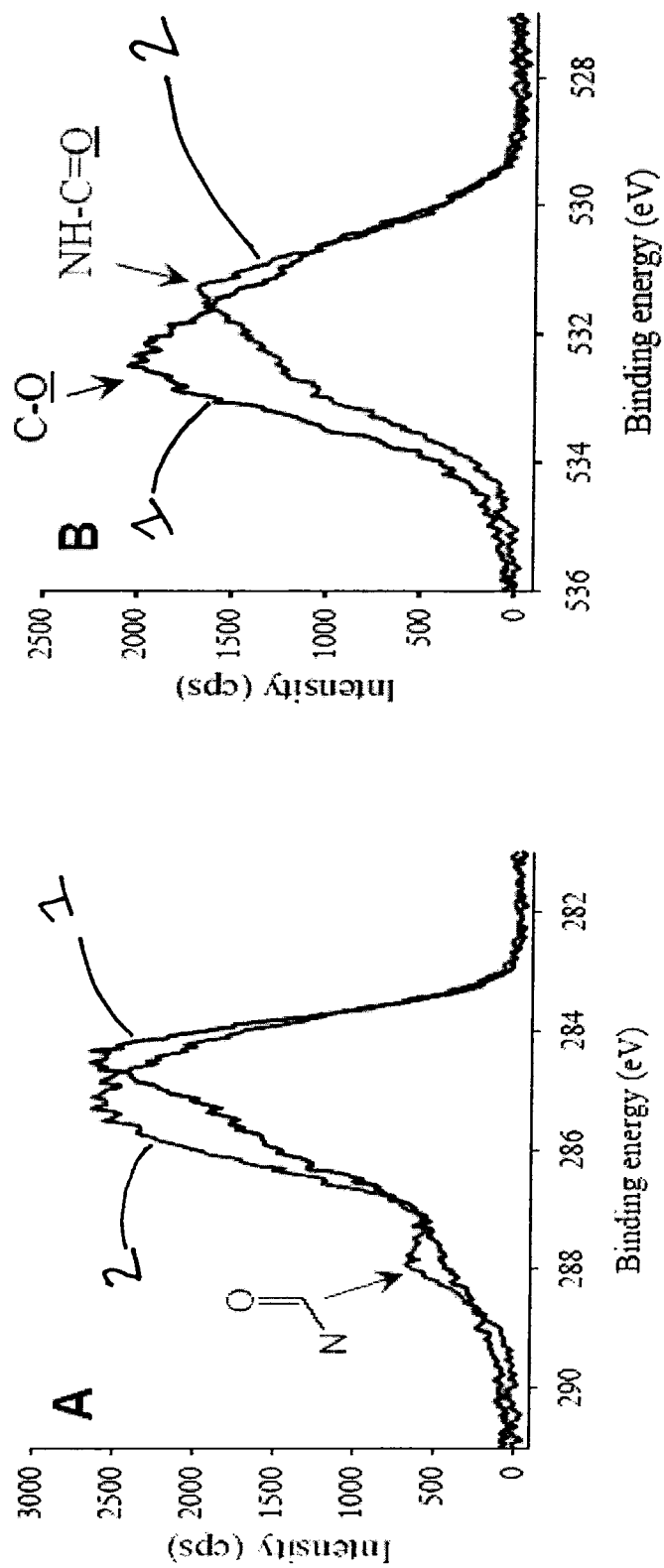
FIG. 20. High resolution x-ray photoelectron spectroscopy (XPS) analysis of C1s region (A) and O1s (B) of polydopamine-coated SiOx substrate after secondary reaction of pHis at pH 4.0 (1) and 6.8 (2).

Poly-histidine (0.5 mg/mL, Sigma, $M_w$=12,000) (pHis) was dissolved in acetate/phosphate/tris buffers with various pHs. Subsequently, polydopamine-coated substrates (prepared according to Example 1) were immersed in pHis-containing solutions buffered at various pHs (4.0 and 6.8) for 4 hrs. As shown in FIG. 11A, pHis surface reaction was pH-dependent; the surface carbon composition of the polydopamine-coated silicon wafer reacted with pHis at low pH showed the absence of a peptide carbon (O=C—NH) signal, whereas the peptide carbon was appeared in XPS from the surface immersed in the pHis-containing neutral buffer (pH=6.8), indicating that the deprotonated nitrogen in imidazole rings is chemically reactive toward polydopamine layers. Likewise, a new oxygen signal from peptide bonds (approximately 531 eV) was detected at the polydopamine-coated silicon substrate reacted with pHis at pH 6.8 (FIG. 20B).

Figure 21:
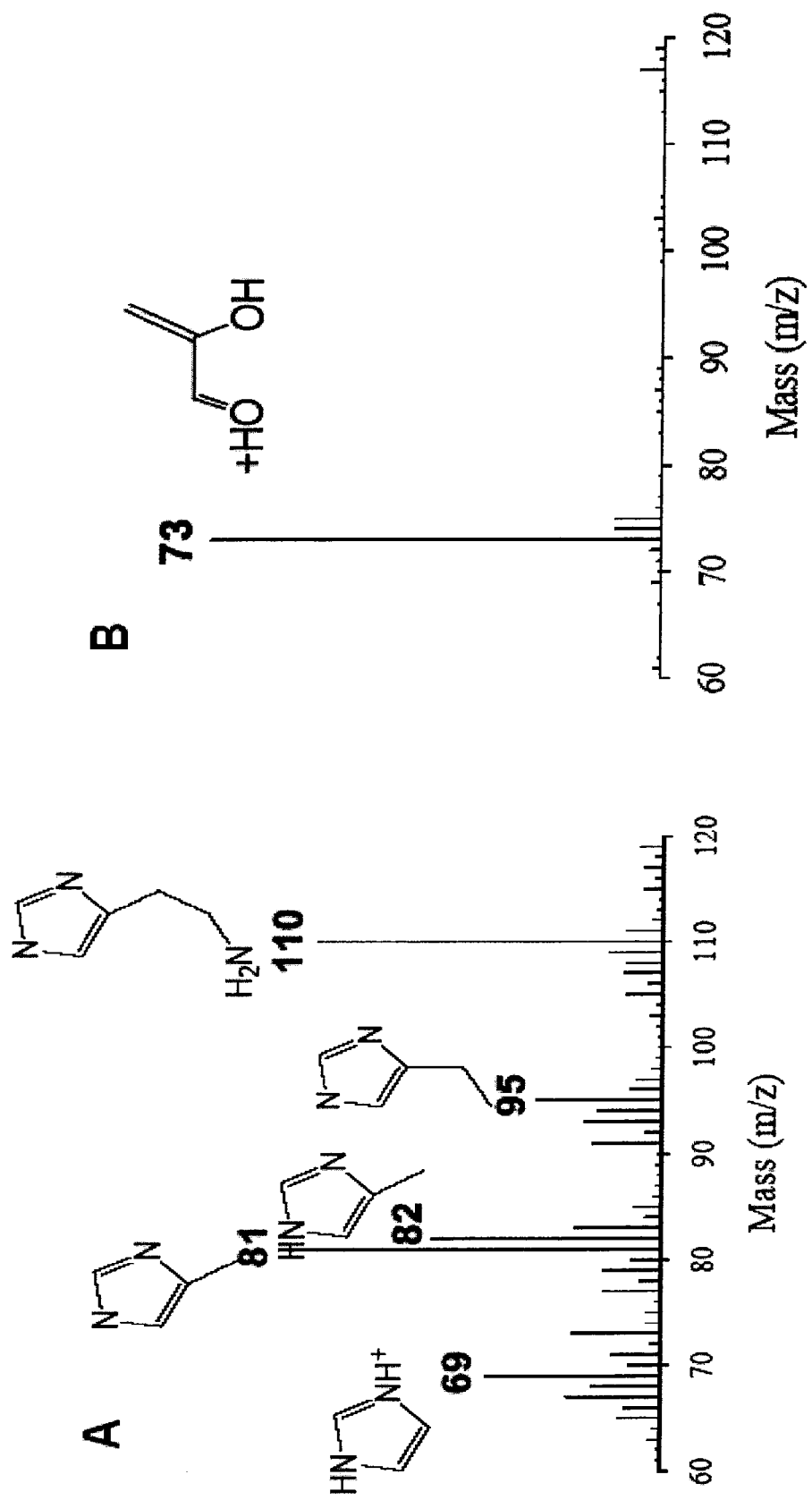
FIG. 21. ToF-SIMS analysis of pHis-polydopamine-coated silicon substrate (A); Polydopamine-coated substrate (B).

The pHis-conjugated polydopamine-coated silicon surface previously characterized in XPS (pH 6.8 sample) was used for time-of-flight secondary ion mass spectrometry (ToF SIMS) analysis. As shown in FIG. 21A, peaks (m/z=69, 81, 82, 95, and 110) detected from the pHis immobilized surface are reminiscent of imidazole-containing structures, which were not detected in the polydopamine-coated surface (FIG. 21B).

Figure 22:
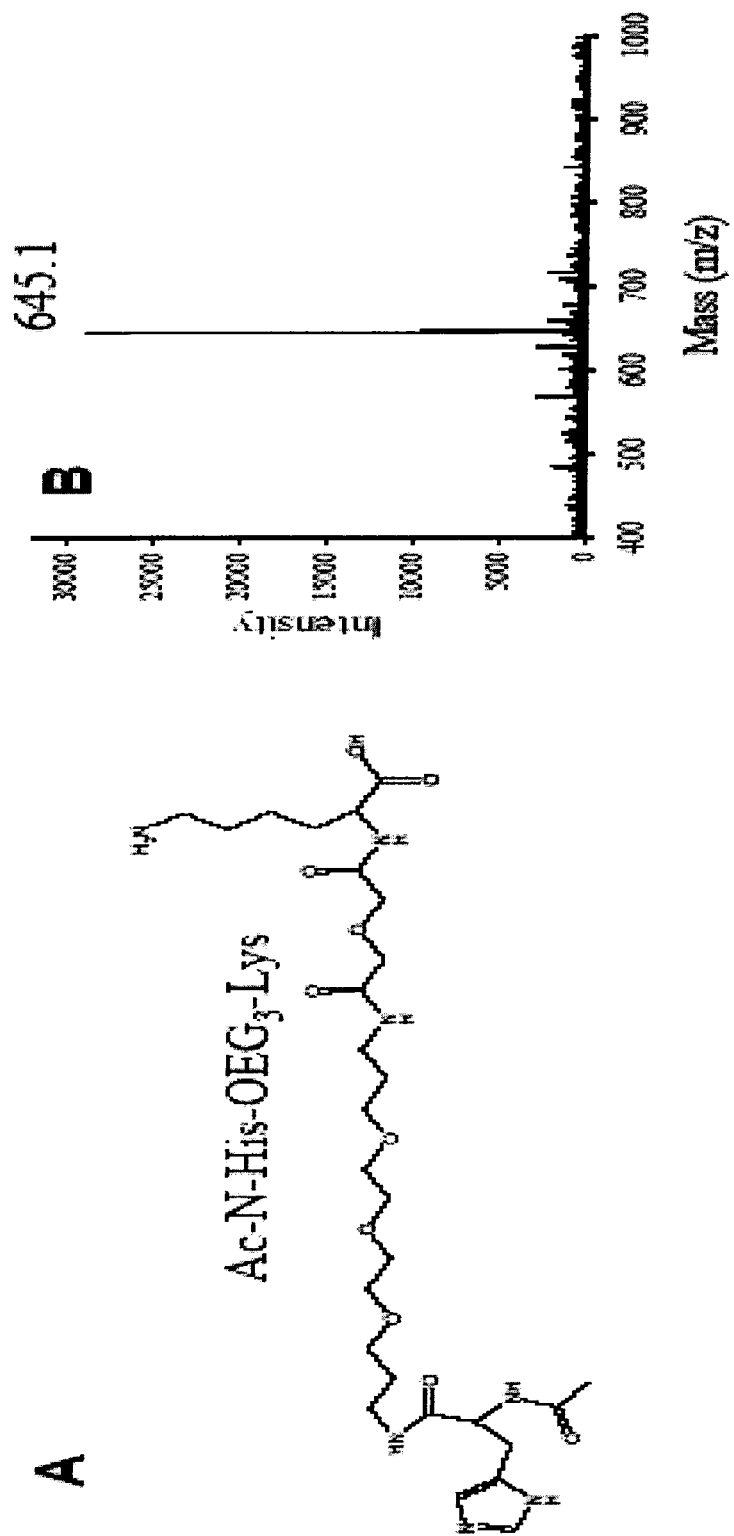
FIG. 22. Hetero-bifunctional Ac—N-His-OEG$_3$-Lys (A); Matrix Assisted Laser Desorption/Ionization Time of Flight mass spectrometry (MALDI-TOF MS) spectra after synthesis and purification of Ac—N-His-OEG$_3$-Lys (B).

Due to the difference in pKa of imidazole's secondary amine (approximately 6) and lysine's ∈-primary amine (approximately 10), it can be hypothesized that the corresponding amine group from each side chain might exhibit different reactivity onto polydopamine-coated substrates depending on reaction buffer pHs. A heterobifunctional molecule, N-acetyl-histidine-oligo(ethylene glycol)-lysine (Ac—N-His-OEG3-Lys), was designed and synthesized by using a standard Fmoc solid-phase peptide synthesis method (FIG. 22A). Matrix-assisted laser desorption/ionization time-of-flight (MALDI TOF) mass spectrometry showed the successful synthesis of Ac—N-His-OEG3-Lys (m/z=645.1) (FIG. 22B).

The Ac—N-His-OEG3-Lys molecule (hereafter His-Lys) can be covalently immobilized via either secondary amine of imidazole (polydopamine-His) or ∈-amine of lysine (polydopamine-Lys) side chain, which significantly impacts the orientation of the ∈-primary amine or imidazole groups with respect to the substrate surface. The ∈-primary amine is exposed to an aqueous solvent if histidine reacts with a polydopamine layer, or is alternatively not exposed to the solvent as a result of lysine reaction with the polydopamine layer, and the predominant orientation may therefore be controlled by the pH of the medium during reaction as shown in the following example where N-hydroxysuccinimidyl biotin and subsequent peroxidase-conjugated streptavidin coupling was used to determine the orientation of His-Lys molecules.

Figure 23:
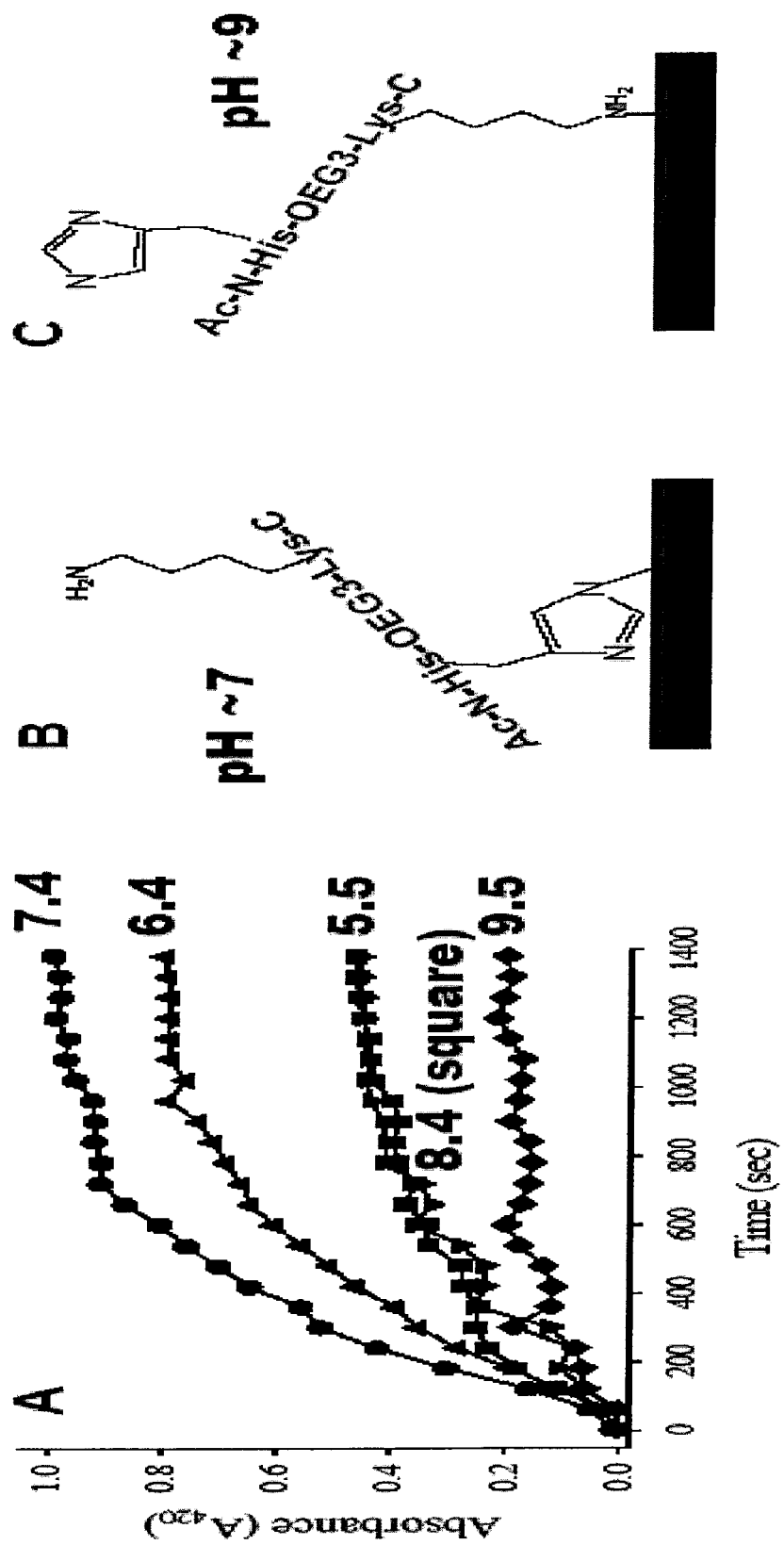
FIG. 23. Peroxidase activities monitored at 420 nm as a function of pH (A); Polydopamine-His configuration allowed biotinylation which serves as a platform for streptavidin-peroxidase immobilization at mild acidic and neutral pHs (B); Polydopamine-Lys orientation prevented biotinylation/streptavidin-peroxidase immobilization, resulting in low peroxidase activities at alkaline pHs (C).

Surface coupling reactions of His-Lys molecules (0.1 mM) dissolved in 10 mM acetate/phosphate-/tris co-buffer, (pH 5.5, 6.4, 7.4, 8.4, and 9.5) for 5 hrs followed by biotinylation (10 mM) (4 hrs, in 10 mM phosphate buffer pH 7.8) were performed. The colorimetric enzyme assay for peroxidase resulted in pH-dependent enzyme activities (FIG. 23A), demonstrating preferential orientation of His-Lys molecules covalently immobilized on polydopainine-coated substrates (FIG. 23B-C). The enzyme activity was monitored by the colorimetric product, purpurogallin, at 420 nm in which pyrogallol and hydrogen peroxide were used as substrates.

10 mg/mL of pyrogallol in 0.1 M phosphate buffer (pH 6.0) and a dilute hydrogen peroxide solution (1:74=$H_2O_2$:$H_2O$, v/v) were prepared as substrates for peroxidase. The peroxidase reaction was triggered by the vertical insertion of the enzyme-immobilized polydopamine surface to a quartz cuvette. Composition of the substrate solution is as follows: 2.0 mL of phosphate buffer, pH 6.0, 0.3 mL of pyrogallol solution, pH 6.0, and 0.2 mL of hydrogen peroxide solution.

Example 14

Norepinephrine-Treated Substrates

Inspired by the surface-independent coating ability of dopamine, a structural derivative of dopamine, norepinephrine, was also tested and found to exhibit the versatile surface-modifying property. A wide range of substrates (noble metals, oxides, polymers, semiconductors, and ceramics) were treated with norepinephrine (15-20 hrs, 2 mg of norepinephrine per milliliter of 10 mM tris, pH 7.5 or higher and non-aqueous solvents such as chloroform, dichloromethane, methanol, ethanol, (iso)-propanol, dimethylformamide, dimethylsulfoxide, hexane, etc.), and subsequently the substrates were rinsed with water. Contact angle of each substrate was measured before (hatch) and after (solid) norepinephrine coating (FIG. 25).

Figure 25:
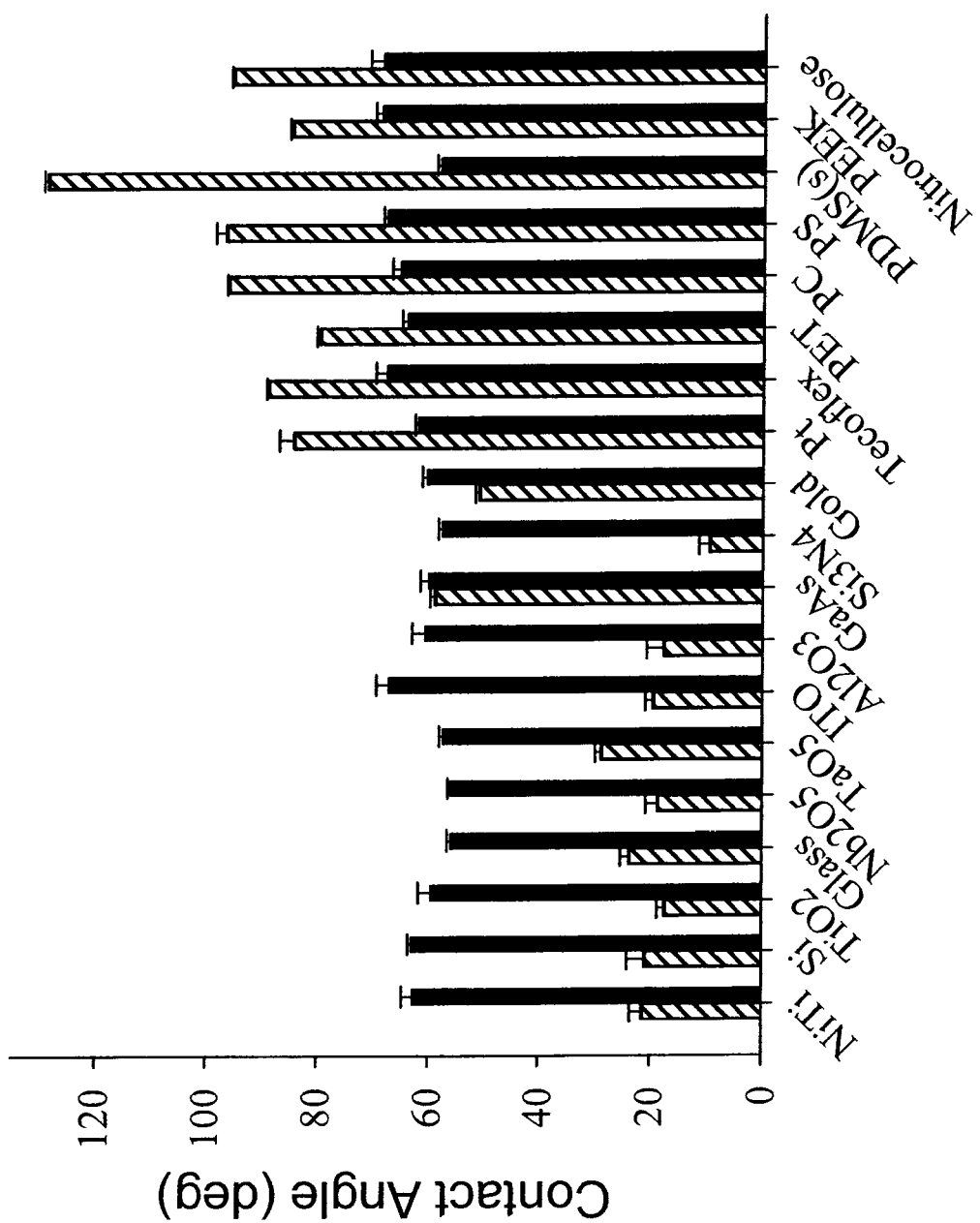
FIG. 25. Contact angle of each substrate was measured before (solid) and after (hatch) norepinephrine coating. The contact angle after coating was relatively consistent, indicating successful norepinephrine coating, whereas the contact angles of bare materials varied from hydrophilic (approximately 10°) to hydrophobic (approximately 130°).

As shown in FIG. 25, the contact angle after coating was relatively consistent (approximately 60°) indicating successful norepinephrine coating, whereas the contact angles of bare materials varied from hydrophilic (approximately 10°) to hydrophobic (approximately 130°).

It should be noted that the above description, attached figures and their descriptions are intended to be illustrative and not limiting of this invention. Many themes and variations of this invention will be suggested to one skilled in this and, in light of the disclosure. All such themes and variations are within the contemplation hereof. For instance, while this invention has been described in conjunction with the various exemplary embodiments outlined above, various alternatives, modifications, variations, improvements, and/or substantial equivalents, whether known or that rare or may be presently unforeseen, may become apparent to those having at least ordinary skill in the art. Various changes may be made without departing from the spirit and scope of the invention. Therefore, the invention is intended to embrace all known or later-developed alternatives, modifications, variations, improvements, and/or substantial equivalents of these exemplary embodiments.

REFERENCES

Love et al., Chem. Rev. 105, 1103 (2005).
Erli et al., Biomed. Eng. Online 2, 15 (2003).
Young et al., Marine animals and adhesion. W. K Allen, Ed.
Waite et al, Science 212, 1038 (1981).
Yu et al., Macromolecules 31, 4739 (1998).
Statz et al., J. Am. Chem. Soc. 127, 7972 (2005).
Dalsin et al. J. Am. Chem. Soc. 125, 4253 (2003).
Bharathi et al., Chem. Commun., 2303 (1997).
Ratner et al., Biomaterials science: an introduction to materials in medicine.
Alivisatos, Nat. Biotech. 22, 47 (2004).
Zeise et al., Melanin: Its role in human photoprotection (1995).
LaVoie et al., Nature Med. 11, 1214 (2005).
Burzio et al., Biochemistry 39, 11147 (2000).
Sugumaran et al., Arch. Insect Biochem. Phys 11, 127 (1989).
Gidanian et al., J. Inorg. Biochem. 89, 54 (2002).
Taylor et al., J. Inorg. Chem. 33, 5819 (1994).
Jo et al., BIomaterials 21, 605 (2000).
Pasche et al., J. Phys. Chem. B 109, 17545 (2005).
Li et al., J. Phys. Chem. B 109, 2934 (2005).
Ostuni et al., Langmuir 17, 5605 (2001).
Korobkova et al., Nature 428, 574 (2004).
Ho et al., Adv. Mat. 16, 957 (2004).
Li et al., MRS Bulletin 18, 18 (1993).
Sawada et al., Langmuir 22, 332 (2006).
Carmichael et al., Langmuir 20, 5593 (2004).
Nakagawa et al., Biochem. Biophys. Res. Commun. 272, 505 (2000).

We claim:

1. A method of modifying a substrate surface, the method comprising contacting at least a portion of the substrate with an alkaline solution under oxidative conditions, the solution comprising a surface-modifying agent according to Formula I:

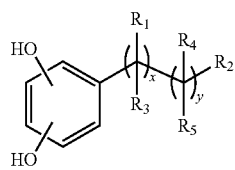

wherein each of $R_1$, $R_3$, $R_4$ and $R_5$ is independently selected from the group consisting of a thiol, a primary amine, a secondary amine, a nitrile, an aldehyde, an imidazole, an azide, a halide, a hydrogen, a hydroxyl, a carboxylic acid, an aldehyde;

wherein $R_2$ is $NH_2$;

wherein x ranges from 0 to 10 and wherein y ranges from 0 to 10, provided that x or y is at least 1;

wherein the substrate surface is modified when the surface-modifying agent reacts to form a polymeric coat on the substrate surface.

2. The method of claim 1 wherein x and y are both 1, and wherein $R_1$ and $R_4$ form a double bond when eliminated.

3. The method of claim 1 wherein one of $R_1$ or $R_4$ is a halide, a hydroxyl or a thiol, and wherein one of $R_3$ or $R_5$ is a hydrogen atom.

4. The method of claim 1 wherein x is 1, y is 1, $R_1$ is a hydroxyl, and wherein each of $R_3$, $R_4$ and $R_5$ are hydrogen atoms.

5. The method of claim 1 wherein x and y are each 1 and wherein each of $R_1$, $R_3$, $R_4$ and $R_5$ are hydrogen atoms.

6. The method of claim 1 wherein x+y is at least 2.

7. The method of claim 1 wherein x+y is at least 3.

8. The method of claim 1 wherein the hydroxyls of the phenyl moiety are positioned at the 3 and 4 positions of the phenyl group relative to the side chain.

9. The method of claim 1 wherein the surface-modifying agent is selected from the group consisting of 3,4-dihydroxy-L-phenylalanine (DOPA), 3,4-dihydroxyphenylalanine methyl ester, dopamine, norepinephrine and epinephrine.

10. The method of claim 1 wherein the solution is aqueous.

11. The method of claim 1 wherein x+y ranges from 1 to 6.

12. The method of claim 1, wherein the oxidative conditions are spontaneous oxidative conditions.

13. A method of modifying a substrate surface, the method comprising contacting at least a portion of the substrate with an alkaline solution under oxidative conditions, the solution comprising a surface-modifying agent selected from the group consisting of 3,4-dihydroxy-L-phenylalanine (DOPA), 3,4-dihydroxyphenylalanine methyl ester, dopamine, norepinephrine and epinephrine;

wherein the substrate surface is modified.

14. The method of claim 13, wherein the oxidative conditions are spontaneous oxidative conditions.

* * * * *

UNITED STATES PATENT AND TRADEMARK OFFICE
CERTIFICATE OF CORRECTION

PATENT NO.        : 8,541,060 B2
APPLICATION NO.   : 11/875237
DATED             : September 24, 2013
INVENTOR(S)       : Phillip B. Messersmith and Haeshin Lee Page 1 of 1

It is certified that error appears in the above-identified patent and that said Letters Patent is hereby corrected as shown below:

In the Specification

Column 1, line 17 replace the paragraph after the STATEMENT REGARDING FEDERALLY SPONSORED RESEARCH OR DEVELOPMENT heading with the following:

-- This invention was made with government support under grant number DE014193 awarded by the National Institutes of Health. The government has certain rights in the invention. --

Column 4, line 33    "nitrites" should be -- nitriles --
Column 5, line 57    "polydopainine" should be -- polydopamine --
Column 6, line 5     "leikodopaminechrome" should be -- leukodopaminechrome --
Column 7, line 63    "Pre-nornalized" should be -- Pre-normalized --
Column 9, line 3     "TOF" should be -- ToF --
Column 9, line 30    "w hereby" should be -- whereby --
Column 10, line 12   "in" should be -- an --
Column 17, line 18   "in" should be -- an --
Column 17, line 57   "nitrites" should be -- nitriles --
Column 18, line 12   "nitrites" should be -- nitriles --
Column 26, line 37   "polydopainine" should be -- polydopamine --
Column 30, line 49   "polydopainine" should be -- polydopamine --
Column 33, line 38   "polydopainine" should be -- polydopamine --

Signed and Sealed this
Twenty-fourth Day of June, 2014

Michelle K. Lee
*Deputy Director of the United States Patent and Trademark Office*